(12) United States Patent
Oh et al.

(10) Patent No.: US 11,926,591 B2
(45) Date of Patent: Mar. 12, 2024

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hong-Se Oh, Gyeonggi-do (KR); Jeong-Eun Yang, Gyeonggi-do (KR); Tae-Jin Lee, Gyeonggi-do (KR); Sang-Hee Cho, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 788 days.

(21) Appl. No.: 16/968,888

(22) PCT Filed: Feb. 12, 2019

(86) PCT No.: PCT/KR2019/001683
§ 371 (c)(1),
(2) Date: Aug. 11, 2020

(87) PCT Pub. No.: WO2019/164165
PCT Pub. Date: Aug. 29, 2019

(65) Prior Publication Data
US 2021/0024466 A1 Jan. 28, 2021

(30) Foreign Application Priority Data

Feb. 22, 2018 (KR) .................. 10-2018-0021237
Jan. 3, 2019 (KR) .................. 10-2019-0000623

(51) Int. Cl.
| | | |
|---|---|---|
| C07D 209/82 | (2006.01) |
| C07D 307/91 | (2006.01) |
| C07D 333/76 | (2006.01) |
| C07D 401/04 | (2006.01) |
| C07D 401/10 | (2006.01) |
| C07D 401/14 | (2006.01) |
| C07D 405/14 | (2006.01) |
| C07D 409/14 | (2006.01) |
| C07D 487/04 | (2006.01) |

(52) U.S. Cl.
CPC ........ *C07D 209/82* (2013.01); *C07D 307/91* (2013.01); *C07D 333/76* (2013.01); *C07D 401/04* (2013.01); *C07D 401/10* (2013.01); *C07D 401/14* (2013.01); *C07D 405/14* (2013.01); *C07D 409/14* (2013.01); *C07D 487/04* (2013.01)

(58) Field of Classification Search
None
See application file for complete search history.

(56) References Cited

U.S. PATENT DOCUMENTS

| | | |
|---|---|---|
| 7,737,627 B2 | 6/2010 | Hwang et al. |
| 10,164,195 B2 | 12/2018 | Kim et al. |
| 2017/0179396 A1 | 6/2017 | Kim et al. |
| 2017/0279050 A1 | 9/2017 | Chen et al. |
| 2017/0324037 A1 | 11/2017 | Itoi et al. |
| 2020/0235307 A1 | 7/2020 | Cho et al. |

FOREIGN PATENT DOCUMENTS

| | | |
|---|---|---|
| KR | 2015-0104259 A | 9/2015 |
| KR | 2015-0121337 A | 10/2015 |

OTHER PUBLICATIONS

Li, X. et al., "Palladium-Catalyzed Double Suzuki Reactions: Synthesis of Dibenzo[4,5:6,7]cyclohepta[1,2,3-de] naphthalenes.", Asian Journal of Organic Chemistry. Dec. 2017, vol. 6 Issue 12, p. 1876-1884.
1st Notice of Preliminary Rejection for Korean Patent Application No. 10-2019-0000623; dated Jan. 1, 03 2019.
Prior Arts Search Report for expedited examination for Korea Patent Application No. 10-2019-0000623, Filing Date: Jan. 03. 2019.

*Primary Examiner* — Jay Yang
(74) *Attorney, Agent, or Firm* — G. Creston Campbell

(57) ABSTRACT

The present disclosure relates to an organic electroluminescent compound and an organic electroluminescent device comprising the same. By comprising the organic electroluminescent compound of the present disclosure, an organic electroluminescent device having improved driving voltage, luminous efficiency, and/or lifespan characteristics can be provided.

8 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor in determining luminous efficiency in an organic electroluminescent device is light-emitting materials. Until now, fluorescent materials have been widely used as a light-emitting material. However, in view of electroluminescent mechanisms, since phosphorescent light-emitting materials theoretically enhance luminous efficiency by four (4) times compared to fluorescent light-emitting materials, development of phosphorescent light-emitting materials are widely being researched. To date, iridium(III) complexes have been widely known as phosphorescent light-emitting materials, including bis(2-(2'-benzothienyl)-pyridinato-N,C3')iridium(acetylacetonate) ((acac)Ir(btp)$_2$), tris(2-phenylpyridine)iridium (Ir(ppy)$_3$) and bis(4,6-difluorophenylpyridinato-N,C2)picolinato iridium (Firpic) as red, green, and blue materials, respectively.

At present, 4,4'-N,N'-dicarbazol-biphenyl (CBP) is the most widely known phosphorescent host material. Recently, Pioneer (Japan) et al. developed a high performance organic electroluminescent device using bathocuproine (BCP) and aluminum(III)bis(2-methyl-8-quinolinate)(4-phenylphenolate) (BAlq), etc., which were used as hole blocking layer materials, as host materials.

Although these materials provide good light-emitting characteristics, they have the following disadvantages: (1) Due to their low glass transition temperature and poor thermal stability, their degradation may occur during a high-temperature deposition process in a vacuum, and the lifespan of the device decreases. (2) The power efficiency of an organic electroluminescent device is given by [(π/voltage)×current efficiency], and the power efficiency is inversely proportional to the voltage. Although an organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Further, when these materials are used in an organic electroluminescent device, the operational lifespan of an organic electroluminescent device is short and luminous efficiency is still required to be improved.

In addition, copper phthalocyanine (CuPc), 4,4'-bis[N-(1-naphthyl)-N-phenylamino]biphenyl (NPB), N,N'-diphenyl-N,N'-bis(3-methylphenyl)-(1,1'-biphenyl)-4,4'-diamine (TPD), 4,4',4''-tris(3-methylphenylphenylamino)triphenylamine (MTDATA), etc., were used as a hole injection and transport material in an organic electroluminescent device. However, an organic electroluminescent device using these materials is problematic in deteriorating quantum efficiency and lifespan when an organic electroluminescent device is driven under high current, thermal stress occurs between an anode and a hole injection layer, and the thermal stress significantly reduces the lifespan of the device. Further, since the organic material used in the hole injection layer has very high hole mobility, the hole-electron charge balance may be broken and quantum efficiency (cd/A) may decrease.

In order to enhance luminous efficiency, driving voltage and/or lifespan, various materials or concepts for an organic layer of an organic electroluminescent device have been proposed. However, they were not satisfactory in practical use.

Korean Patent No. 0573137 discloses an electroluminescent compound including a fluorene structure and a carbazole structure. However, it is still required to be improved in terms of driving voltage, luminous efficiency, and lifespan characteristics.

DISCLOSURE OF THE INVENTION

Problems to be Solved

The objective of the present disclosure is to provide i) an organic electroluminescent compound which can efficiently produce an organic electroluminescent device having improved driving voltage, luminous efficiency, and/or lifespan characteristics, and ii) an organic electroluminescent device comprising the organic electroluminescent compound.

Solution to Problems

Generally, a thin film made of a material having a low glass transition temperature may be easily deformed by heat generated when driving a device, and the charge mobility in the thin film may be reduced to lower the performance of an organic electroluminescent device. Thus, a material having a high glass transition temperature may be advantageous in an organic electroluminescent device. Among various methods to raise the glass transition temperature, the method which may be relatively easily practiced is to increase the molecular weight by binding a substituent. However, according to said method, there is a limit since the deposition temperature of an organic compound also increases. As a result of intensive studies to solve the technical problem above, the present inventors found that the organic electroluminescent compound of the present disclosure has a twisted structure, and thus has a higher glass transition temperature (Tg) than other compounds having the same molecular weight, thereby providing excellent thermal stability, and contributing to an achievement of the objective of the present disclosure. Specifically, the present inventors found that the above objective can be achieved by an organic electroluminescent compound represented by the following formula 1:

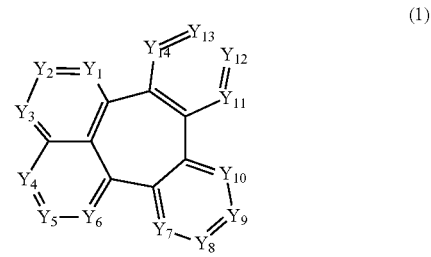

(1)

wherein $Y_1$ to $Y_{14}$ each independently represent N or $CR_1$, in which if a plurality of $R_1$'s is present, each $R_1$ may be the same or different;

with the proviso that at least a pair of $Y_1$ to $Y_{14}$ wherein two of $Y_1$ to $Y_{14}$ are adjacent to each other are fused with the following formula 2 to form a ring:

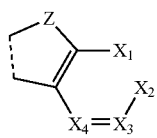

(2)

Z represents $NR_2$, O, S, $CR_3R_4$ or $SiR_5R_6$;

$X_1$ to $X_4$ each independently represent N or $CR_7$, in which if a plurality of $R_7$'s is present, each $R_7$ may be the same or different;

the dotted line represents a site fused with the adjacent two of $Y_1$ to $Y_{14}$ of formula 1;

$R_2$ represents

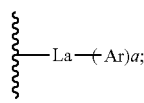

La represents a single bond, a substituted or unsubstituted (C6-C30)arylene, a substituted or unsubstituted (3- to 30-membered)heteroarylene, or a substituted or unsubstituted (C3-C30)cycloalkylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C6-C30)aryl(3- to 30-membered)heteroarylamino, or a substituted or unsubstituted (C1-C30)alkyl(C6-C30)arylamino;

$R_1$ and $R_7$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C6-C30)aryl(3- to 30-membered)heteroarylamino, or a substituted or unsubstituted (C1-C30)alkyl(C6-C30)arylamino; or adjacent two $R_1$'s or adjacent two $R_7$'s may be linked to each other to form a ring;

$R_3$ to $R_6$ each independently represent hydrogen, deuterium, a halogen, a cyano, a substituted or unsubstituted (C1-C30)alkyl, a substituted or unsubstituted (C6-C30)aryl, or a substituted or unsubstituted (3- to 30-membered)heteroaryl; or $R_3$ and $R_4$, or $R_5$ and $R_6$ may be linked to each other to form a ring; and a is an integer of 1 to 4, in which if a is 2 or more, each Ar may be the same or different.

Effects of the Invention

By using the organic electroluminescent compound according to the present disclosure, an organic electroluminescent device having low driving voltage, high luminous efficiency, and/or excellent lifespan characteristic can be produced.

EMBODIMENTS OF THE INVENTION

Hereinafter, the present disclosure will be described in detail. However, the following description is intended to explain the disclosure, and it is not meant in any way to restrict the scope of the disclosure.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device. The compound represented by formula 1 may be comprised in at least one layer of a light-emitting layer and layers constituting a hole transport zone and/or an electron transport zone, but is not limited thereto. When comprised in the light-emitting layer, the compound of formula 1 can be comprised as a host material, in which the host material may be a host material of a green or red light-emitting organic electroluminescent device. Further, when comprised in a hole transport zone, the compound of formula 1 can be comprised in a hole transport layer, a hole auxiliary layer, and/or a light-emitting auxiliary layer, and can be comprised as a hole transport material, a hole auxiliary material, and/or a light-emitting auxiliary material, respectively. In addition, when comprised in an electron transport zone, the compound of formula 1 can be comprised in a hole blocking layer, an electron transport layer, an electron buffer layer, and/or an electron injection layer, and can be comprised as a hole blocking material, an electron transport material, an electron buffer material, and/or an electron injection material, respectively.

Hereinafter, the compound represented by formula 1 will be described in detail.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl(ene)" is meant to be a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is meant to be a cycloalkyl having at least one heteroatom selected from the group consisting of B, N, O, S, Si, and P, preferably selected from the group consisting of O, S, and N, and 3 to 7 ring backbone atoms, preferably 5 to 7 ring backbone atoms, and includes tetrahydrofuran, pyrrolidine, thiolan, tetrahydropyran, etc. "(C6-C30)aryl(ene)" is meant to be a monocyclic or fused ring radical derived from an aromatic hydrocarbon having 6 to 30 ring backbone carbon atoms and may be partially saturated, in which the number of ring backbone carbon atoms is preferably 6 to 25, more preferably 6 to 18, includes a spiro structure, and includes phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the above aryl(ene) may include a phenyl group, a 1-naphthyl group, a 2-naphthyl group, a 1-anthryl group, a 2-anthryl group, a 9-anthryl group, a benzanthryl group, a 1-phenanthryl group, a 2-phenanthryl group, a 3-phenanthryl group, a 4-phenanthryl group, a 9-phenanthryl group, a naphthacenyl group, a pyrenyl group, a 1-chrysenyl group, a 2-chrysenyl group, a 3-chrysenyl group, a 4-chrysenyl group, a 5-chrysenyl group, a 6-chrysenyl group, a benzo[c]phenanthryl group, a benzo[g]chrysenyl group, a 1-triphenylenyl group, a 2-triphenylenyl group, a 3-triphenylenyl group, a 4-triphenylenyl group, a 1-fluorenyl group, a 2-fluorenyl group, a 3-fluorenyl group, a 4-fluorenyl group, a 9-fluorenyl group, a benzofluorenyl group, a dibenzofluorenyl group, a 2-biphenylyl group, a 3-biphenylyl group, a 4-biphenylyl group, an o-terphenyl group, an m-terphenyl-4-yl group, an m-terphenyl-3-yl group, an m-terphenyl-2-yl group, a p-terphenyl-4-yl group, a p-terphenyl-3-yl group, a p-terphenyl-2-yl group, an m-quaterphenyl group, a 3-fluoranthenyl group, a 4-fluoranthenyl group, an 8-fluoranthenyl group, a 9-fluoranthenyl group, a benzofluoranthenyl group, an o-tolyl group, an m-tolyl group, a p-tolyl group, a 2,3-xylyl group, a 3,4-xylyl group, a 2,5-xylyl group, a mesityl group, an o-cumenyl group, an m-cumenyl group, a p-cumenyl group, a p-t-butylphenyl group, a p-(2-phenylpropyl)phenyl group, a 4'-methylbiphenylyl group, a 4''-t-butyl-p-terphenyl-4-yl group, a 9,9-dimethyl-1-fluorenyl group, a 9,9-dimethyl-2-fluorenyl group, a 9,9-dimethyl-3-fluorenyl group, a 9,9-dimethyl-4-fluorenyl group, a 9,9-diphenyl-1-fluorenyl group, a 9,9-diphenyl-2-fluorenyl group, a 9,9-diphenyl-3-fluorenyl group, and a 9,9-diphenyl-4-fluorenyl group. "(3- to 30-membered) heteroaryl(ene)" is meant to be an aryl group having at least one, preferably 1 to 4 heteroatoms selected from the group consisting of B, N, O, S, Si, and P, and 3 to 30 ring backbone atoms; is a monocyclic ring, or a fused ring condensed with at least one benzene ring; may be partially saturated; may be one formed by linking at least one heteroaryl or aryl group to a heteroaryl group via a single bond(s); includes a spiro structure; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, di benzocarbazolyl, phenoxazinyl, phenothiazinyl, phenanthridinyl, benzodioxolyl, dihydroacridinyl, etc. More specifically, the above hereroaryl(ene) may include a 1-pyrrolyl group, a 2-pyrrolyl group, a 3-pyrrolyl group, a pyrazinyl group, a 2-pyridinyl group, a 2-pyrimidinyl group, a 4-pyrimidinyl group, a 5-pyrimidinyl group, a 6-pyrimidinyl group, a 1,2,3-triazin-4-yl group, a 1,2,4-triazin-3-yl group, a 1,3,5-triazin-2-yl group, a 1-imidazolyl group, a 2-imidazolyl group, a 1-pyrazolyl group, a 1-indolidinyl group, a 2-indolidinyl group, a 3-indolidinyl group, a 5-indolidinyl group, a 6-indolidinyl group, a 7-indolidinyl group, an 8-indolidinyl group, a 2-imidazopyridinyl group, a 3-imidazopyridinyl group, a 5-imidazopyridinyl group, a 6-imidazopyridinyl group, a 7-imidazopyridinyl group, an 8-imidazopyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, an azacarbazolyl-1-yl group, an azacarbazolyl-2-yl group, an azacarbazolyl-3-yl group, an azacarbazolyl-4-yl group, an azacarbazolyl-5-yl group, an azacarbazolyl-6-yl group, an azacarbazolyl-7-yl group, an azacarbazolyl-8-yl group, an azacarbazolyl-9-yl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, a 4-dibenzothiophenyl group, a 1-silafluorenyl group, a 2-silafluorenyl group, a 3-silafluorenyl group, a 4-silafluorenyl group, a 1-germafluorenyl group, a 2-germafluorenyl group, a 3-germafluorenyl group, and a 4-germafluorenyl group. "Halogen" includes F, Cl, Br, and I.

In addition, "ortho," "meta," and "para" signify substitution positions of two substituents. The ortho position represents a just neighboring position, and, for example, in the case of benzene, represents 1,2 positions. The meta position represents the position next to the just neighboring position, and, for example, in the case of benzene, represents 1,3 positions. The para position represents the position next to the meta position, and, for example, in the case of benzene, represents 1,4 positions.

Herein, "substituted" in the expression "substituted or unsubstituted" means that a hydrogen atom in a certain functional group is replaced with another atom or functional group, i.e., a substituent. The substituents of the substituted (C1-C30)alkyl, the substituted (C6-C30)aryl(ene), the substituted (3- to 30-membered)heteroaryl(ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C6-C30)aryl(3- to 30-membered) heteroarylamino, and the substituted (C1-C30)alkyl(C6-C30)arylamino in La, Ar, $R_1$, and $R_3$ to $R_7$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl; a (C6-C30)aryl unsubstituted or substituted with a (5- to 30-membered)heteroaryl; a tri(C1-C30)alkylsilyl, a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents each independently are a (C1-C6)alkyl and/or a (C6-C15)aryl. Specifically, the substituents may each independently be methyl and/or phenyl.

The compound of formula 1 may be represented by any one of the following formulas 3 and 4:

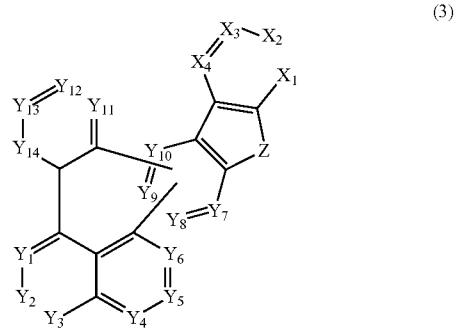

(3)

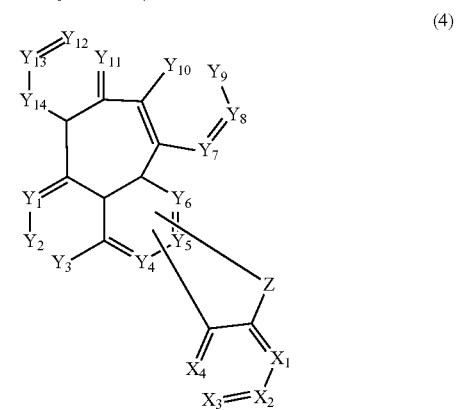

(4)

wherein
$Y_1$ to $Y_{14}$, Z, and $X_1$ to $X_4$ are as defined in formula 1.

In formula 1 above, $Y_1$ to $Y_{14}$ each independently represent N or $CR_1$, in which if a plurality of $R_1$'s is present, each $R_1$ may be the same or different, at least a pair of $Y_1$ to $Y_{14}$ wherein two of $Y_1$ to $Y_{14}$ are adjacent to each other are fused with formula 2 above to form a ring.

In formula 2 above, $X_1$ to $X_4$ each independently represent N or $CR_7$, in which if a plurality of $R_7$'s is present, each $R_7$ may be the same or different; and $R_2$ represents

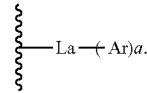

In formula 2 above, Z represents $NR_2$, O, S, $CR_3R_4$ or $SiR_5R_6$. In one embodiment of the present disclosure, Z represents $NR_2$, O or S.

In formula 2 above, La represents a single bond, a substituted or unsubstituted (C6-C30)arylene, a substituted or unsubstituted (3- to 30-membered)heteroarylene, or a substituted or unsubstituted (C3-C30)cycloalkylene. In one embodiment of the present disclosure, La represents a single bond, a substituted or unsubstituted (C6-C15)arylene, or a substituted or unsubstituted (5- to 15-membered)heteroarylene. In another embodiment of the present disclosure, La represents a single bond, an unsubstituted (C6-C15) arylene, or an unsubstituted (5- to 15-membered)heteroarylene. Specifically, La represents a single bond, phenylene, biphenylene, pyridylene, triazinylene, quinazolinylene, quinoxalinylene, benzoquinazolinylene, benzoquinoxalinylene, etc.

In formula 2 above, Ar represents hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C6-C30)aryl(3- to 30-membered)heteroarylamino, or a substituted or unsubstituted (C1-C30)alkyl(C6-C30)arylamino. In one embodiment of the present disclosure, Ar represents a substituted or unsubstituted (C6-C15)aryl, a substituted or unsubstituted (5- to 15-membered)heteroaryl, a substituted or unsubstituted di(C6-C15)arylamino, or a substituted or unsubstituted (C6-C15)aryl(5- to 15-membered)heteroarylamino. In another embodiment of the present disclosure, Ar represents an unsubstituted (C6-C15)aryl; a (5- to 15-membered)heteroaryl unsubstituted or substituted with a (C6-C15)aryl; a di(C6-C15)arylamino unsubstituted or substituted with a (C1-C6)alkyl; or an unsubstituted (C6-C15)aryl(5- to 15-membered)heteroarylamino. Specifically, Ar represents phenyl, biphenyl, diphenyltriazinyl, diphenylamino, phenylbiphenylamino, dibiphenylamino, biphenyldimethylfluorenylamino, phenyldibenzofuranylamino, phenyldibenzothiophenylamino, biphenyldibenzofuranylamino, biphenyldibenzothiophenylamino, etc.

In formula 2 above, $R_1$ and $R_7$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C6-C30)aryl(3- to 30-membered)heteroarylamino, or a substituted or unsubstituted (C1-C30)alkyl(C6-C30)arylamino; or adjacent two $R_1$'s or adjacent two $R_7$'s may be linked to each other to form a ring.

In one embodiment of the present disclosure, $R_1$ represents hydrogen.

In one embodiment of the present disclosure, $R_7$ represents hydrogen, a substituted or unsubstituted (C6-C15)aryl, a substituted or unsubstituted (5- to 15-membered)heteroaryl, a substituted or unsubstituted di(C6-C15)arylamino, or a substituted or unsubstituted (C6-C15)aryl(5- to 15-membered)heteroarylamino. In another embodiment of the present disclosure, $R_7$ represents hydrogen; an unsubstituted (C6-C15)aryl; a (5- to 15-membered)heteroaryl unsubstituted or substituted with a (C6-C15)aryl; a di(C6-C15)arylamino unsubstituted or substituted with a (C1-C6)alkyl; or an unsubstituted (C6-C15)aryl(5- to 15-membered)heteroarylamino. Specifically, $R_7$ represents hydrogen, phenylbiphenyltriazinyl, phenylquinazolinyl, phenylquinoxalinyl, diphenylamino, phenylbiphenylamino, phenyldimethylfluorenylamino, phenyldibenzofuranylamino, etc.

In formula 2 above, $R_3$ to $R_6$ each independently represent hydrogen, deuterium, a halogen, a cyano, a substituted or unsubstituted (C1-C30)alkyl, a substituted or unsubstituted (C6-C30)aryl, or a substituted or unsubstituted (3- to 30-membered)heteroaryl; or $R_3$ and $R_4$, or $R_5$ and $R_6$ may be linked to each other to form a ring.

a is an integer of 1 to 4, in which if a is 2 or more, each Ar may be the same or different. In one embodiment of the present disclosure, a is 1 or 2.

According to one embodiment of the present disclosure, Z represents $NR_2$, O or S; La represents a single bond, a substituted or unsubstituted (C6-C15)arylene, or a substituted or unsubstituted (5- to 15-membered)heteroarylene; Ar represents a substituted or unsubstituted (C6-C15)aryl, a substituted or unsubstituted (5- to 15-membered)heteroaryl, a substituted or unsubstituted di(C6-C15)arylamino, or a substituted or unsubstituted (C6-C15)aryl(5- to 15-membered)heteroarylamino; $R_1$ represents hydrogen; $R_7$ represents hydrogen, a substituted or unsubstituted (C6-C15)aryl, a substituted or unsubstituted (5- to 15-membered)heteroaryl, a substituted or unsubstituted di(C6-C15)arylamino, or a substituted or unsubstituted (C6-C15)aryl(5- to 15-membered)heteroarylamino; and a is 1 or 2.

According to another embodiment of the present disclosure, Z represents $NR_2$, O or S; La represents a single bond, an unsubstituted (C6-C15)arylene, or an unsubstituted (5- to 15-membered)heteroarylene; Ar represents an unsubstituted (C6-C15)aryl, a (5- to 15-membered)heteroaryl unsubstituted or substituted with a (C6-C15)aryl, a di(C6-C15)arylamino unsubstituted or substituted with a (C1-C6)alkyl, or an unsubstituted (C6-C15)aryl(5- to 15-membered)heteroarylamino; $R_1$ represents hydrogen; $R_7$ represents hydrogen, an unsubstituted (C6-C15)aryl, a (5- to 15-membered) heteroaryl unsubstituted or substituted with a (C6-C15)aryl, a di(C6-C15)arylamino unsubstituted or substituted with a (C1-C6)alkyl, or an unsubstituted (C6-C15)aryl(5- to 15-membered)heteroarylamino; and a is 1 or 2.

In the formulas of the present disclosure, if adjacent substituents are linked to each other to form a ring, the ring may be a substituted or unsubstituted, mono- or polycyclic, alicyclic or aromatic (3- to 30-membered) ring, or the combination thereof, in which the formed ring may contain at least one heteroatom selected from nitrogen, oxygen, and sulfur. For example, the fused ring may be a substituted or unsubstituted dibenzothiophene ring, a substituted or unsubstituted dibenzofurane ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl (ene) may each independently contain at least one heteroatom selected from B, N, O, S, Si, and P. In addition, the heteroatom may be substituted with at least one substituent selected from the group consisting of hydrogen, deuterium, a halogen, a cyano, a substituted or unsubstituted (C1-C30) alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.
The compound represented by formula 1 includes the following compounds, but is not limited thereto:
A-1
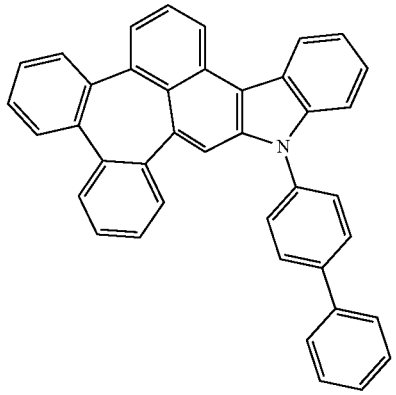
A-2
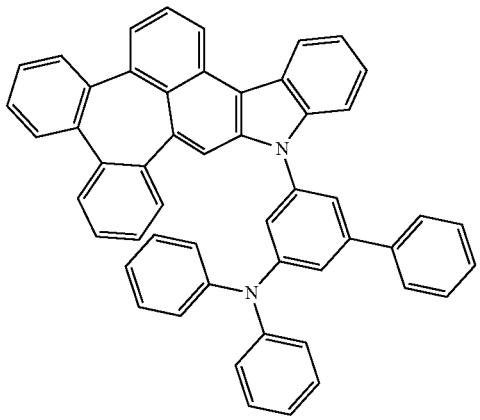
A-3
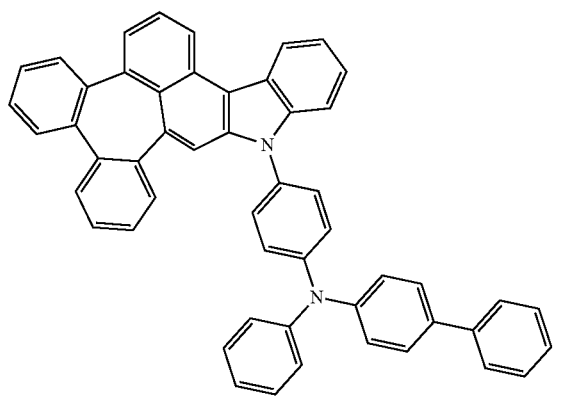
A-4
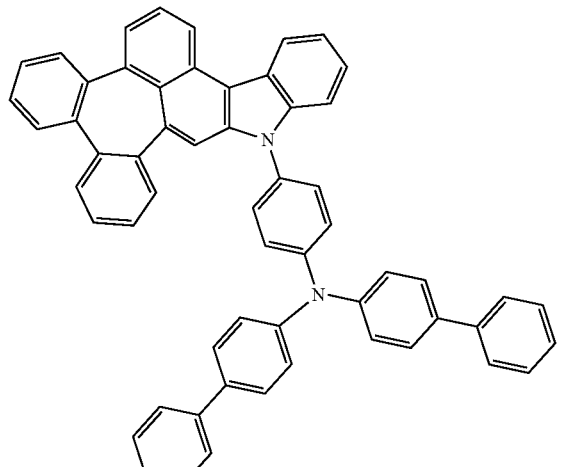
A-5
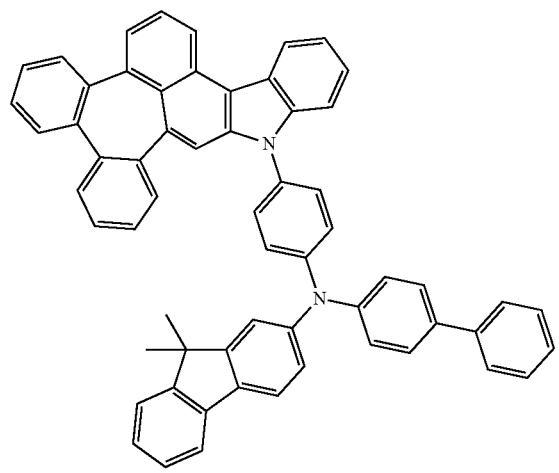
A-6

A-7
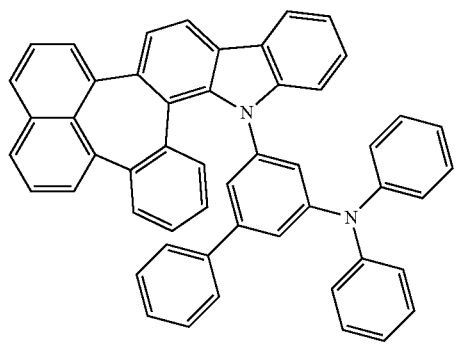
A-8
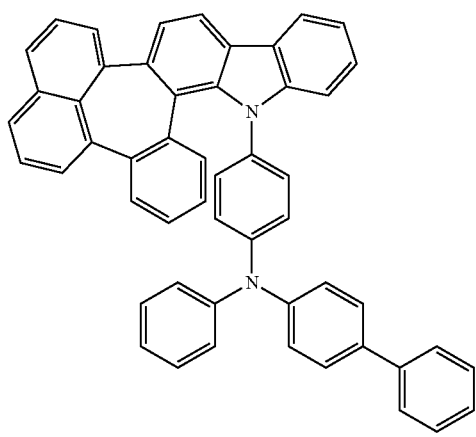
A-9
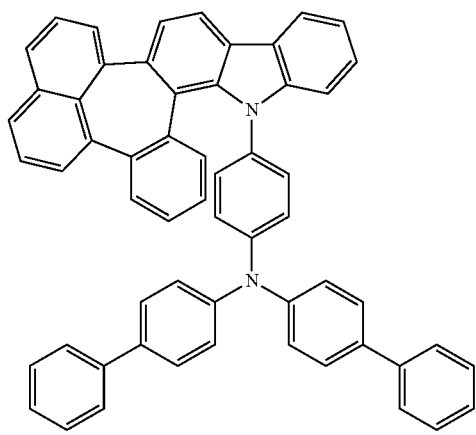
A-10
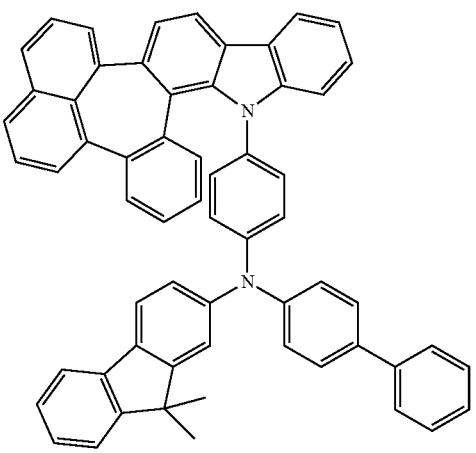
A-11
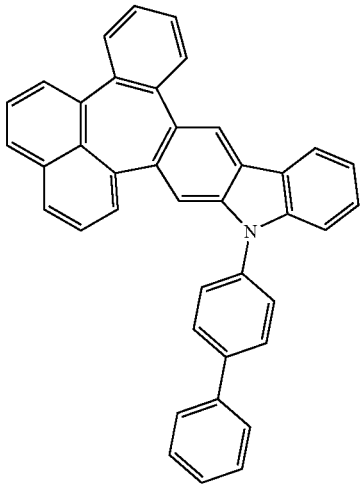
A-12
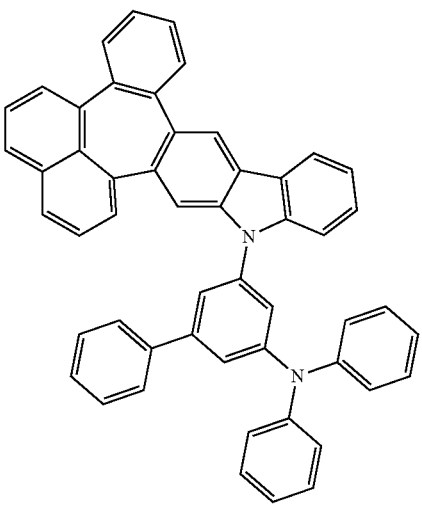
A-13
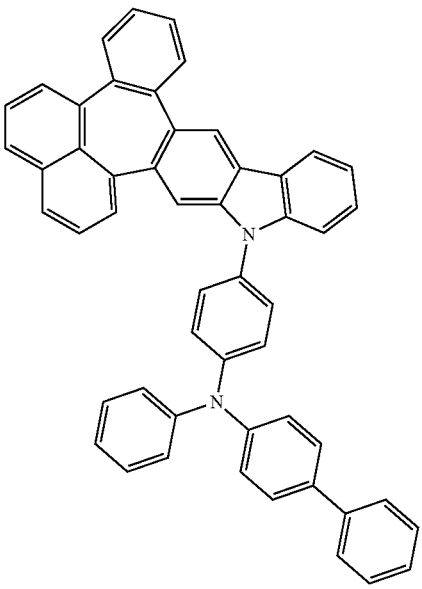

A-14 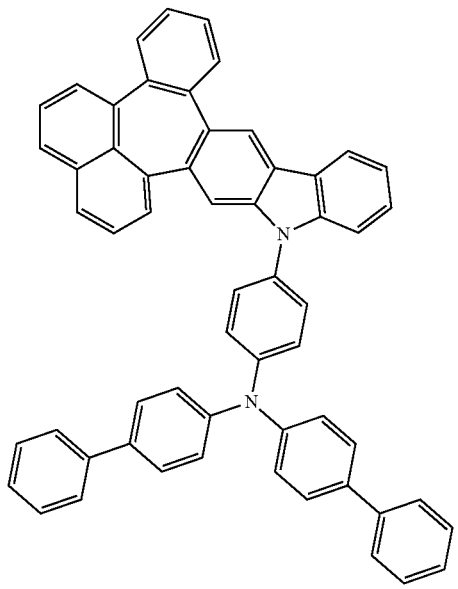
A-15 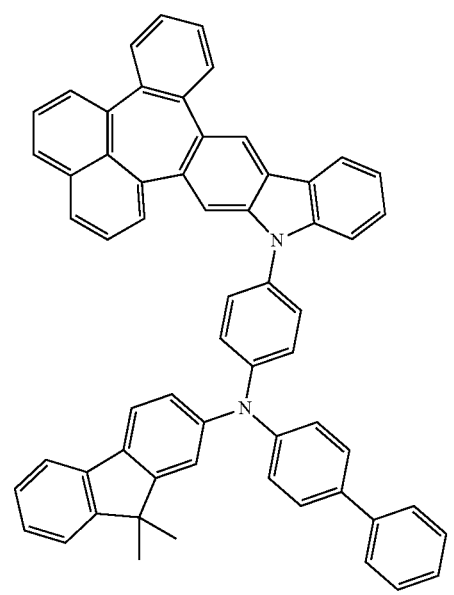
A-16
B-17 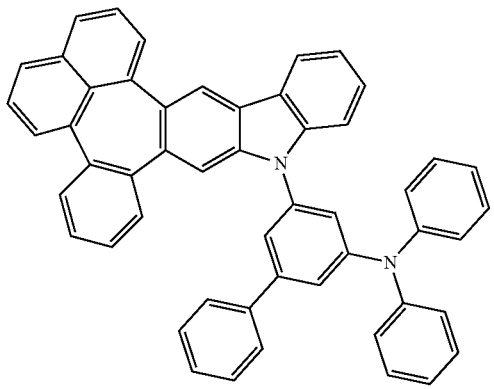
B-18 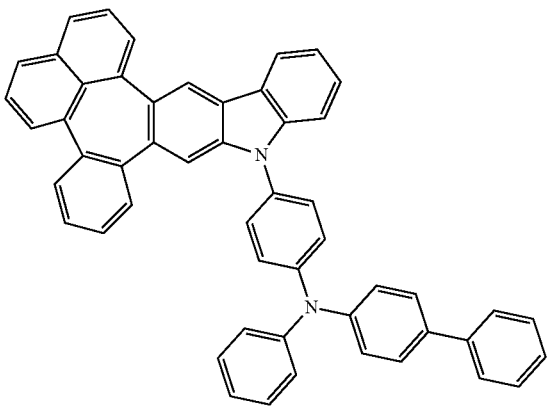
B-19 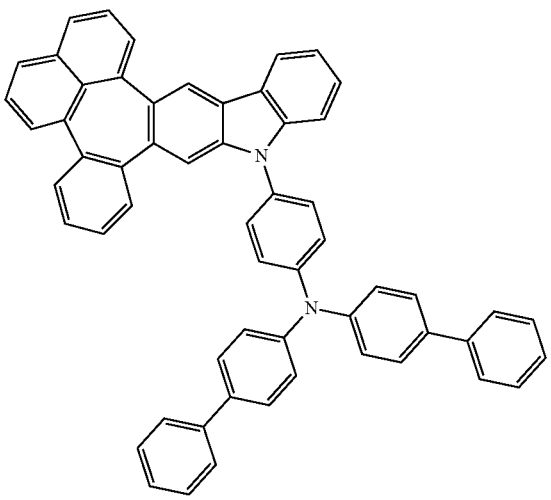

B-20
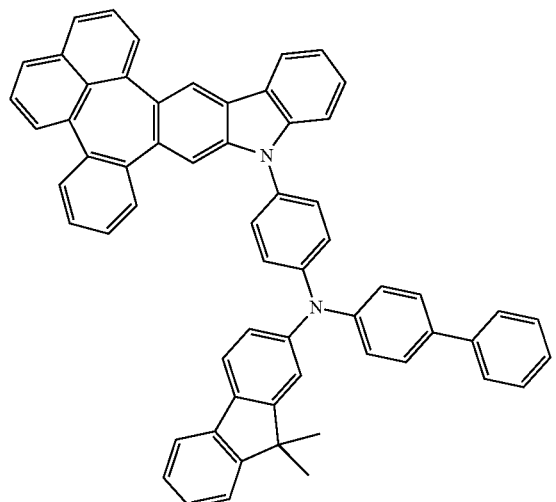
A-21
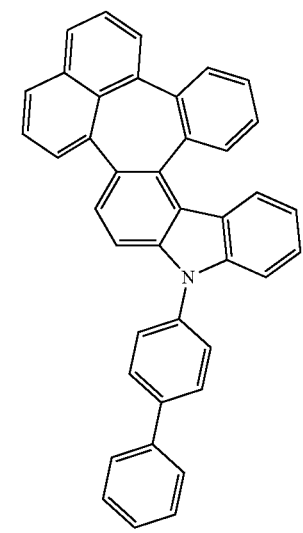
A-22
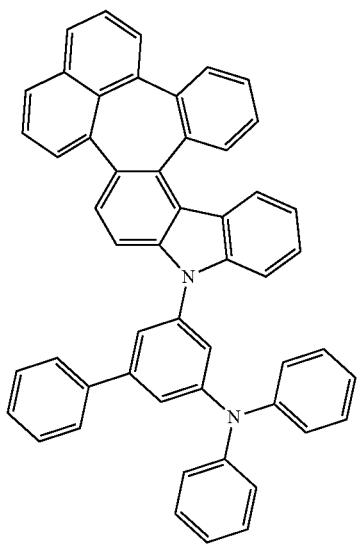
A-23
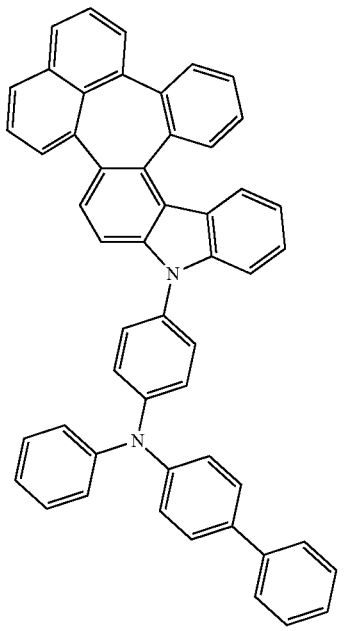
A-24
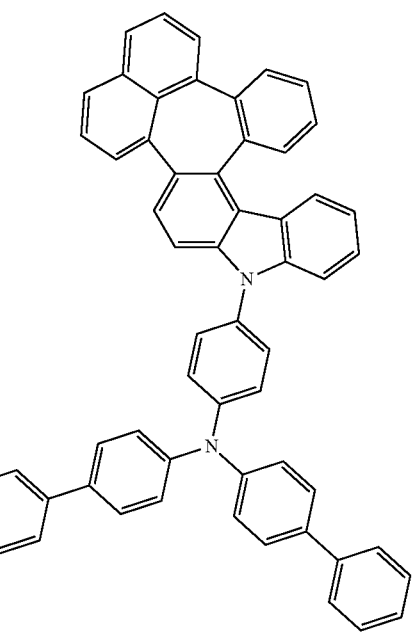

A-25
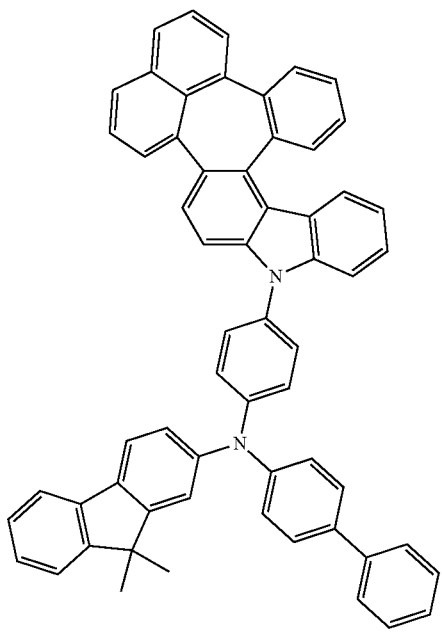
A-28
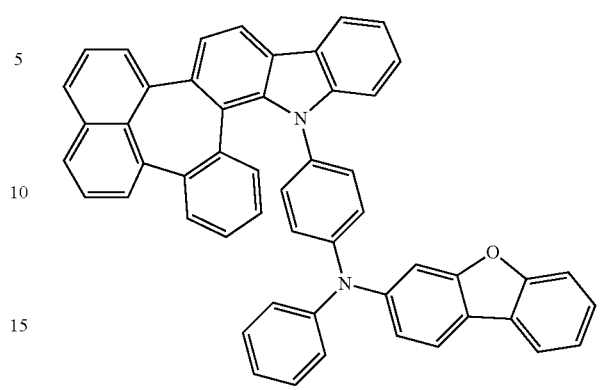
A-26
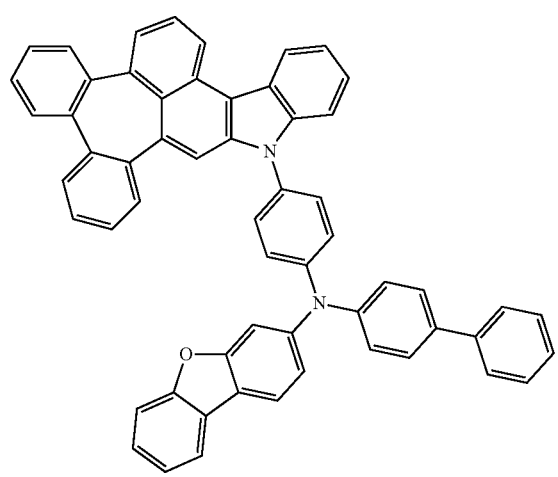
A-29
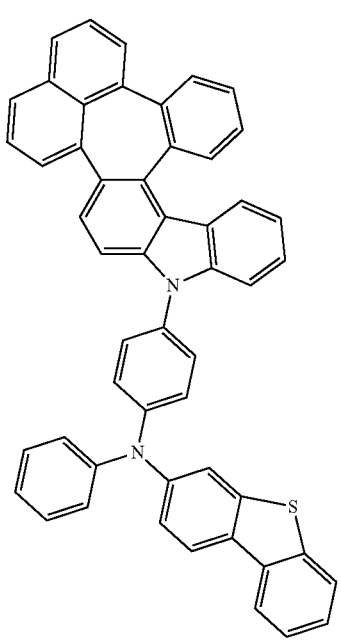
A-27
A-30
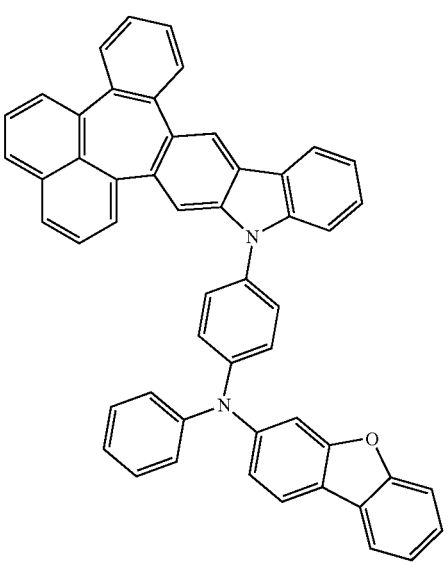

A-31
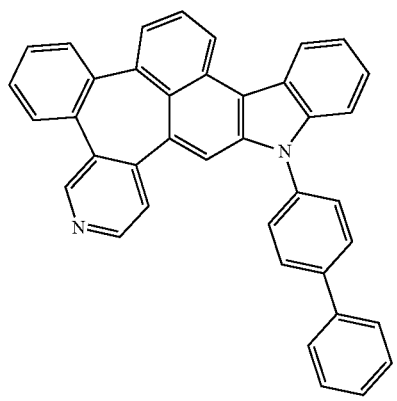
A-32
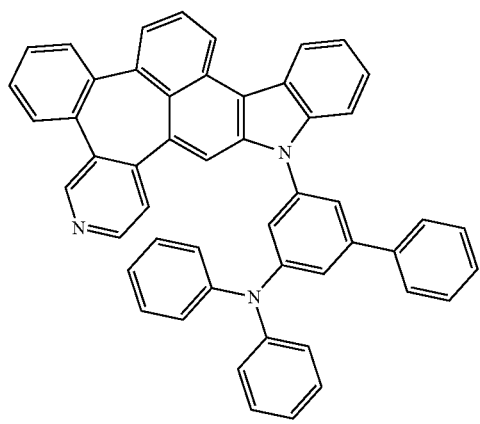
A-33
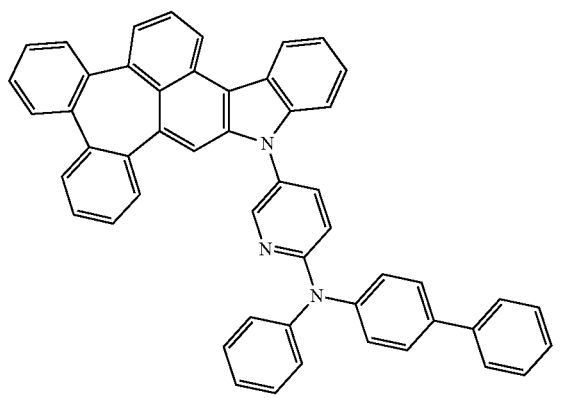
A-34
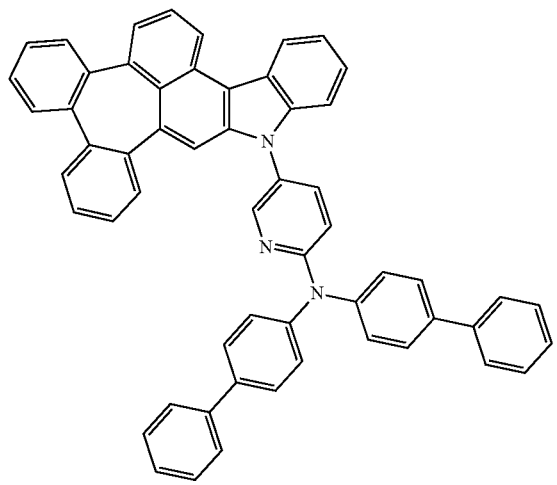
A-35
A-36
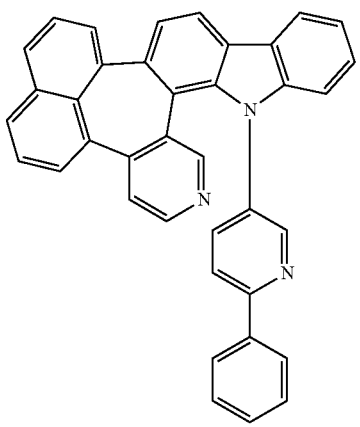

A-37
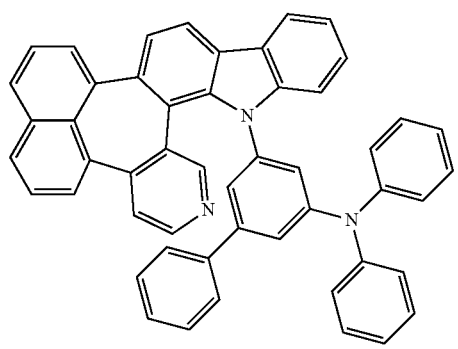
A-38
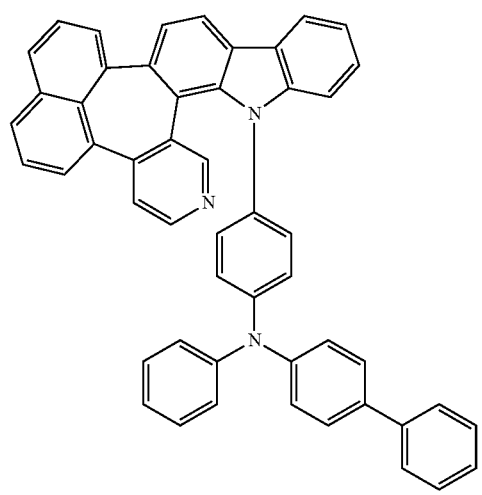
A-39
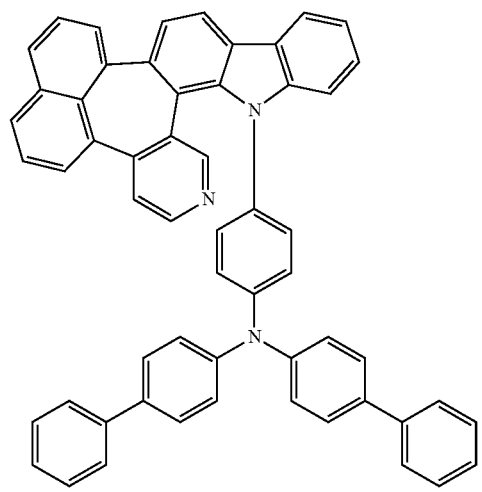
A-40
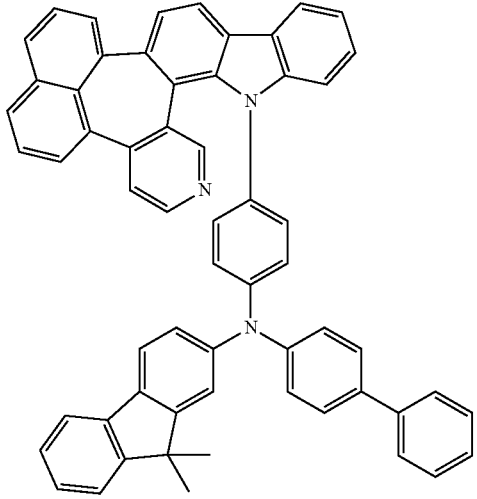
A-41
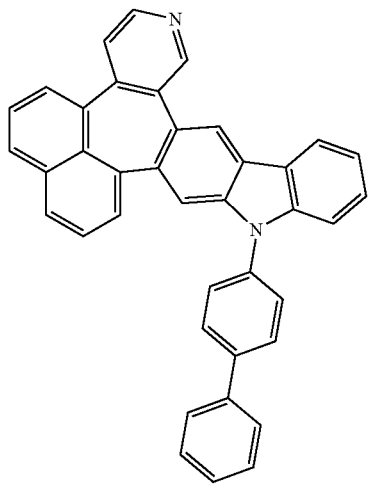
A-42
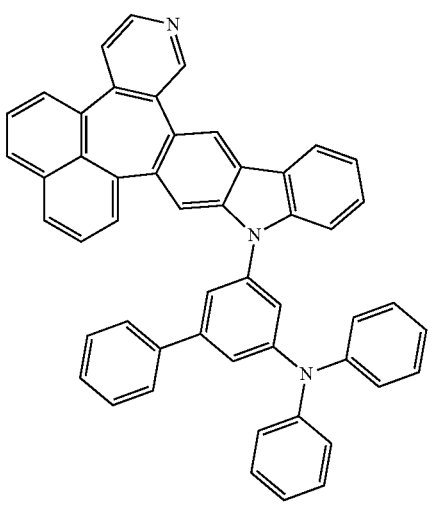

A-43
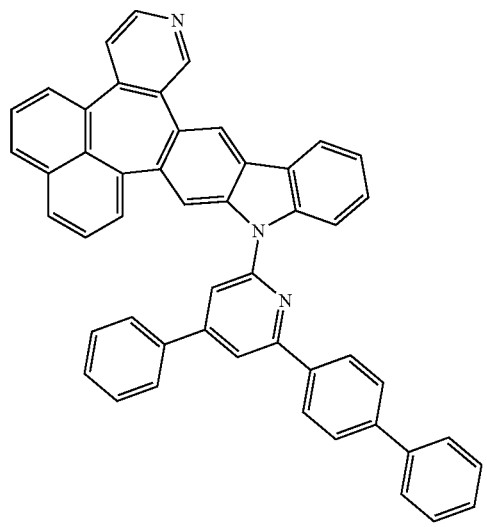
A-44
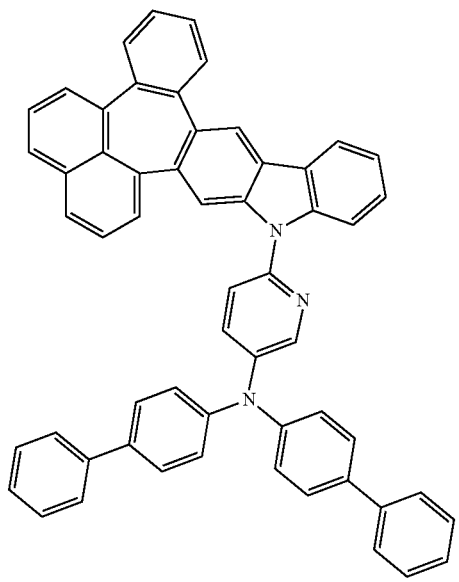
A-45
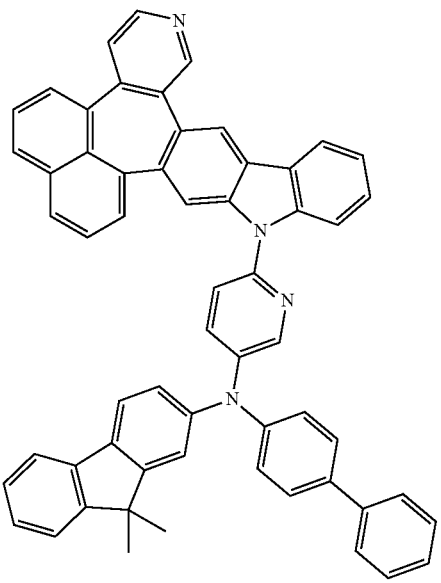
A-46
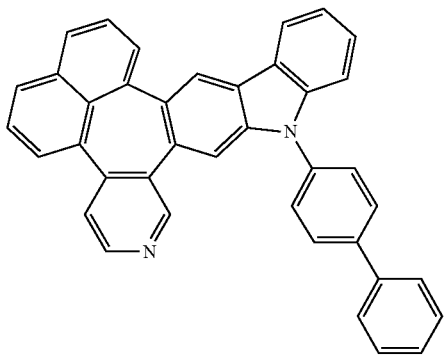
A-47
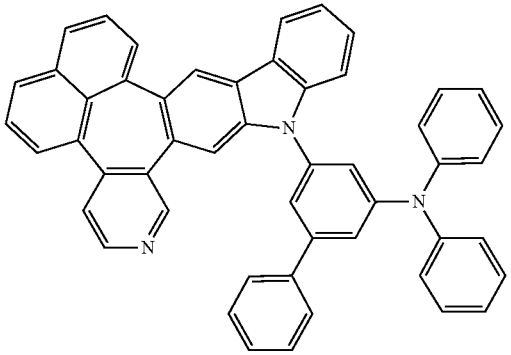

A-48
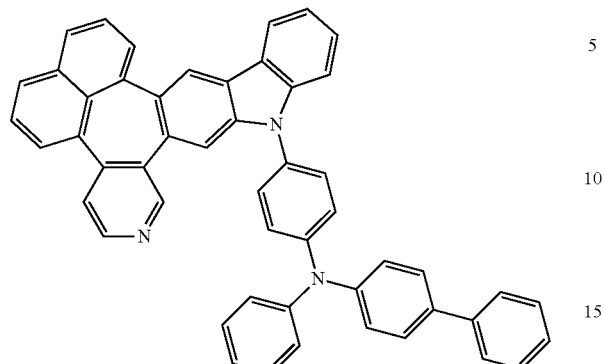
A-49
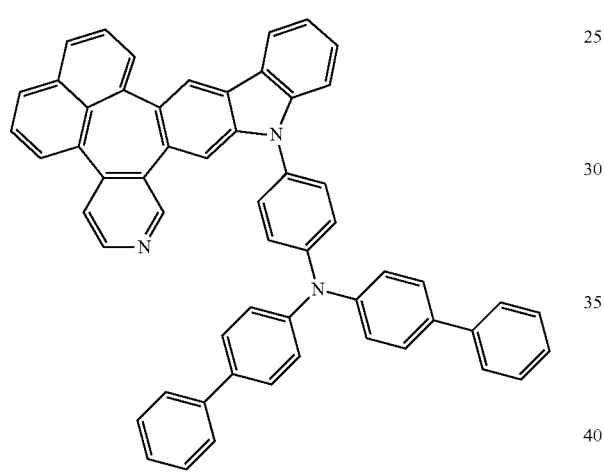
A-50
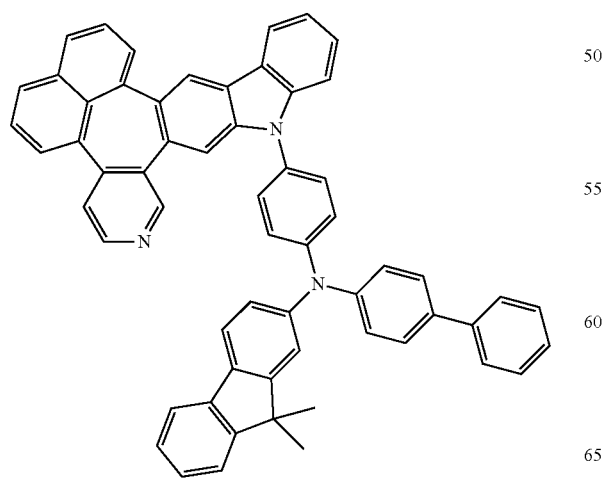
A-51
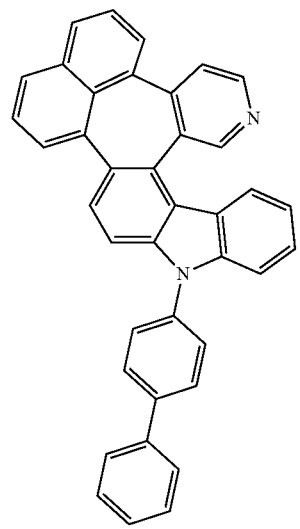
A-52
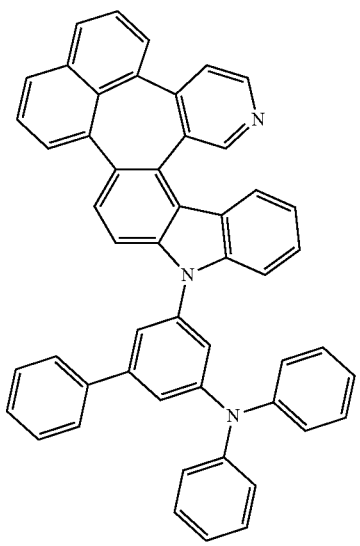

A-53
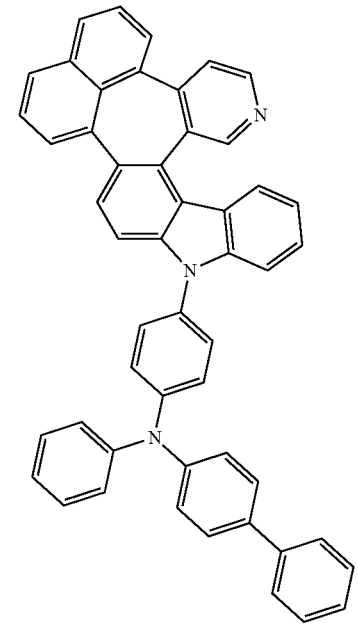
A-54
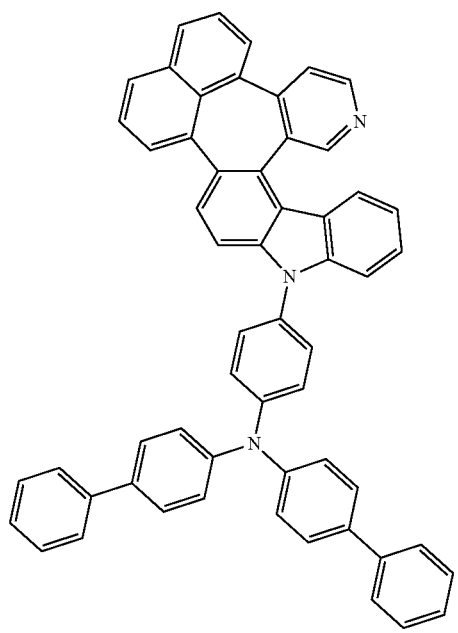
A-55
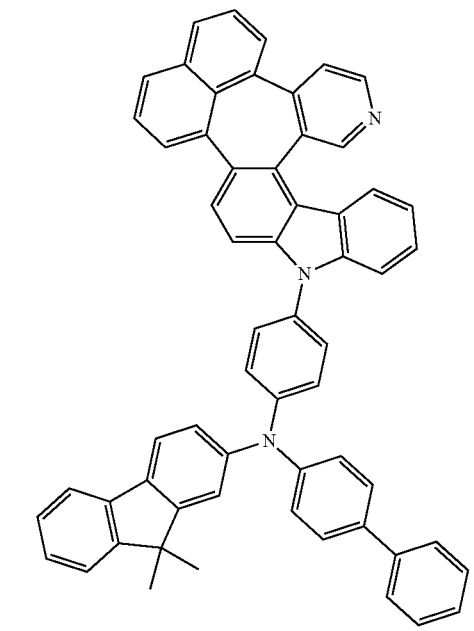
A-56
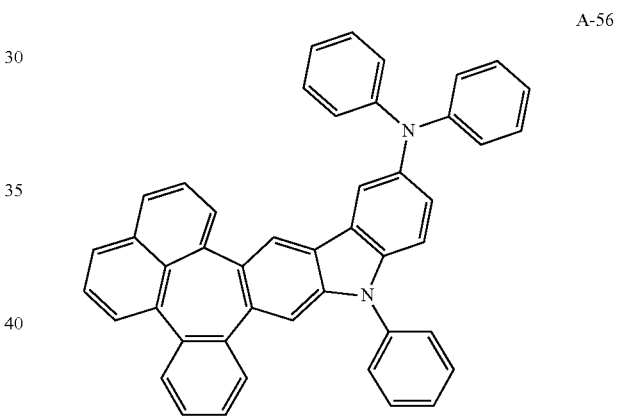
A-57
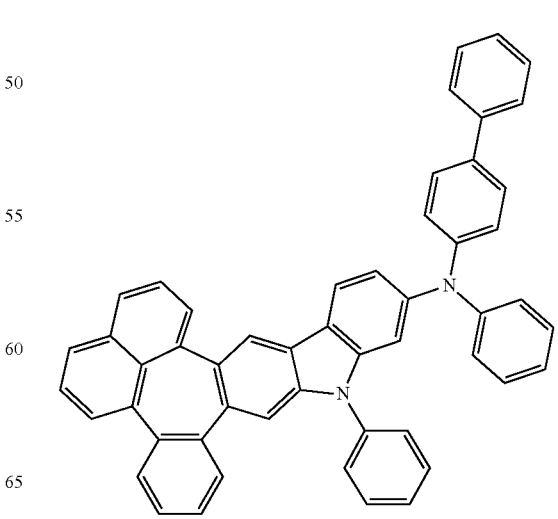

A-58
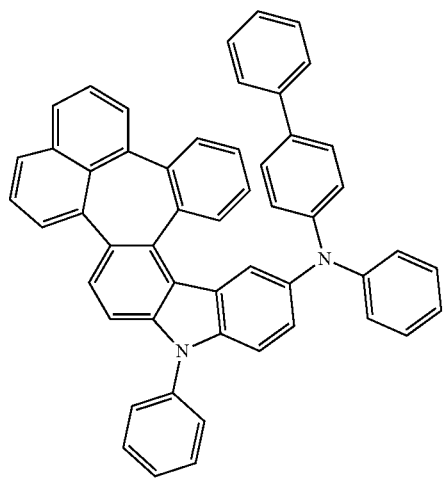
A-59
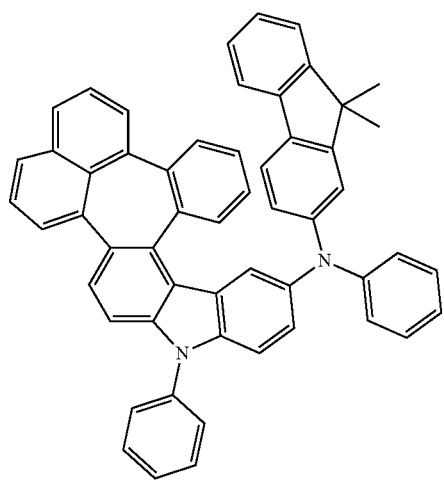
A-60
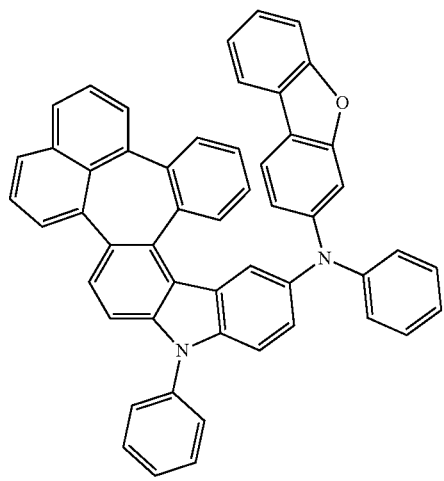
A-61
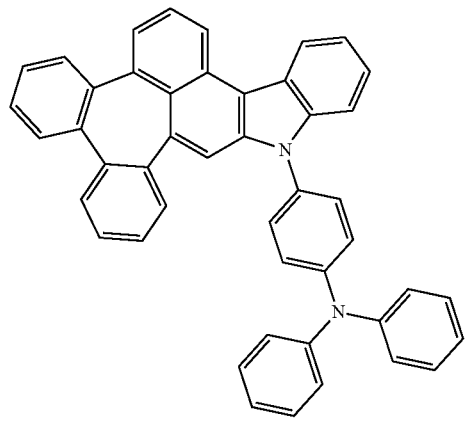
A-62
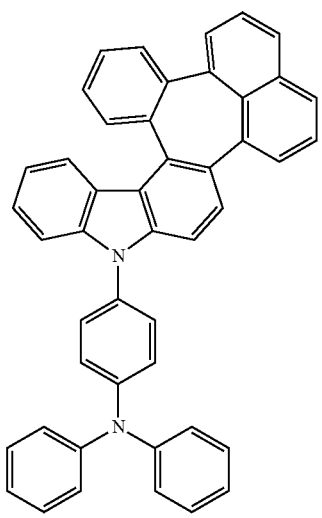
A-63
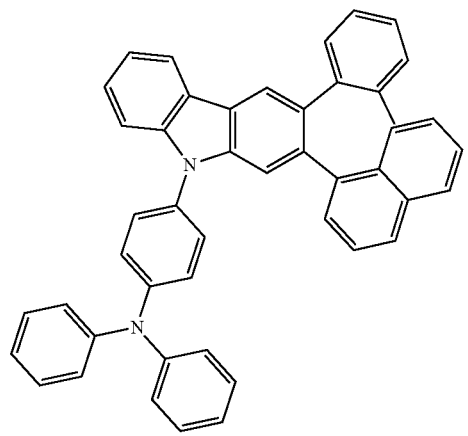

A-64
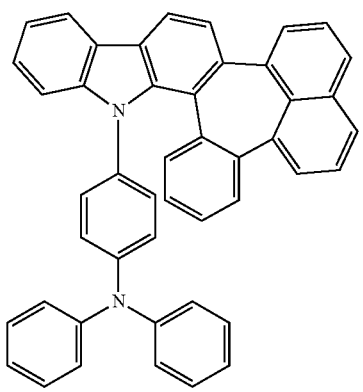
A-65
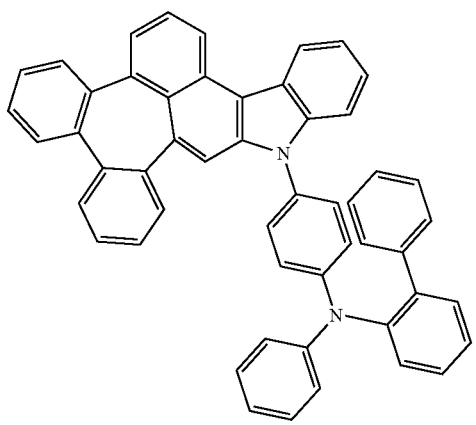
B-1
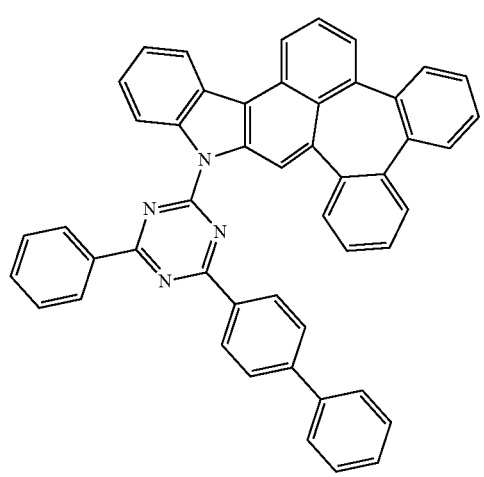
B-2
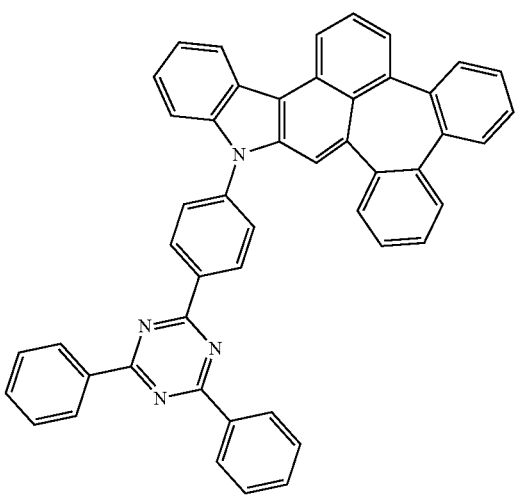
B-3
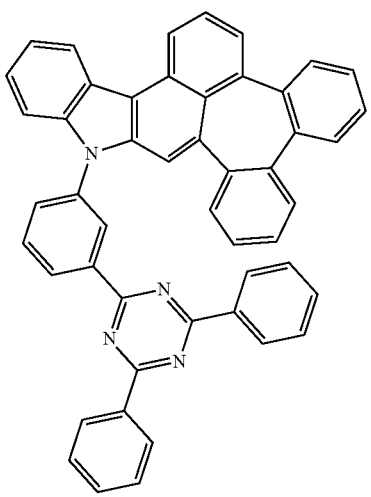
B-4

B-5
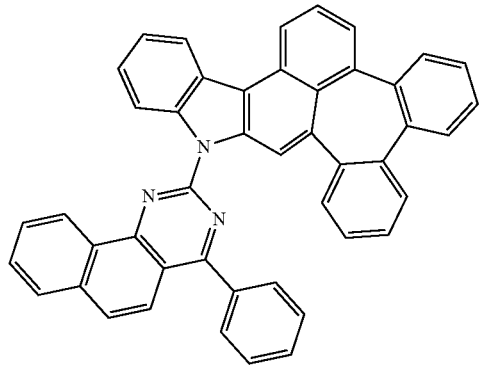
B-6
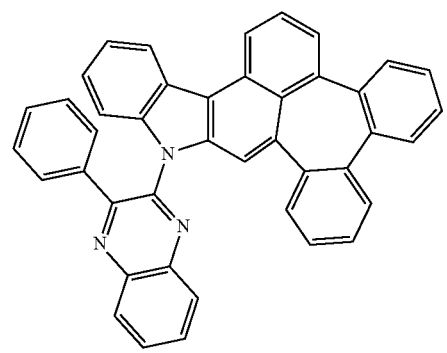
B-7
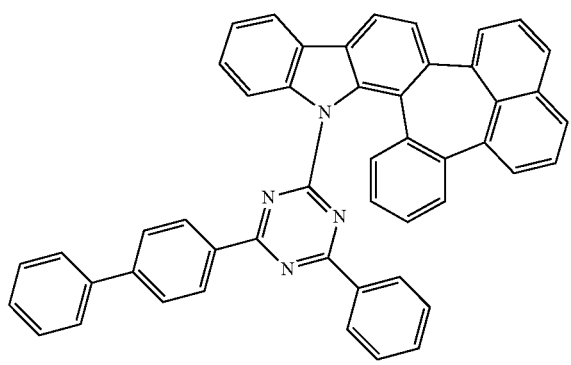
B-8
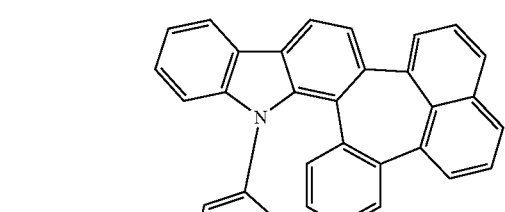
B-9
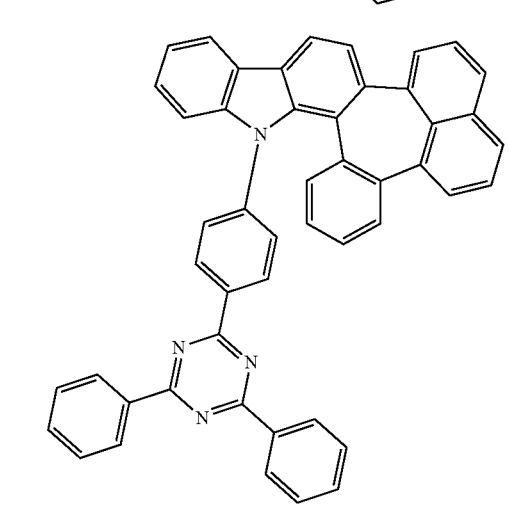
B-10
B-11
B-12

B-13
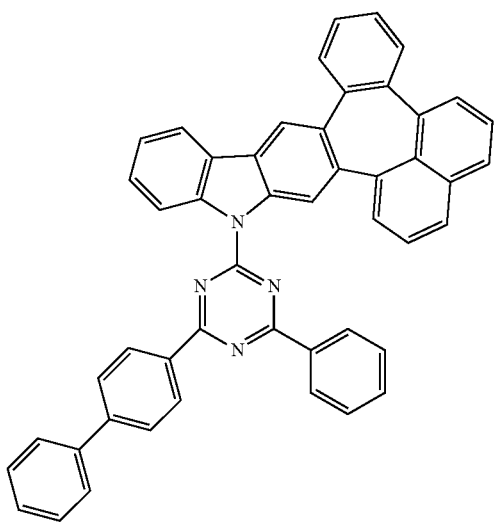
B-14
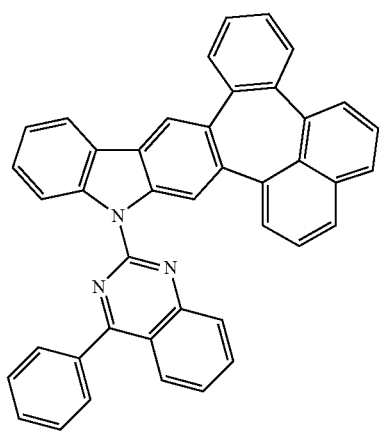
B-15
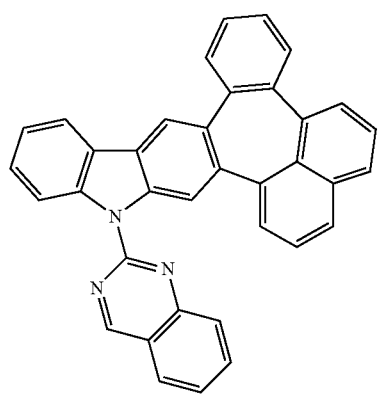
B-16
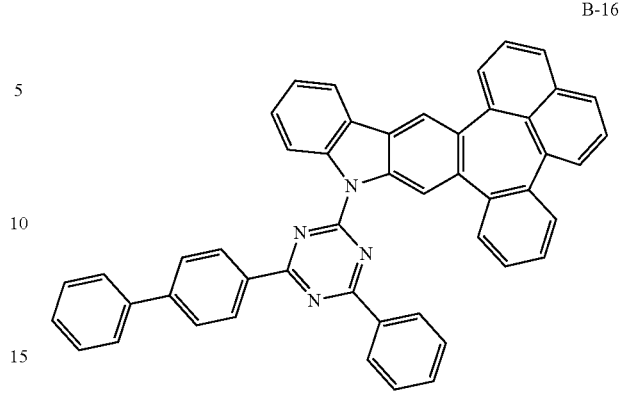
B-17
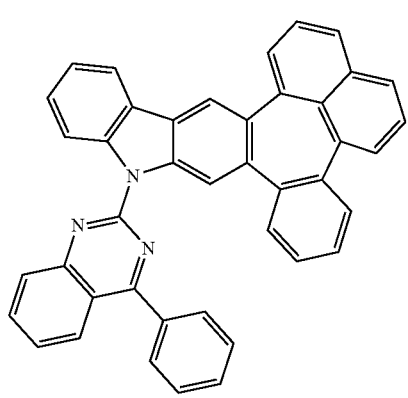
B-18
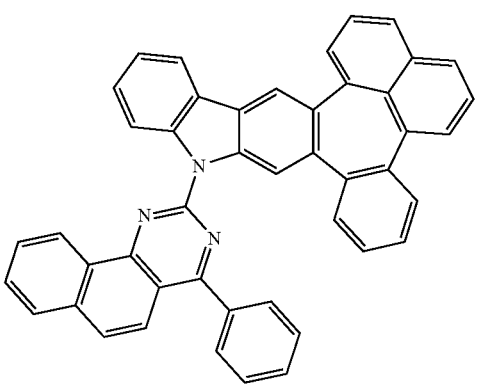
B-19
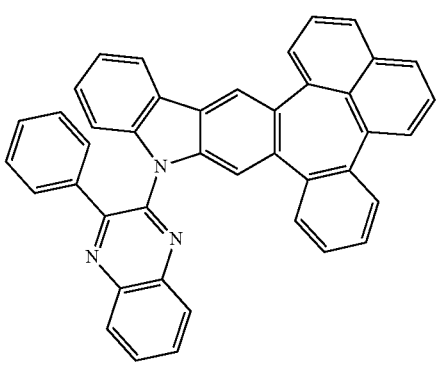

B-20
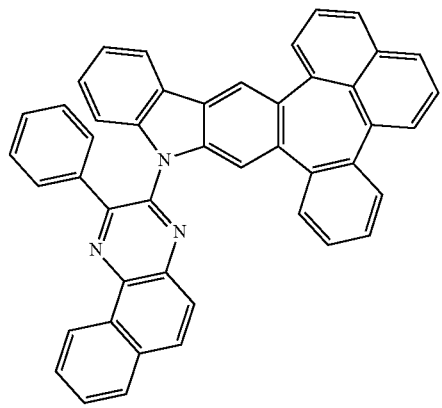
B-21
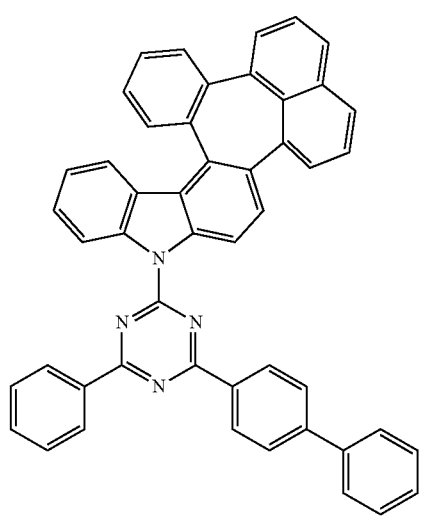
B-22
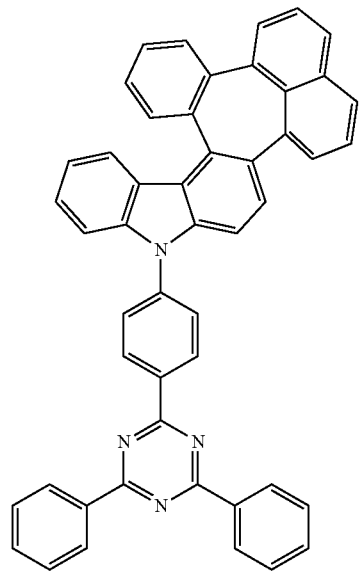
B-23
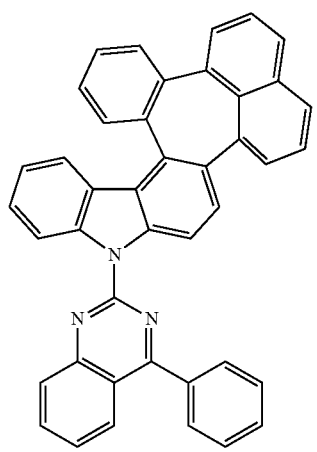
B-24
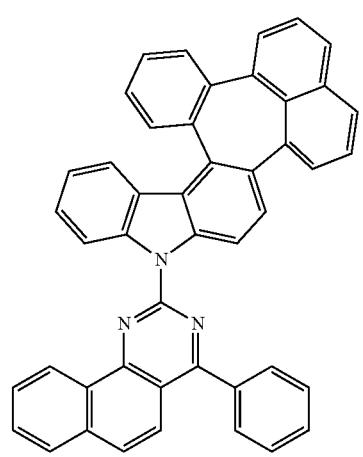
B-25
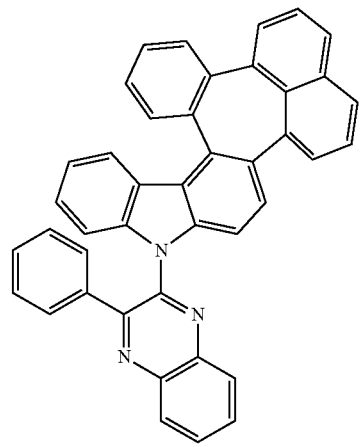

B-26
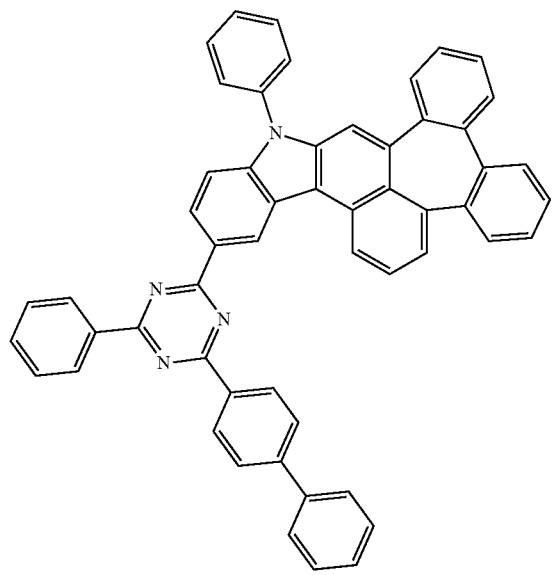
B-27
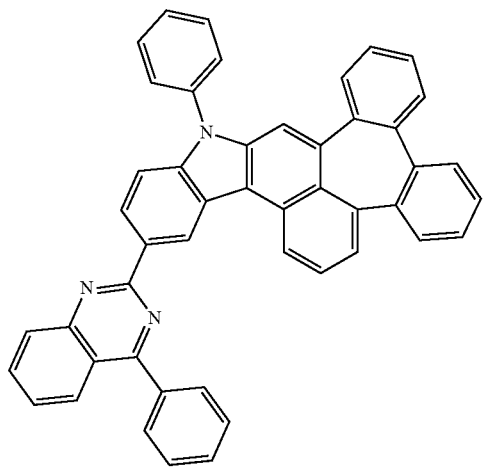
B-28
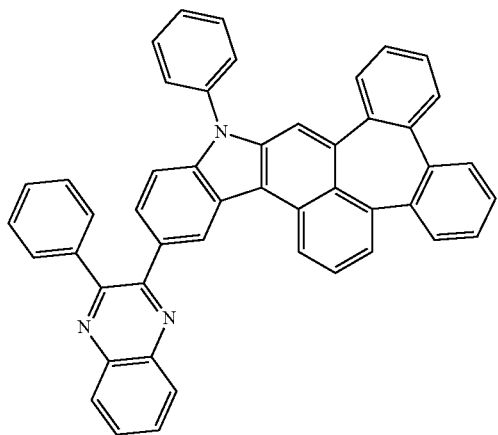
B-29
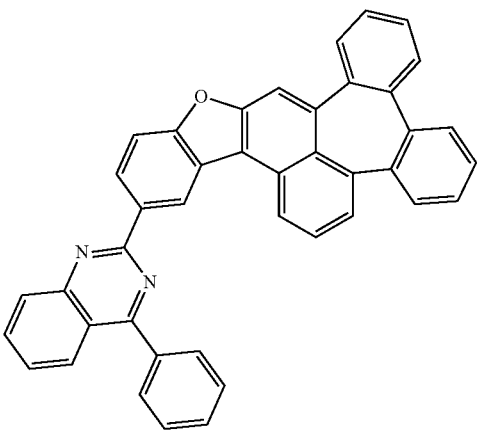
B-30
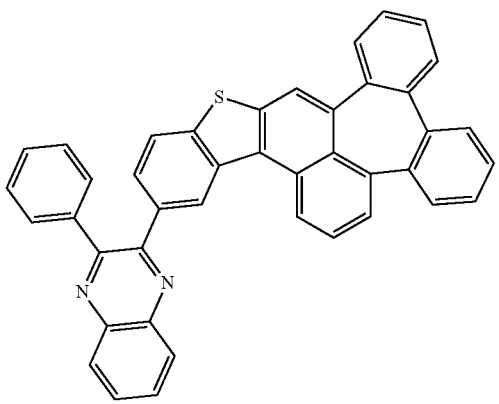
B-31
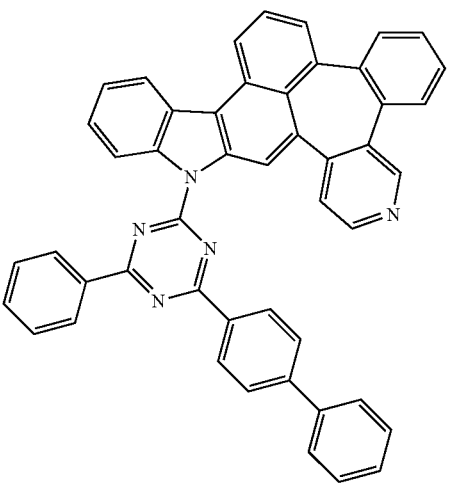

B-32
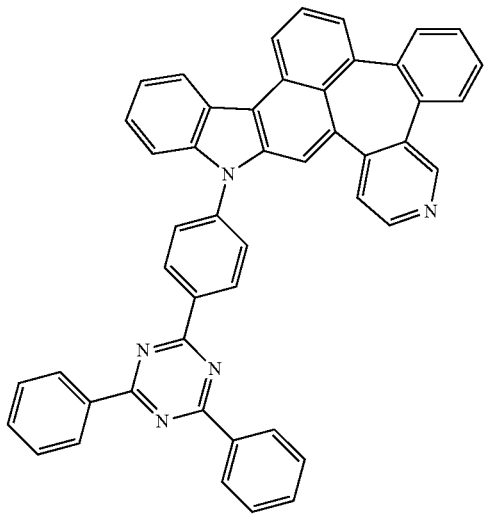
B-33
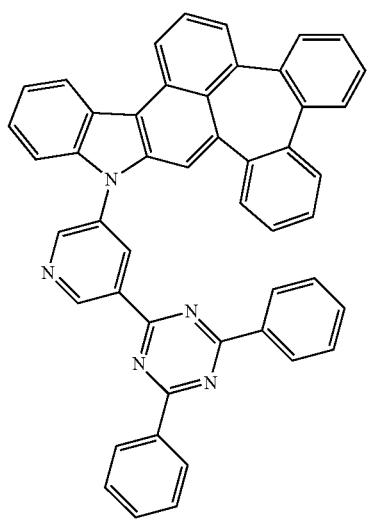
B-34
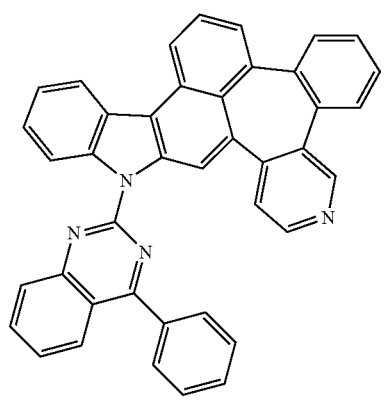
B-35
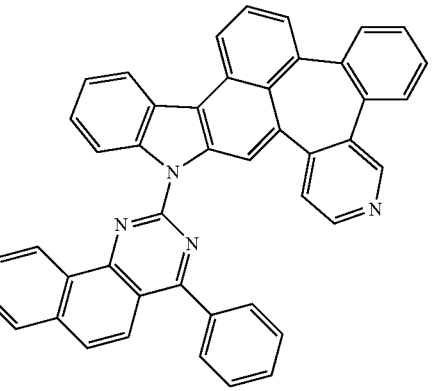
B-36
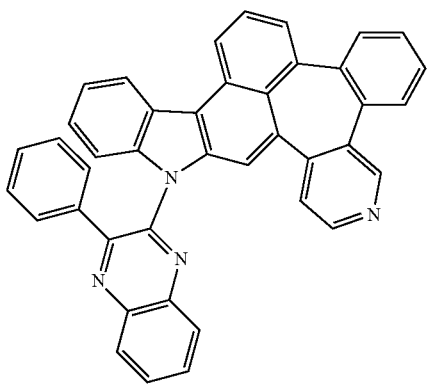
B-37
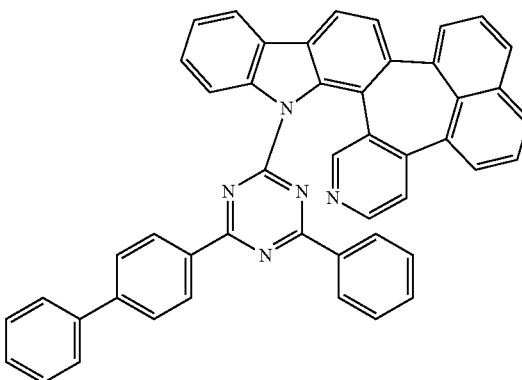
B-38
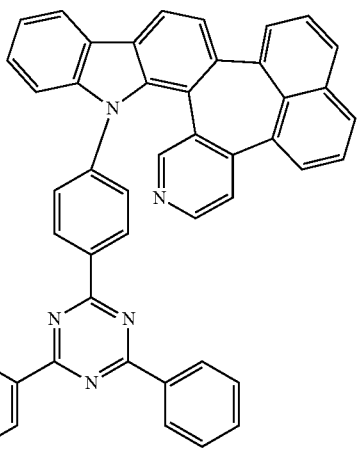

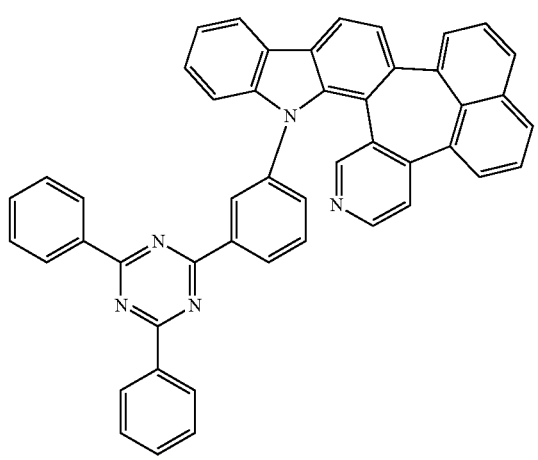
B-39
B-40
B-41
B-42
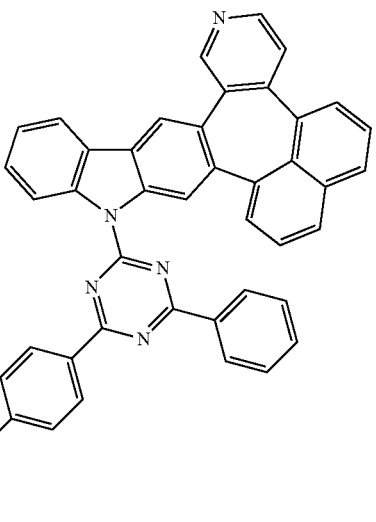
B-43
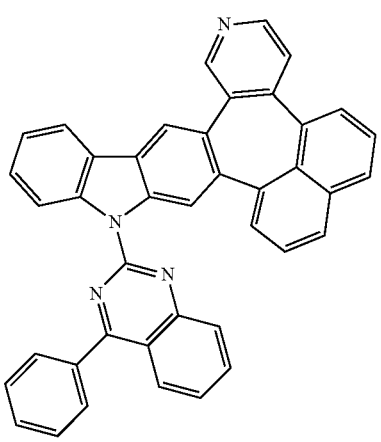
B-44
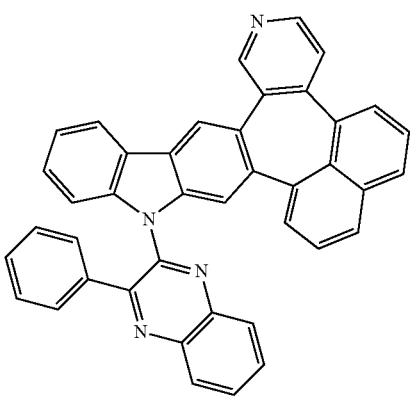
B-45

-continued
B-46
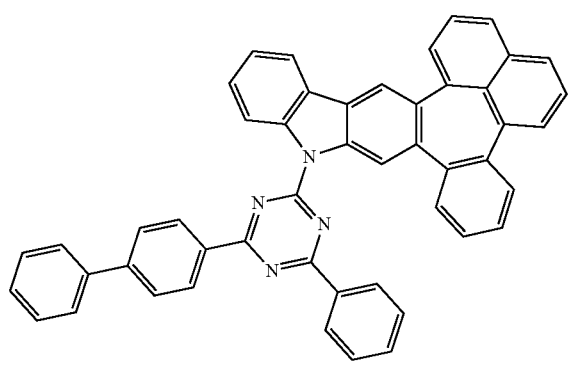
B-47
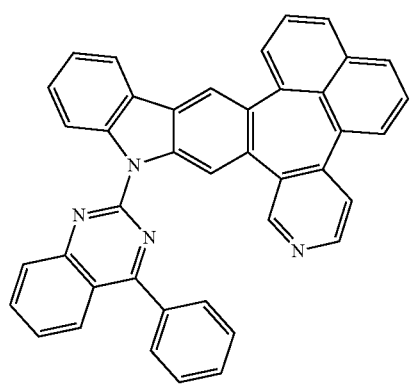
B-48
B-49
-continued
B-50
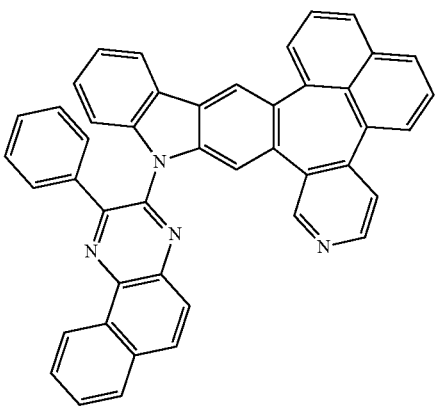
B-51
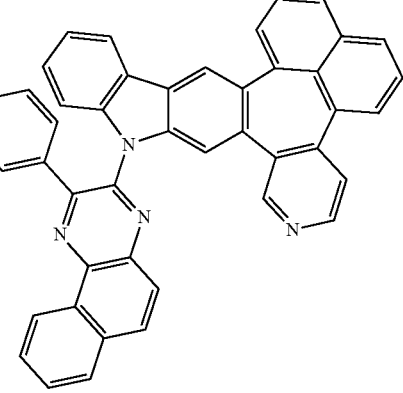
B-52
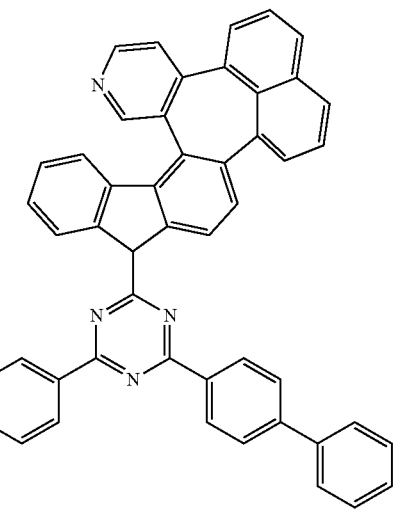

-continued
B-53
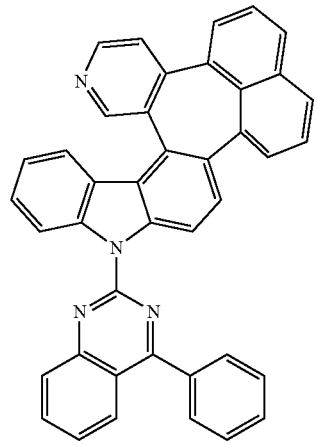
B-54
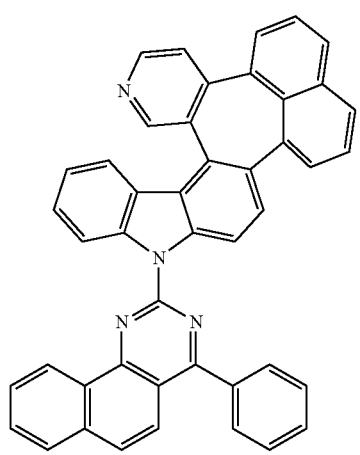
B-55
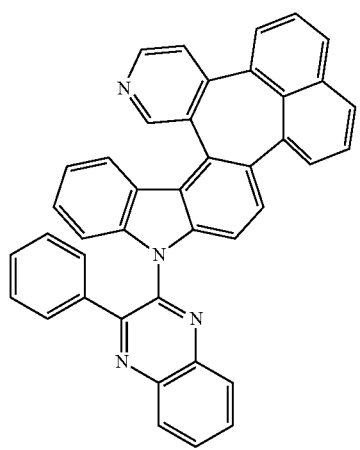
-continued
B-56
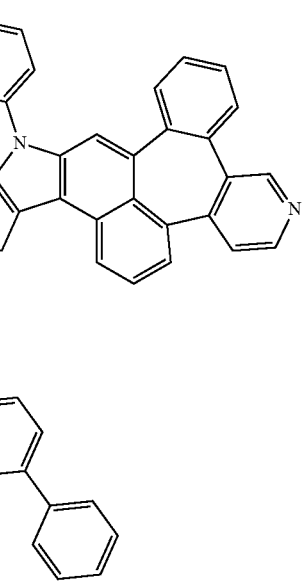
B-57
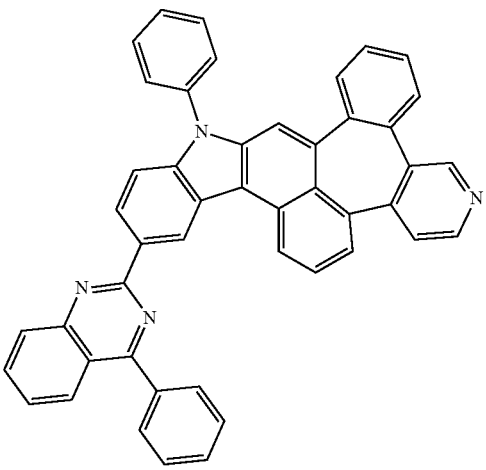
B-58
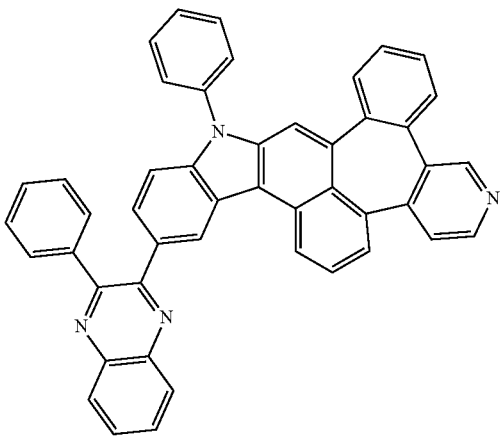

-continued
B-59
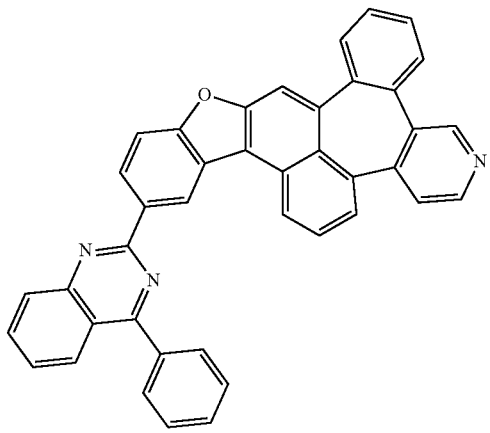
B-60
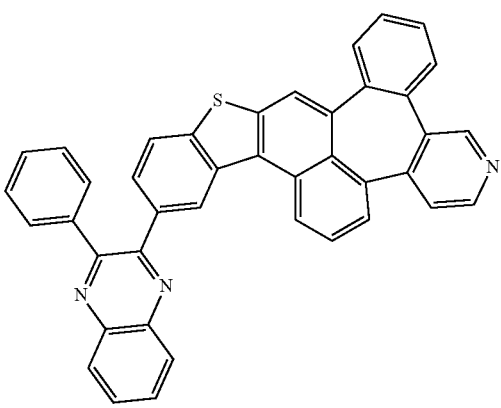
B-61
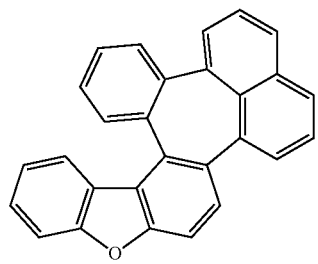
B-62
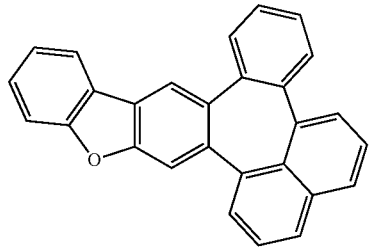
B-63
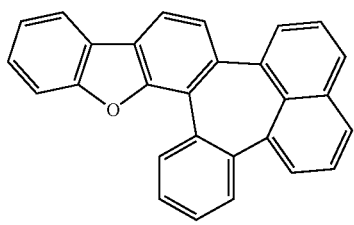
B-64
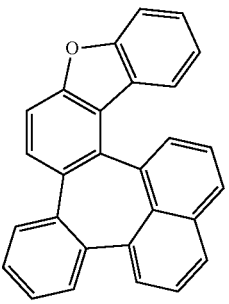
B-65
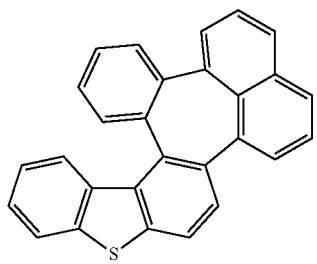
B-66
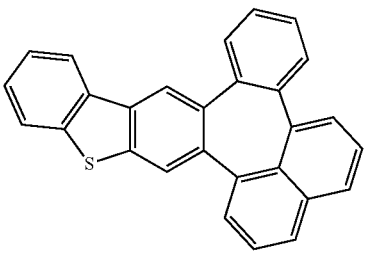
B-67
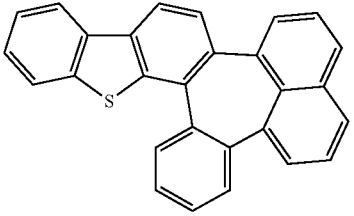
B-68
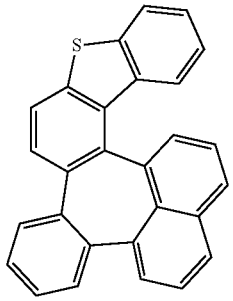
The compound of formula 1 according to the present disclosure can be prepared by a synthetic method known to a person skilled in the art. For example, it can be prepared according to the following reaction schemes, but is not limited thereto.

[Reaction Scheme 1]

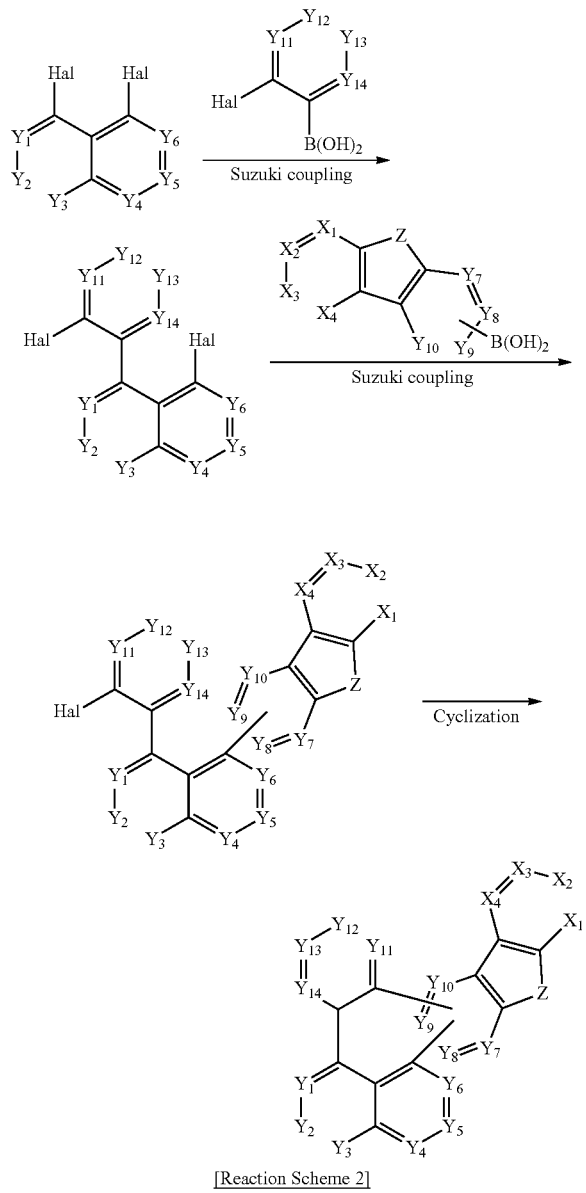

[Reaction Scheme 2]

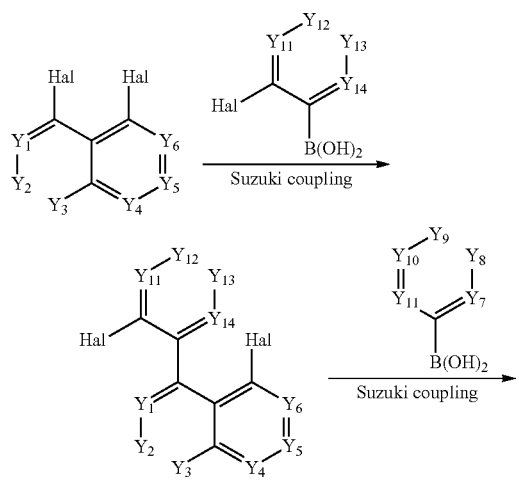

-continued

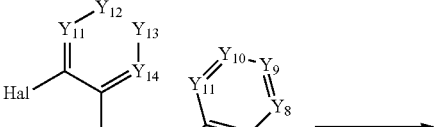
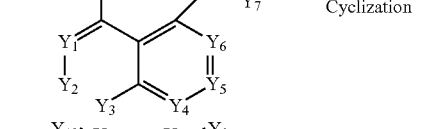
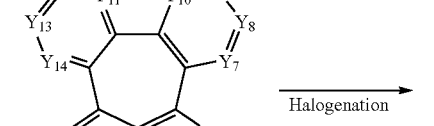
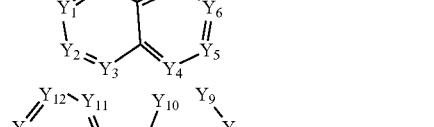
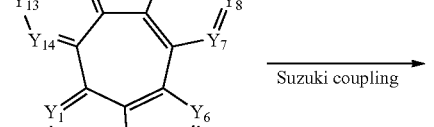
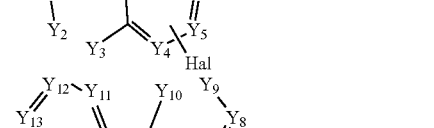
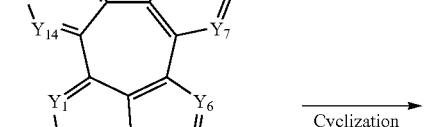
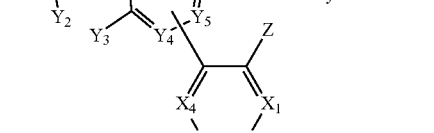
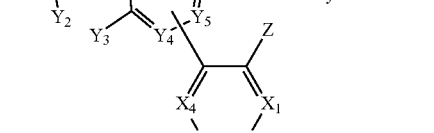
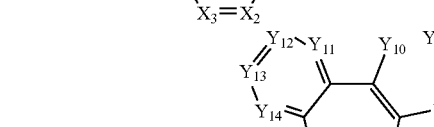
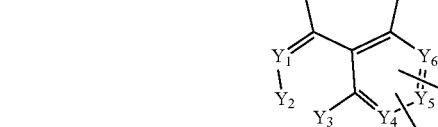

In the reaction schemes, $Y_1$ to $Y_{14}$, Z, and $X_1$ to $X_4$ are as defined in formula 1, and Hal represents a halogen.

Although illustrative synthesis examples of the compound represented by formula 1 were described above, a person skilled in the art will be able to readily understand that all of them are based on a Buchwald-Hartwig cross-coupling reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, and a Phosphine-mediated reductive cyclization reaction, and the above reactions proceed even when substituents, which are defined in formula 1 above, but are not specified in the specific synthesis examples, are bonded.

The hole transport zone of the present disclosure can comprise at least one layer selected from the group consisting of a hole transport layer, a hole injection layer, an electron blocking layer, and a hole auxiliary layer, and each of said layers can be composed of at least one layer.

In one embodiment of the present disclosure, the hole transport zone comprises a hole transport layer. Also, the hole transport zone comprises a hole transport layer, and can further comprise at least one of a hole injection layer, an electron blocking layer, and a hole auxiliary layer.

In addition, the present disclosure provides an organic electroluminescent material comprising the organic electroluminescent compound of formula 1, and an organic electroluminescent device comprising the material.

The above material can be a host material of a light-emitting layer, or a hole transport material, a hole auxiliary material, or a light-emitting auxiliary material, specifically, a hole transport material, a hole auxiliary material, or a light-emitting auxiliary material of a red light-emitting organic electroluminescent device. If there are two or more hole transport layers, the above material can be a hole transport material (hole auxiliary material) comprised in a hole transport layer adjacent to the light-emitting layer.

The above material can be comprised of the organic electroluminescent compound of the present disclosure alone, or can further include conventional materials generally used in organic electroluminescent materials. If at least two materials are included in one layer, they can be mixed and deposited to form a layer, or separately and simultaneously co-deposited to form a layer.

The organic electroluminescent compound of formula 1 of the present disclosure can be comprised in one or more layers of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer; and preferably in at least one of the light-emitting layer, the hole transport layer, the hole auxiliary layer, or the light-emitting auxiliary layer. If there are two or more hole transport layers, the organic electroluminescent compound of formula 1 of the present disclosure can be used in at least one of the hole transport layers. For example, where used in the hole transport layer, the organic electroluminescent compound of the present disclosure can be comprised as a hole transport material.

When used in the light-emitting layer, the organic electroluminescent compound of formula 1 of the present disclosure can be comprised as a host material. Preferably, the light-emitting layer can further comprise one or more dopants. If necessary, the organic electroluminescent compound of the present disclosure can be used as a co-host material. That is, the light-emitting layer can additionally comprise an organic electroluminescent compound other than the organic electroluminescent compound of formula 1 of the present disclosure (first host material) as a second host material. Herein, the weight ratio of the first host material to the second host material is in the range of 1:99 to 99:1.

The dopant comprised in the organic electroluminescent device according to the present disclosure may be at least one phosphorescent or fluorescent dopant, preferably at least one phosphorescent dopant. The phosphorescent dopant materials applied to the organic electroluminescent device according to the present disclosure are not particularly limited, but may be selected from metallated complex compounds of iridium (Ir), osmium (Os), copper (Cu), and platinum (Pt), may be preferably selected from ortho-metallated complex compounds of iridium (Ir), osmium (Os), copper (Cu), and platinum (Pt), and may be more preferably an ortho-metallated iridium complex compound.

The organic electroluminescent device according to the present disclosure comprises a first electrode; a second electrode; and at least one organic layer between the first and second electrodes.

One of the first and second electrodes may be an anode, and the other may be a cathode. The organic layer comprises a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Herein, the second electrode may be a transflective electrode or a reflective electrode, and may be a top emission, bottom emission, or both-sides emission type according to the material used. In addition, the hole injection layer may be further doped with a p-dopant, and the electron injection layer may be further doped with an n-dopant.

The organic layer may further comprise at least one compound selected from the group consisting of arylamine-based compounds and styrylarylamine-based compounds.

In addition, in the organic electroluminescent device according to the present disclosure, the organic layer may further comprise at least one metal selected from the group consisting of metals of Group 1, metals of Group 2, transition metals of the 4th period, transition metals of the 5th period, lanthanides and organic metals of d-transition elements of the Periodic Table, or at least one complex compound comprising said metal.

In addition, the organic electroluminescent device according to the present disclosure may emit white light by further comprising at least one light-emitting layer which comprises a blue electroluminescent compound, a red electroluminescent compound or a green electroluminescent compound known in the field, besides the compound according to the present disclosure. Also, if necessary, a yellow or orange light-emitting layer can be further comprised in the device.

In addition, the organic electroluminescent compound according to the present disclosure can also be used in an organic electroluminescent device comprising Quantum Dot (QD).

In the organic electroluminescent device according to the present disclosure, at least one layer (hereinafter, "a surface layer") is preferably placed on an inner surface(s) of one or both electrode(s); selected from a chalcogenide layer, a metal halide layer, and a metal oxide layer. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, said chalcogenide includes $SiO_x$ ($1 \leq X \leq 2$), $AlO_x$ ($1 \leq X \leq 1.5$), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The hole auxiliary layer or the light-emitting auxiliary layer is placed between the hole transport layer and the light-emitting layer, and can be used in order to control the hole transport rate. The hole auxiliary layer or the light-emitting auxiliary layer can provide an effect of improving the efficiency and lifespan of an organic electroluminescent device.

In addition, the light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of an organic electroluminescent device.

The electron transport zone means an area in which electrons move between the light-emitting layer and the cathode, and may comprise, for example, at least one of a hole blocking layer, an electron transport layer, an electron buffer layer, and an electron injection layer. The hole blocking layer, the electron transport layer, the electron buffer layer, and the electron injection layer may be a single layer, or a multi-layer in which two or more layers are stacked.

In one embodiment of the present disclosure, the organic electroluminescent device of the present disclosure may further comprise an azine-based compound, in addition to the organic electroluminescent compound of the present disclosure, as at least one of an electron transport material, an electron injection material, an electron buffer material, and a hole blocking material.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic electroluminescent device having two or more light-emitting layers which emits white light.

In order to form each layer constituting the organic electroluminescent device of the present disclosure, dry film-forming methods such as vacuum deposition, sputtering, plasma, ion plating methods, etc., or wet film-forming methods such as spin coating, dip coating, flow coating methods, etc., can be used. When forming the film of the first and second host compounds of the present disclosure, a co-evaporation or a mixed evaporation method is used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a film.

By using the organic electroluminescent device of the present disclosure, a display device, for example, for smartphones, tablets, notebooks, PCs, TVs, or vehicles, or a lighting device, for example, an indoor or outdoor lighting device, can be produced.

Hereinafter, the preparation method of the compounds of the present disclosure and the physical properties of the compounds will be explained in detail with reference to the representative compounds of the present disclosure. However, the present disclosure is not limited to the Examples below.

Example 1: Preparation of Compound B-10

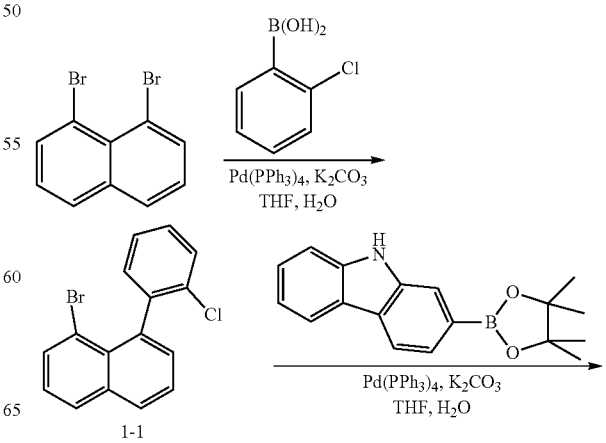

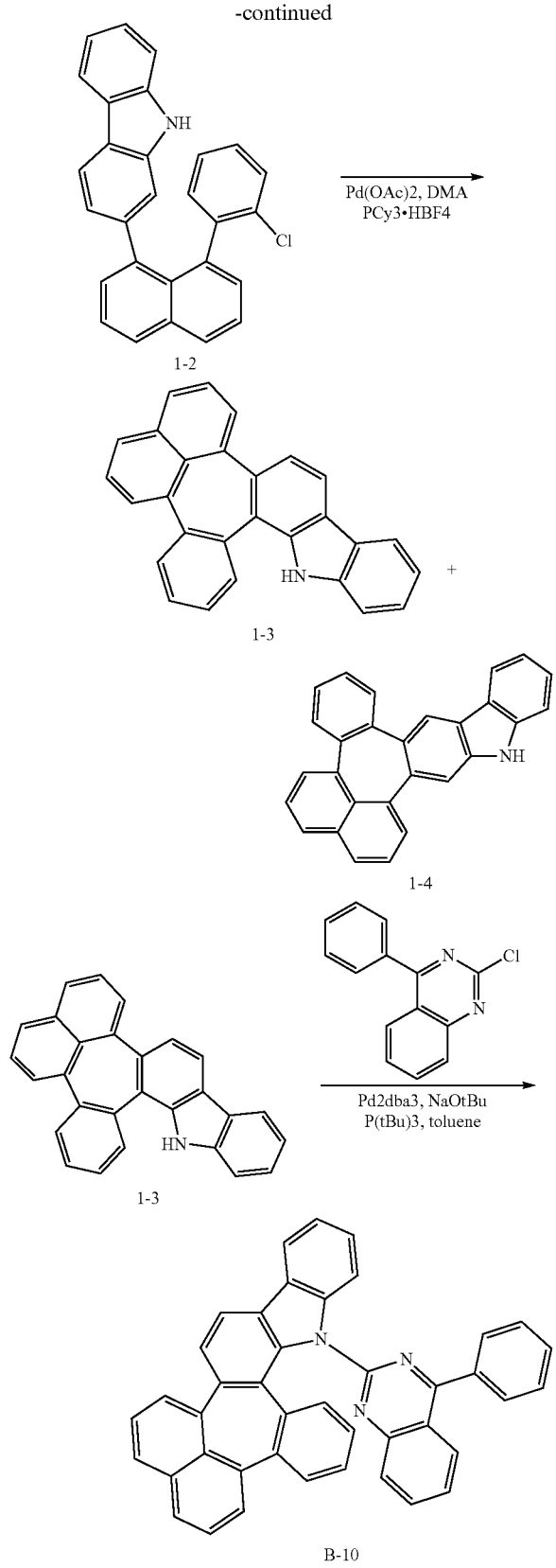

20.2 g of tetrakis(triphenylphosphine)palladium(0) (Pd(PPh$_3$)$_4$) (17.5 mmol), and 120.8 g of potassium carbonate (874.5 mmol) were dissolved in 1500 mL of tetrahydrofuran (THF) and 400 mL of distilled water, and the mixture was refluxed at 100° C. for 18 hours. After completion of the reaction, an organic layer was extracted with ethyl acetate, and the residual moisture was removed using magnesium sulfate. Thereafter, the resulting product was dried and separated by column chromatography to obtain 78 g of compound 1-1 (yield: 70%).

Preparation of Compound 1-2

In a flask, 10 g of compound 1-1 (31 mmol), 11.1 g of 2-(4,4,5,5-tetramethyl-1,3,2-dioxylboren-2-yl)-9H-carbazole (38 mmol), 1.8 g of tetrakis(triphenylphosphine)palladium(0) (Pd(PPh$_3$)$_4$) (1.55 mmol), and 10.9 g of potassium carbonate (79 mmol) were dissolved in 160 mL of tetrahydrofuran (THF) and 40 mL of distilled water, and the mixture was refluxed at 100° C. for 18 hours. After completion of the reaction, an organic layer was extracted with ethyl acetate, and the residual moisture was removed using magnesium sulfate. Thereafter, the resulting product was dried and separated by column chromatography to obtain 8 g of compound 1-2 (yield: 63%).

Preparation of Compound 1-3 and Compound of 1-4

In a flask, 26 g of compound 1-2 (64 mmol), 2.9 g of Pd(OAc)$_2$ (13 mmol), 7.1 g of ligand(tricyclohexylphosphonium tetrafluoroborate) (19 mmol) and 62.9 g of Cs$_2$CO$_3$ (193 mmol) were dissolved in 322 mL of dimethyl acetamide (DMA), and stirred for 6 hours under reflux. The mixture was cooled to room temperature, and distilled water was added thereto. An organic layer was extracted with ethyl acetate, and dried with magnesium sulfate. Thereafter, the resulting product was distilled under reduced pressure and separated by column chromatography to obtain 17 g of compound 1-3 (yield: 72%) and 3.2 g of compound 1-4 (yield: 14%).

Preparation of Compound B-10

7.0 g of compound 1-3 (19 mmol), 4.6 g of 2-chloro-4-phenylquinazoline (19 mmol), 0.87 g of tris(dibenzylideneacetone)dipalladium(0) (0.95 mmol), 0.77 mL of tri-t-butylphosphine (1.9 mmol, 50% toluene solution), 3.6 g of sodium t-butoxide (38 mmol), and 190 mL of toluene were introduced into a flask and refluxed for 3 hours. The reaction solution was cooled to room temperature, and the solvent was removed by a rotary evaporator. Thereafter, the residue was purified by column chromatography to obtain 5.8 g of yellow solid compound B-10 (yield: 53%, melting point: 310° C., glass transition temperature: 169° C.).

Example 2: Preparation of Compound B-15

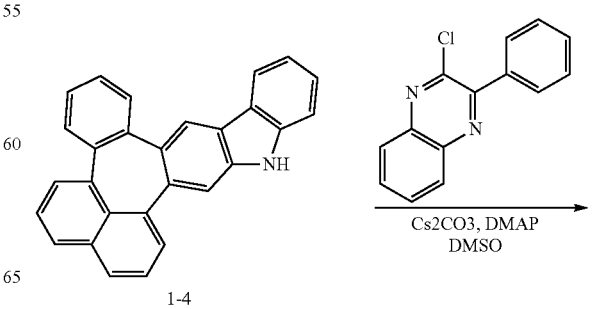

Preparation of Compound 1-1

In a flask, 100 g of 1,8-dibromonaphthalene (349.7 mmol), 82 g of (2-chlorophenyl)boronic acid (524.6 mmol), -continued

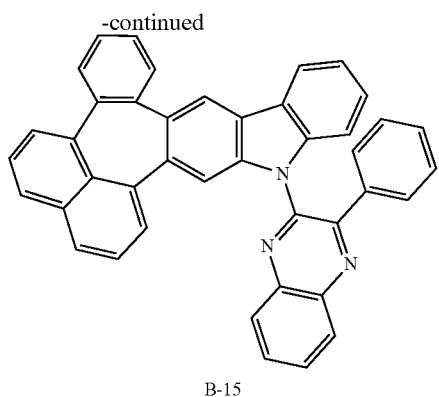

B-15

In a flask, 3.2 g of compound 1-4 (8.7 mmol), 2.5 g of 2-chloro-3-phenylquinoxaline (1.0 mmol), 5.7 g of cesium carbonate (17 mmol), and 0.53 g of 4-dimethylaminopyridine (DMAP) (4.4 mmol) were dissolved in 22 mL of dimethyl sulfoxide (DMSO), and the mixture was stirred at 100° C. for 4 hours. After completion of the reaction, the reaction solution was cooled to room temperature, and distilled water and methanol were added thereto. The solvent was removed using a filter, and the resulting solid was separated by column chromatography to obtain 2.5 g of compound B-15 (yield: 50%, melting point: 215° C., glass transition temperature: 170° C.).

Example 3: Preparation of Compound A-9

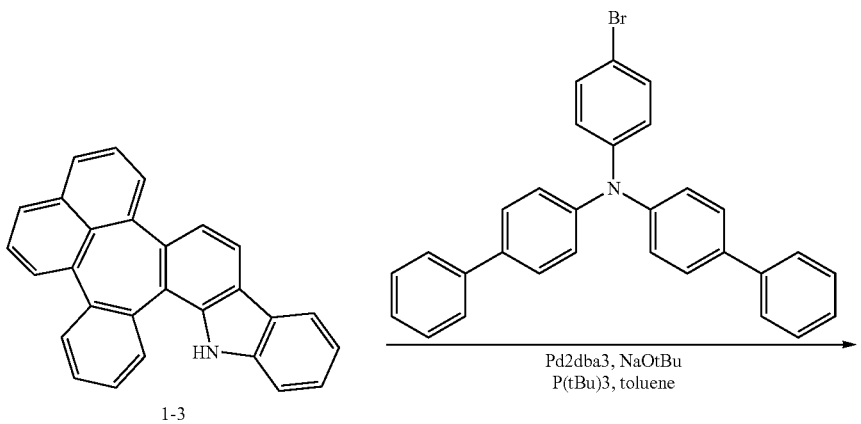

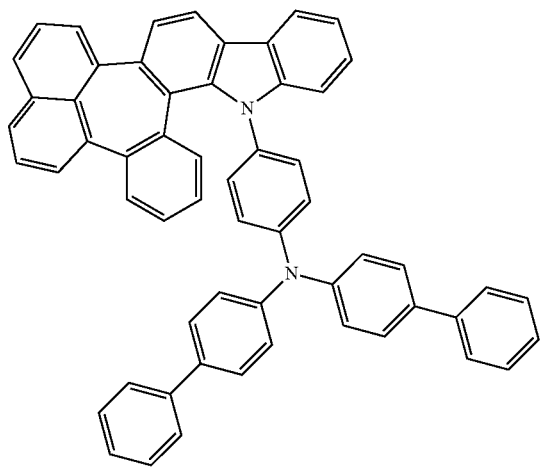

A-9

4.1 g of compound 1-3 (11 mmol), 5.3 g of N-(1,1'-biphenyl-4-yl)-N-(4-bromophenyl)-[1,1'-biphenyl]-4-amine (11 mmol), 0.51 g of tris(dibenzylideneacetone)dipalladium (0.55 mmol), 0.45 mL of tri-t-butylphosphine (1.1 mmol, 50% toluene solution), 2.1 g of sodium t-butoxide (22 mmol), and 111 mL of toluene were introduced into a flask and refluxed for 4 hours. The reaction solution was cooled to room temperature, and the solvent was removed by a rotary evaporator. Thereafter, the residue was purified by column chromatography to obtain 3.9 g of white solid compound A-9 (yield: 46%, melting point: 216° C., glass transition temperature: 176° C.).

Example 4: Preparation of Compound B-1

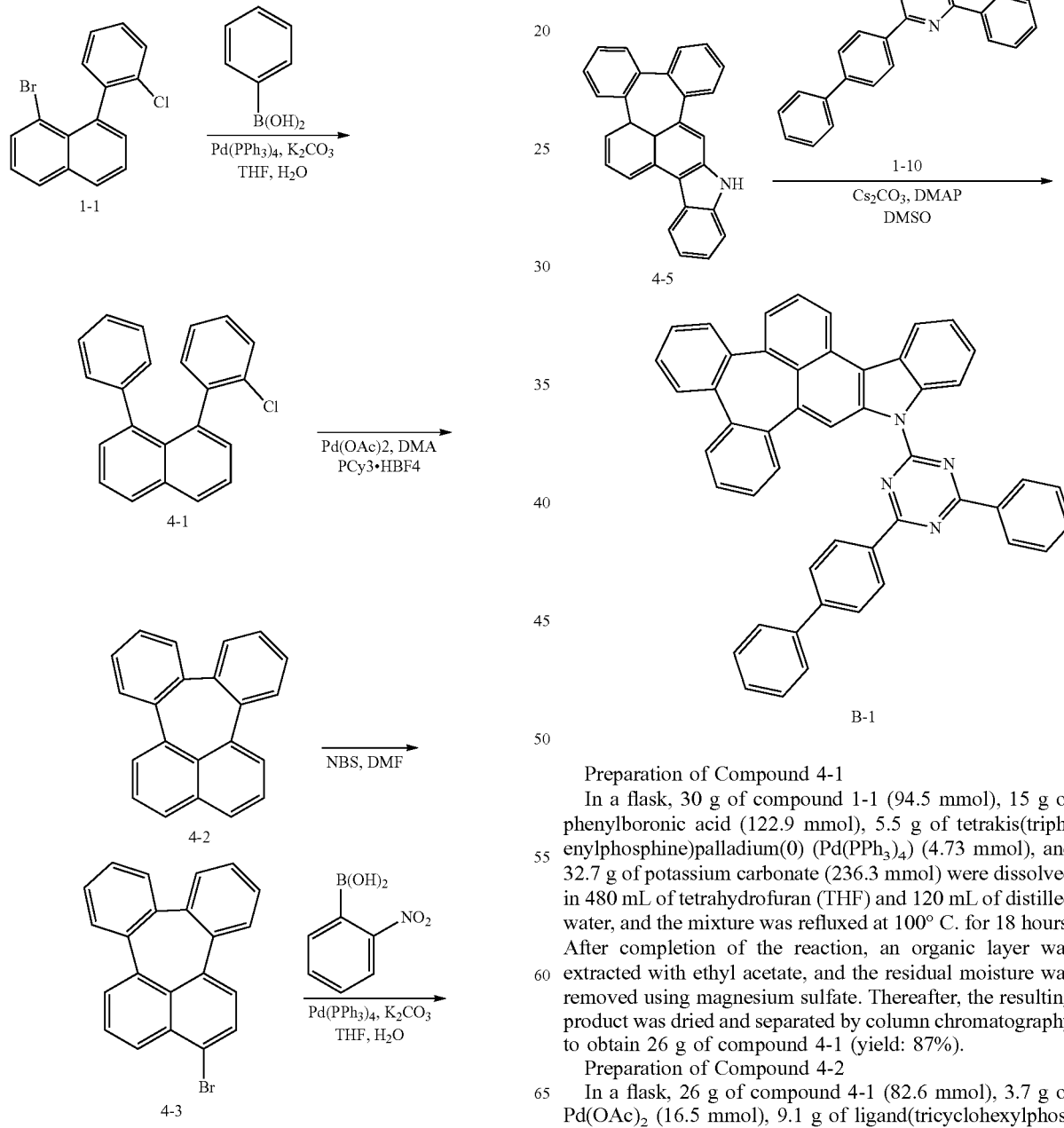

Preparation of Compound 4-1

In a flask, 30 g of compound 1-1 (94.5 mmol), 15 g of phenylboronic acid (122.9 mmol), 5.5 g of tetrakis(triphenylphosphine)palladium(0) (Pd(PPh$_3$)$_4$) (4.73 mmol), and 32.7 g of potassium carbonate (236.3 mmol) were dissolved in 480 mL of tetrahydrofuran (THF) and 120 mL of distilled water, and the mixture was refluxed at 100° C. for 18 hours. After completion of the reaction, an organic layer was extracted with ethyl acetate, and the residual moisture was removed using magnesium sulfate. Thereafter, the resulting product was dried and separated by column chromatography to obtain 26 g of compound 4-1 (yield: 87%).

Preparation of Compound 4-2

In a flask, 26 g of compound 4-1 (82.6 mmol), 3.7 g of Pd(OAc)$_2$ (16.5 mmol), 9.1 g of ligand(tricyclohexylphosphonium tetrafluoroborate) (24.8 mmol), and 80.7 g of Cs₂CO₃ (247.8 mmol) were dissolved in 413 mL of dimethyl acetamide (DMA) and stirred for 3 hours under reflux. The mixture was cooled to room temperature, and distilled water was added thereto. The mixture was then extracted with methylene chloride (MC), and dried with magnesium sulfate. Thereafter, the resulting product was distilled under reduced pressure and separated by column chromatography to obtain 23 g of compound 4-2 (yield: 70%).

Preparation of Compound 4-3

In a flask, 7 g of compound 4-2 (25.1 mmol) was dissolved in 125 mL of dimethyl formamide (DMF), and 5.4 g of N-bromosuccinimide (NBS) (30.1 mmol) was added thereto. The mixture was stirred at room temperature for 4 hours, and methanol and distilled water were added thereto. The produced solid was filtered under reduced pressure and separated by column chromatography to obtain 5.6 g of compound 4-3 (yield: 62%).

Preparation of Compound 4-4

In a flask, 13 g of compound 4-3 (37 mmol), 8.0 g of 2-nitrophenylboronic acid (48 mmol), 2.1 g of tetrakis (triphenylphosphine)palladium(0) (Pd(PPh₃)₄) (1.85 mmol), and 12.8 g of potassium carbonate (92.5 mmol) were dissolved in 180 mL of tetrahydrofuran (THF) and 45 mL of distilled water, and the mixture was refluxed at 100° C. for 18 hours. After completion of the reaction, an organic layer was extracted with ethyl acetate, and the residual moisture was removed using magnesium sulfate. Thereafter, the resulting product was dried and separated by column chromatography to obtain 7.6 g of compound 4-4 (yield: 52%).

Preparation of Compound 4-5

7.6 g of compound 4-4 (19 mmol), 12.5 g of triphenylphosphine (47.5 mmol), and 95 mL of 1,2-dichlorobenzene were introduced into a flask and stirred at 200° C. for 18 hours. After completion of the reaction, the solvent was removed by distillation under reduced pressure. Thereafter, the resulting product was separated by column chromatography to obtain 2.5 g of compound 4-5 (yield: 36%).

Preparation of Compound B-1

In a flask, 2.5 g of compound 4-5 (6.8 mmol), 2.3 g of compound 1-10 (6.8 mmol), 2.8 g of Cs₂CO₃ (20.4 mmol), and 0.42 g of 4-dimethylaminopyridine (DMAP) (3.4 mmol) were dissolved in 68 mL of dimethyl sulfoxide (DMSO), and the mixture was stirred at 100° C. for 2 hours. After completion of the reaction, the reaction solution was cooled to room temperature, and distilled water and methanol were added thereto. Thereafter, the solvent was removed using a filter, and the resulting solid was separated by column chromatography to obtain 2.2 g of compound B-1 (yield: 48%, melting point: 199° C., glass transition temperature: 177° C.).

Example 5: Preparation of Compound B-6

In a flask, 6.0 g of compound 4-5 (16 mmol), 4.7 g of 2-chloro-3-phenylquinoxaline (20 mmol), 10.6 g of Cs₂CO₃ (33 mmol), and 1.0 g of 4-dimethylaminopyridine (DMAP) (8 mmol) were dissolved in 82 mL of dimethyl sulfoxide (DMSO), and the mixture was stirred at 100° C. for 6 hours. After completion of the reaction, the reaction solution was cooled to room temperature, and distilled water and methanol were added thereto. The solvent was removed using a filter, and the resulting solid was separated by column chromatography to obtain 4.4 g of compound B-6 (yield: 47%, melting point: 271° C., glass transition temperature: 172° C.).

Example 6: Preparation of Compound A-62

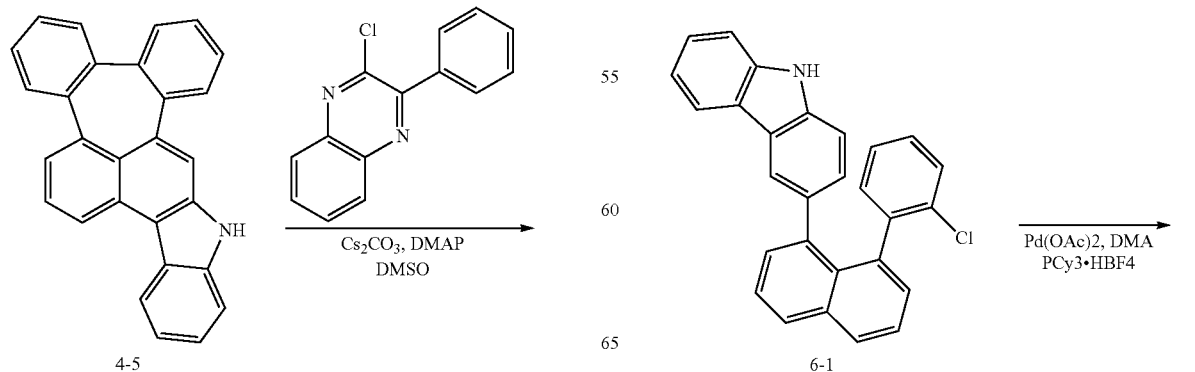

-continued

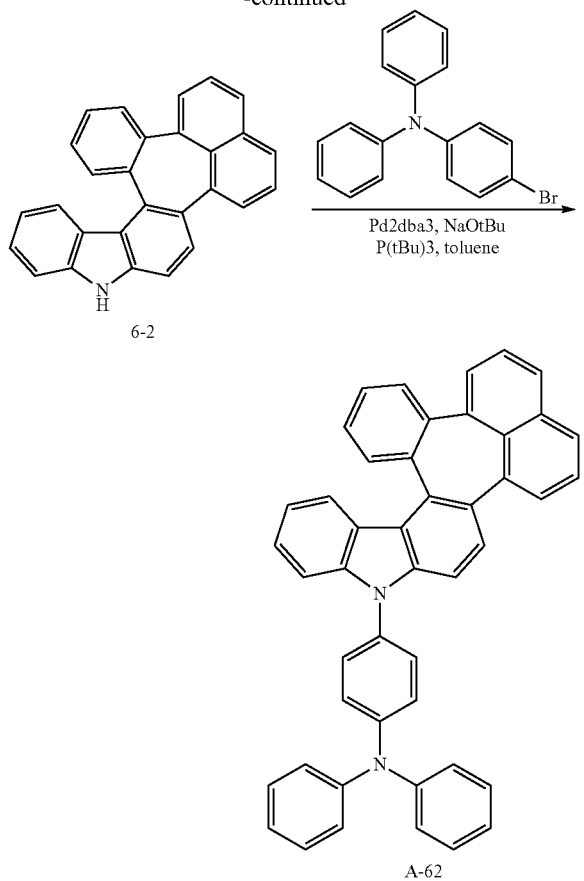

Preparation of Compound 6-1

In a flask, 35 g of compound 1-1 (110 mmol), 38.8 g of 3-(4,4,5,5-tetramethyl-1,3,2-dioxylboren-2-yl)-9H-carbazole (132 mmol), 6.5 g of tetrakis(triphenylphosphine)palladium(0) (Pd(PPh$_3$)$_4$) (5.5 mmol), and 38.1 g of potassium carbonate (275 mmol) were dissolved in 560 mL of tetrahydrofuran (THF) and 140 mL of distilled water, and the mixture was refluxed at 100° C. for 18 hours. After completion of the reaction, an organic layer was extracted with ethyl acetate, and the residual moisture was removed using magnesium sulfate. Thereafter, the resulting product was dried and separated by column chromatography to obtain 30 g of compound 6-1 (yield: 67%).

Preparation of Compound 6-2

In a flask, 30 g of compound 6-1 (74 mmol), 3.3 g of Pd(OAc)$_2$ (15 mmol), 8.2 g of ligand(tricyclohexylphosphonium tetrafluoroborate) (22 mmol), and 72.6 g of Cs$_2$CO$_3$ (223 mmol) were dissolved in 372 mL of dimethyl acetamide (DMA) and stirred for 6 hours under reflux. The mixture was cooled to room temperature, and distilled water was added thereto. An organic layer was then extracted with ethyl acetate and dried with magnesium sulfate. Thereafter, the resulting product was distilled under reduced pressure and separated by column chromatography to obtain 24 g of compound 6-2 (yield: 44%).

Preparation of Compound A-62

5.0 g of compound 6-2 (14 mmol), 5.3 g of 4-bromo-N,N-diphenylaniline (16 mmol), 0.62 g of tris(dibenzylideneacetone)dipalladium(0) (0.68 mmol), 0.54 mL of tri-t-butylphosphine (1.4 mmol, 50% toluene solution), 2.6 g of sodium t-butoxide (28 mmol), and 136 mL of toluene were introduced into a flask and refluxed for 6 hours. The reaction solution was cooled to room temperature, and the solvent was removed by a rotary evaporator. Thereafter, the residue was purified by column chromatography to obtain 2.4 g of white solid compound A-62 (yield: 29%, melting point: 188° C., glass transition temperature: 162° C.).

Device Examples 1 to 3: Production of an OLED device using the Compound according to the present disclosure as a host An organic light-emitting diode (OLED) device was produced comprising the compound according to the present disclosure. A transparent electrode indium tin oxide (ITO) thin film (10 Ω/sq) on a glass substrate for an OLED device (Geomatec, Japan) was subjected to an ultrasonic washing with acetone, ethanol, and distilled water, sequentially, and was then stored in isopropyl alcohol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. Compound HT-2 was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. The compound shown in Table 1 below was introduced into one cell of the vacuum vapor depositing apparatus as a host, and compound D-71 was introduced into another cell as a dopant. The two materials were evaporated at different rates and were deposited in a doping amount of 3 wt % based on the total amount of the host and dopant to form a light-emitting layer having a thickness of 40 nm on the second hole transport layer. Compound ET-1 and compound EI-1 were then introduced into two other cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced.

Comparative Example 1: Production of an OLED device using a comparative compound as a host An OLED device was produced in the same manner as in Device Example 1, except that compound A was used as the host of the light-emitting layer.

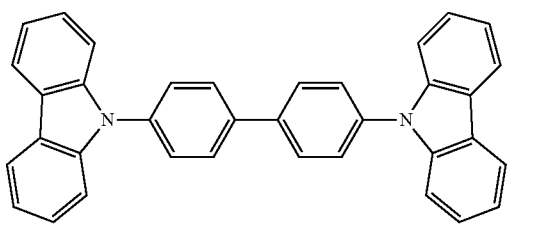

Compound A

TABLE 1

|  | Host Material | Driving Voltage (V) | Color | Lifespan (T95, hr) |
|---|---|---|---|---|
| Comparative Example 1 | CBP | 9.2 | Red | 0.25 |
| Device Example 1 | B-10 | 4.9 | Red | 3.6 |
| Device Example 2 | B-15 | 3.5 | Red | 4.6 |
| Device Example 3 | B-6 | 3.6 | Red | 2.6 |

The organic electroluminescent device comprising the organic electroluminescent compound of the present disclosure as a host exhibited lower driving voltage and better lifespan characteristics than the organic electroluminescent device comprising the compound of Comparative Example 1.

Device Example 4: Production of an OLED device using the compound According to the present disclosure as a second hole transport material An OLED device was produced comprising the compound according to the present disclosure. A transparent electrode indium tin oxide (ITO) thin film (10 Ω/sq) on a glass substrate for an OLED device (Geomatec, Japan) was subjected to an ultrasonic washing with acetone and isopropyl alcohol, sequentially, and was then stored in isopropyl alcohol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 90 nm on the ITO substrate. Compound HI-2 was then introduced into another cell of said vacuum vapor depositing apparatus, and was evaporated by applying an electric current to the cell, thereby forming a second hole injection layer having a thickness of 5 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. The compound shown in Table 2 below as a second hole transport material (auxiliary material) was introduced into another cell of said vacuum vapor depositing apparatus, and was evaporated by applying an electric current to the cell, thereby forming a second hole transport layer having a thickness of 60 nm on the first hole transport layer. After forming the hole injection layers and the hole transport layers, a light-emitting layer was then deposited as follows. Compound H-1 was introduced into one cell of the vacuum vapor depositing apparatus as a host, and compound D-71 was introduced into another cell as a dopant. The two materials were evaporated at different rates and were deposited in a doping amount of 2 wt % based on the total amount of the host and dopant to form a light-emitting layer having a thickness of 40 nm on the second hole transport layer. Compound ET-1 and compound EI-1 were then introduced into two other cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 1500 nm was deposited by another vacuum vapor deposition apparatus. Thus, an OLED device was produced.

The driving voltage, luminous efficiency, and CIE coordinates at a luminance of 1,000 nits, and the time taken for luminance to decrease from 100% to 98% at a constant current and at a luminance of 5,000 nits (lifespan; T98) of the produced OLED device are provided in Table 2 below.

Comparative Example 2: Production of an OLED device using a comparative compound as a second hole transport material An OLED device was produced in the same manner as in Device Example 4, except that compound HT-1 was used as the second hole transport material.

The produced OLED device was evaluated in the same manner as in Device Example 4.

TABLE 2

|  | Second Hole Transport Layer (Auxiliary Layer) | Host | Driving Voltage (V) | Luminous Efficiency (cd/A) | CIE (x, y) | Lifespan (T98, hr) |
|---|---|---|---|---|---|---|
| Device Example 4 | A-9 | H-1 | 3.2 | 21.7 | (0.670, 0.330) | 83 |
| Comparative Example 2 | HT-1 |  | 3.2 | 11.4 | (0.661, 0.336) | 27 |

The organic electroluminescent device comprising the organic electroluminescent compound of the present disclosure as a second hole transport material exhibited higher luminous efficiency and better lifespan characteristics than the organic electroluminescent device comprising the compound of Comparative Example 2.

TABLE 3

Organic electroluminescent materials used in the Device Examples and the Comparative Examples Hole Injection Layer/ Hole Transport Layer

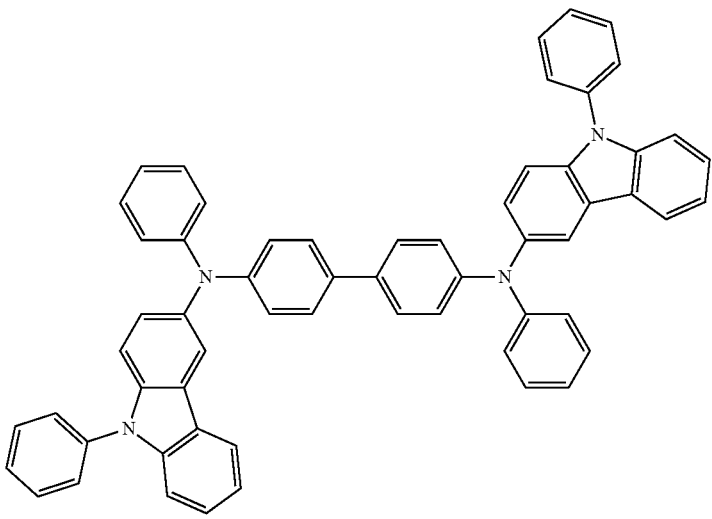

HI-1

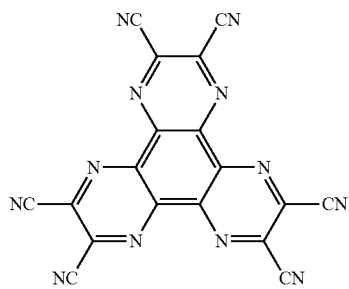

HI-2

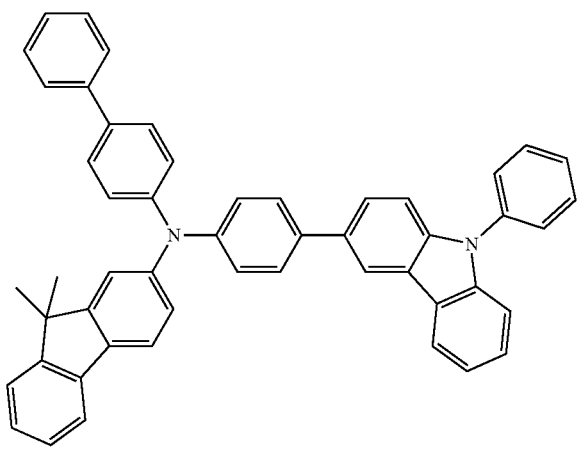

HT-1

TABLE 3-continued
Organic electroluminescent materials used in the Device Examples and the Comparative Examples
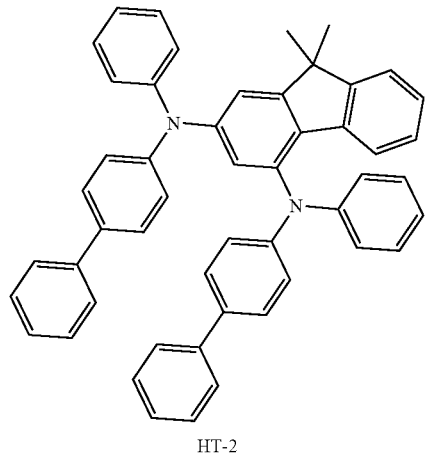
HT-2
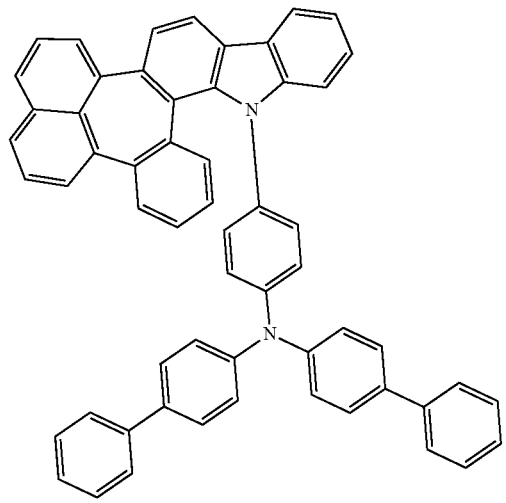
A-9
Light-Emitting
Layer
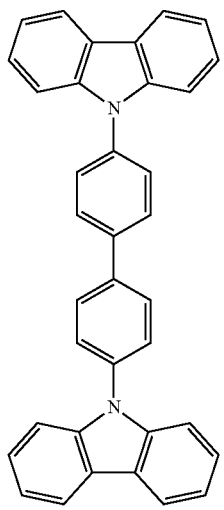
Compound A TABLE 3-continued
Organic electroluminescent materials used in the Device Examples and the Comparative Examples
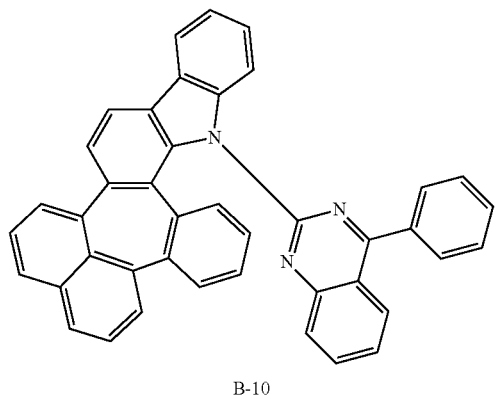
B-10
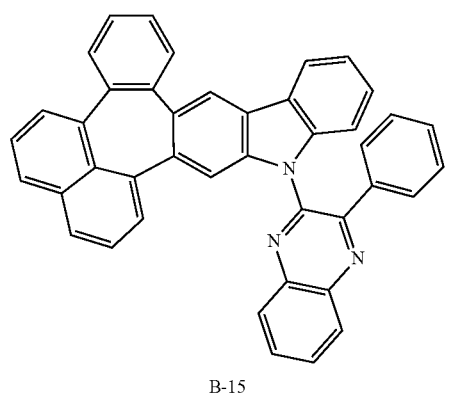
B-15
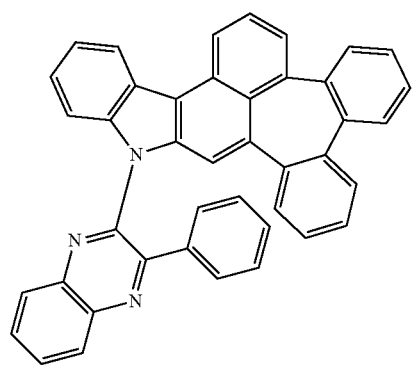
B-6
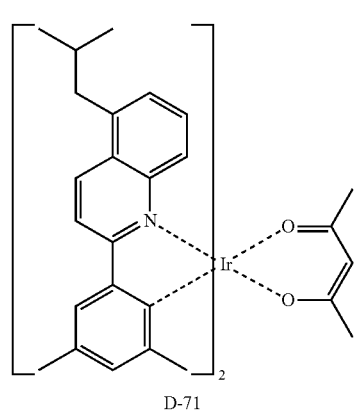
D-71

TABLE 3-continued

Organic electroluminescent materials used in the Device Examples and the Comparative Examples

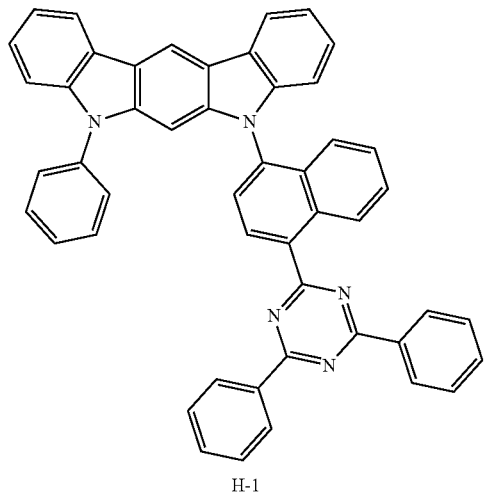

H-1

Electron Transport Layer/Electron Injection Layer

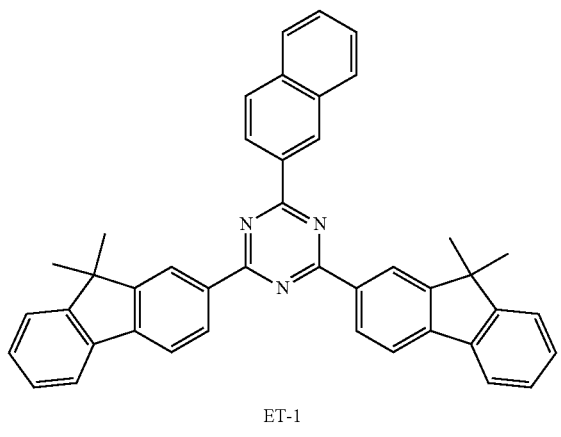 [SMILES: CC1(C)c2ccccc2-c2ccc(-c3nc(-c4ccc5c(c4)C(C)(C)c4ccccc4-5)nc(-c4ccc5ccccc5c4)n3)cc21]

ET-1

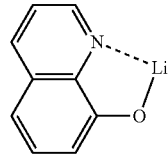

EI-1

The invention claimed is:

1. An organic electroluminescent compound represented by the following formula 1:

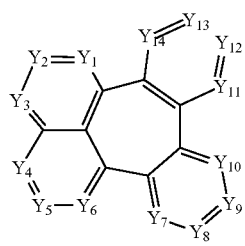

(1)

wherein $Y_1$ to $Y_{14}$ each independently represent N or $CR_1$, in which if a plurality of $R_1$'s is present, each $R_1$ may be the same or different;

with the proviso that at least a pair of $Y_1$ to $Y_{14}$ wherein two of $Y_1$ to $Y_{14}$ are adjacent to each other are fused with the following formula 2 to form a ring:

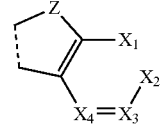

(2)

Z represents NR$_2$, O, S, CR$_3$R$_4$ or SiR$_5$R$_6$;

X$_1$ to X$_4$ each independently represent N or CR$_7$, in which if a plurality of R$_7$'s is present, each R$_7$ may be the same or different;

the dotted line represents a site fused with the adjacent two of Y$_1$ to Y$_{14}$ of formula 1;

R$_2$ represents

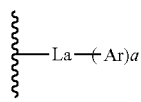

wherein ⁀ represents the bonding site of La to the nitrogen of NR$_2$;

La represents a single bond, a substituted or unsubstituted (C6-C30)arylene, a substituted or unsubstituted (3- to 30-membered)heteroarylene, or a substituted or unsubstituted (C3-C30)cycloalkylene;

Ar represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C6-C30)aryl(3- to 30-membered)heteroarylamino, or a substituted or unsubstituted (C1-C30)alkyl(C6-C30)arylamino;

R$_1$ and R$_7$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, a substituted or unsubstituted (C6-C30)aryl(3- to 30-membered)heteroarylamino, or a substituted or unsubstituted (C1-C30)alkyl(C6-C30)arylamino; or adjacent two R$_1$'s or adjacent two R$_7$'s may be linked to each other to form a ring;

R$_3$ to R$_6$ each independently represent hydrogen, deuterium, a halogen, a cyano, a substituted or unsubstituted (C1-C30)alkyl, a substituted or unsubstituted (C6-C30)aryl, or a substituted or unsubstituted (3- to 30-membered)heteroaryl; or R$_3$ and R$_4$, or R$_5$ and R$_6$ may be linked to each other to form a ring; and a is an integer of 1 to 4, in which if a is 2 or more, each Ar may be the same or different.

2. The organic electroluminescent compound according to claim 1, wherein the substituents of the substituted (C1-C30)alkyl, the substituted (C6-C30)aryl(ene), the substituted (3- to 30-membered) heteroaryl(ene), the substituted (C3-C30)cycloalkyl(ene), the substituted (C1-C30)alkoxy, the substituted tri(C1-C30)alkylsilyl, the substituted di(C1-C30)alkyl(C6-C30)arylsilyl, the substituted (C1-C30)alkyldi(C6-C30)arylsilyl, the substituted tri(C6-C30)arylsilyl, the substituted mono- or di-(C1-C30)alkylamino, the substituted mono- or di-(C6-C30)arylamino, the substituted (C6-C30)aryl(3- to 30-membered)heteroarylamino, and the substituted (C1-C30)alkyl(C6-C30)arylamino in La, Ar, R$_1$, and R$_3$ to R$_7$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (5- to 30-membered)heteroaryl unsubstituted or substituted with a (C6-C30)aryl; a (C6-C30)aryl unsubstituted or substituted with a (5- to 30-membered)heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

3. The organic electroluminescent compound according to claim 1, wherein

Z represents NR$_2$, O or S;

La represents a single bond, a substituted or unsubstituted (C6-C15)arylene, or a substituted or unsubstituted (5- to 15-membered)heteroarylene;

Ar represents a substituted or unsubstituted (C6-C15)aryl, a substituted or unsubstituted (5- to 15-membered) heteroaryl, a substituted or unsubstituted di(C6-C15) arylamino, or a substituted or unsubstituted (C6-C15) aryl(5- to 15-membered)heteroarylamino;

R$_1$ represents hydrogen;

R$_7$ represents hydrogen, a substituted or unsubstituted (C6-C15)aryl, a substituted or unsubstituted (5- to 15-membered)heteroaryl, a substituted or unsubstituted di(C6-C15)arylamino, or a substituted or unsubstituted (C6-C15)aryl(5- to 15-membered)heteroarylamino; and a is 1 or 2.

4. The organic electroluminescent compound according to claim 1, wherein

Z represents NR$_2$, O or S;

La represents a single bond, an unsubstituted (C6-C15) arylene, or an unsubstituted (5- to 15-membered)heteroarylene;

Ar represents an unsubstituted (C6-C15)aryl, a (5- to 15-membered)heteroaryl unsubstituted or substituted with a (C6-C15)aryl, a di(C6-C15)arylamino unsubstituted or substituted with a (C1-C6)alkyl, or an unsubstituted (C6-C15)aryl(5- to 15-membered)heteroarylamino;

R$_1$ represents hydrogen;

R$_7$ represents hydrogen, an unsubstituted (C6-C15)aryl, a (5- to 15-membered)heteroaryl unsubstituted or substituted with a (C6-C15)aryl, a di(C6-C15)arylamino unsubstituted or substituted with a (C1-C6)alkyl, or an unsubstituted (C6-C15)aryl(5- to 15-membered)heteroarylamino; and a is 1 or 2.

5. The organic electroluminescent compound according to claim 1, wherein the compound represented by formula 1 is selected from the group consisting of:
A-1
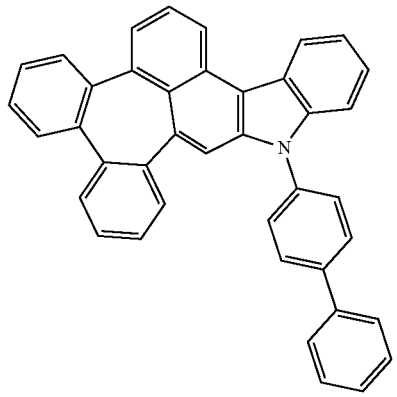
A-2
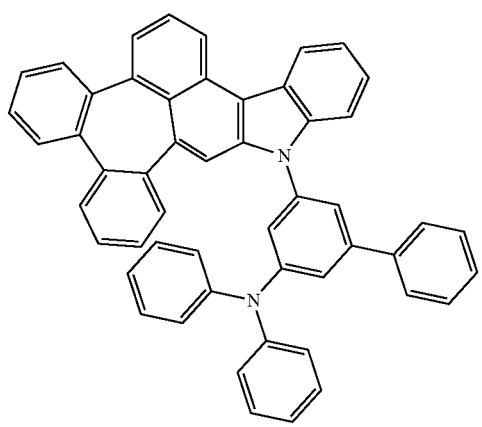
A-3
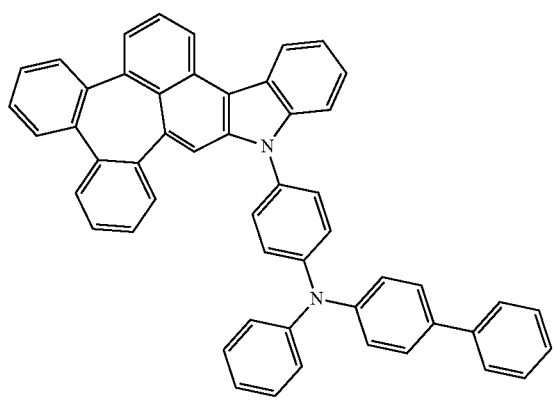
-continued
A-4
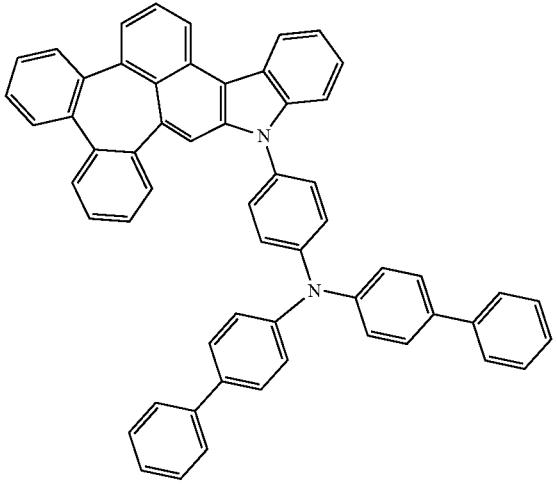
A-5
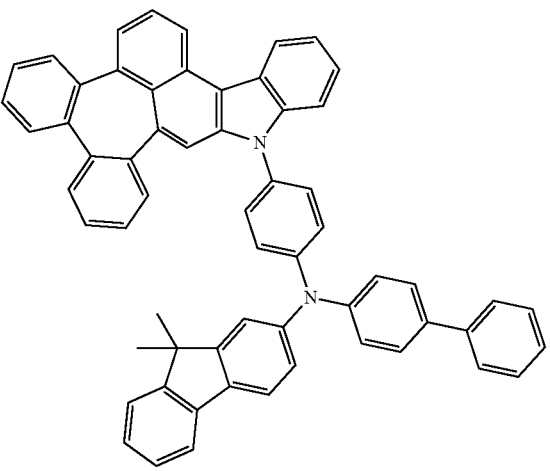
A-6
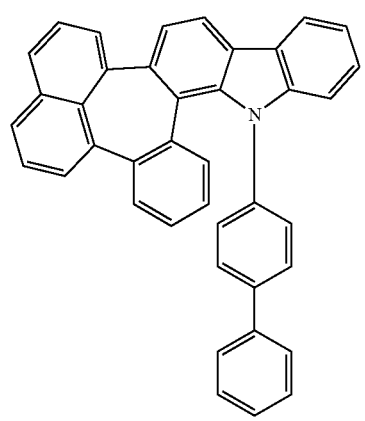

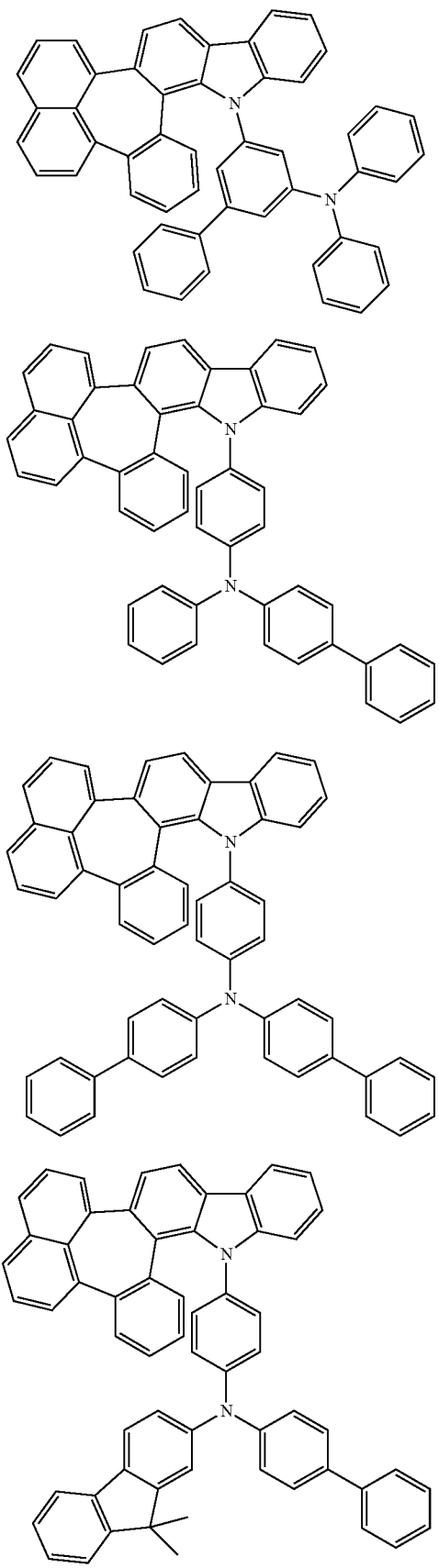
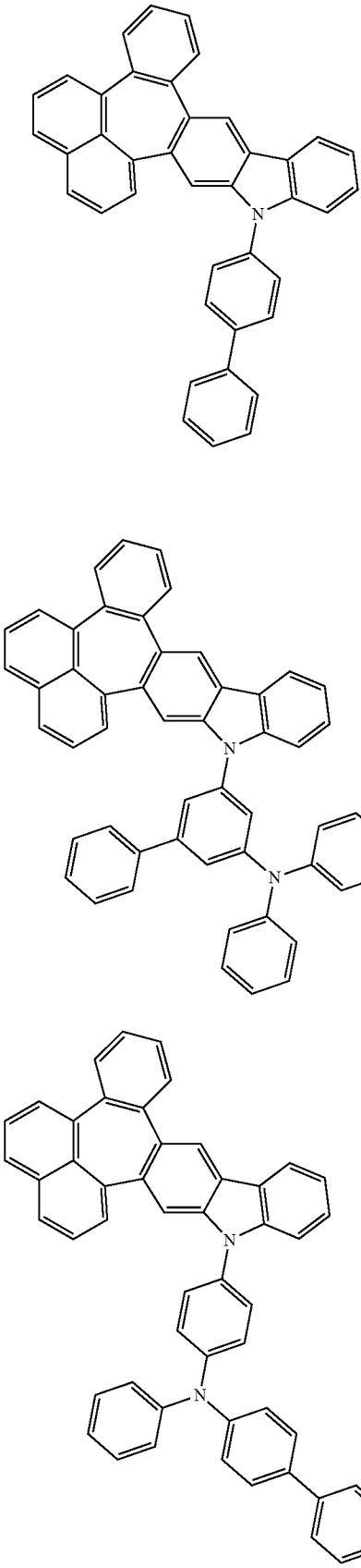

A-14
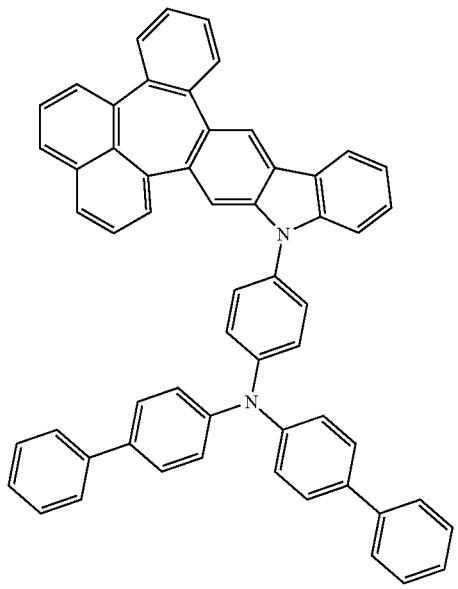
B-17
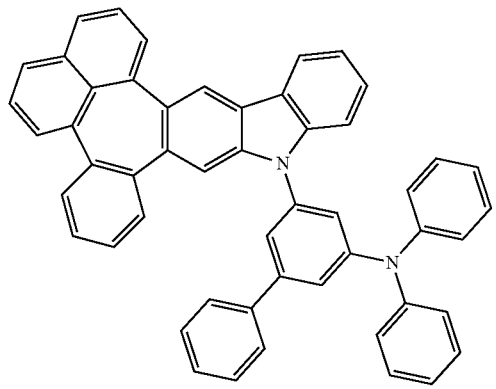
B-18
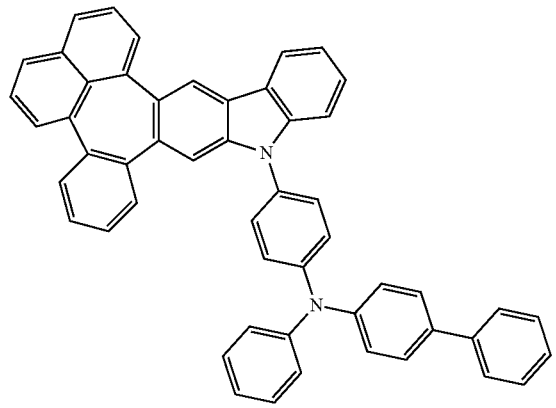
A-15
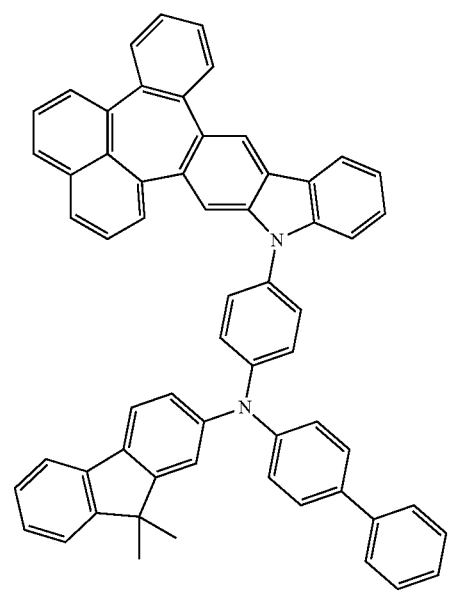
A-16
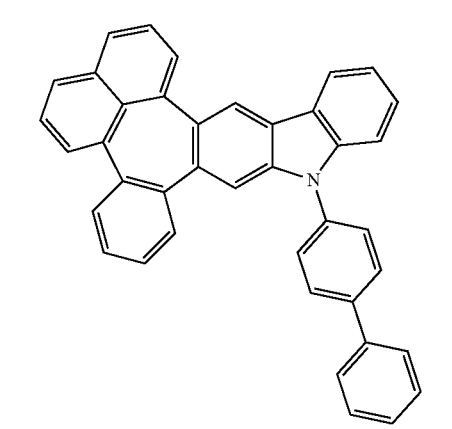
B-19
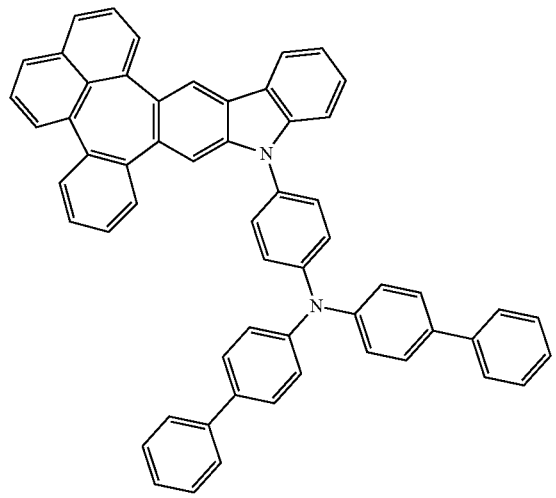

B-20
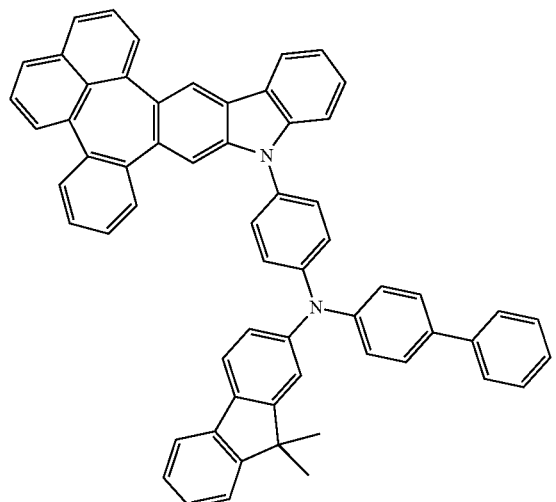
A-21
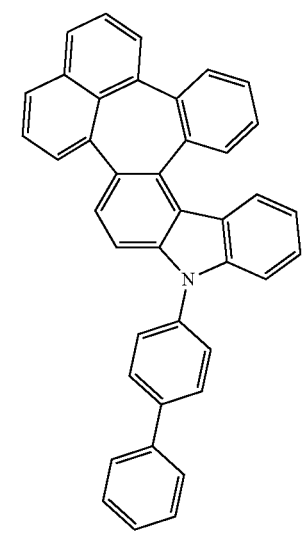
A-22
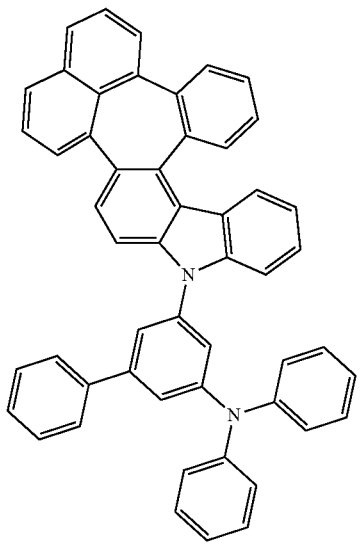
A-23
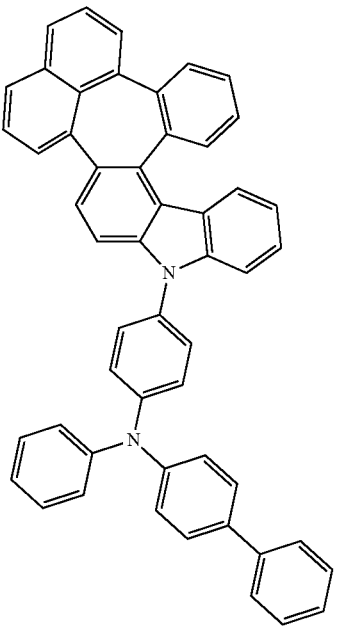
A-24
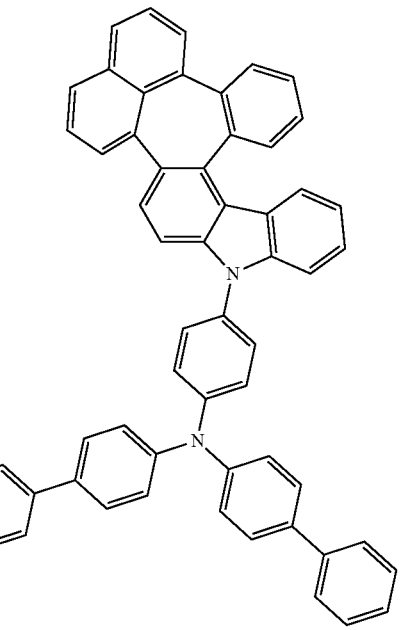

A-25
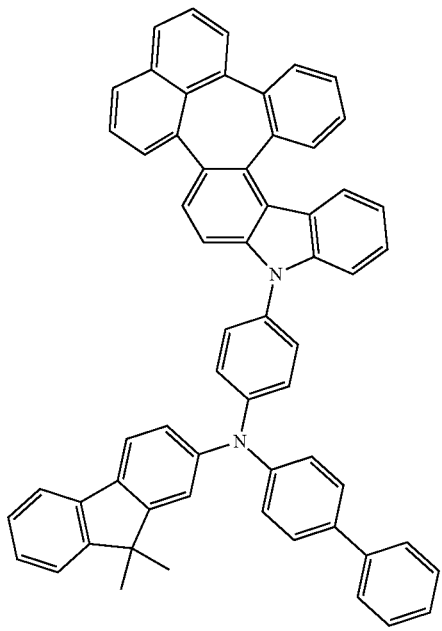
A-28
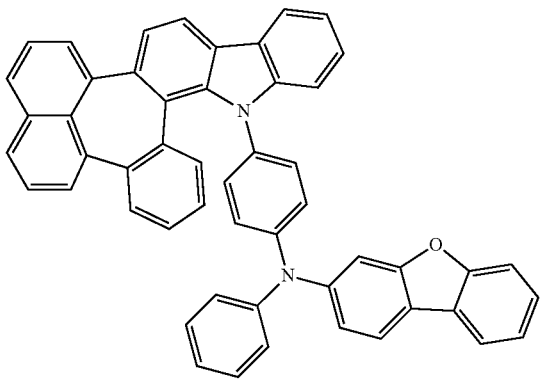
A-26
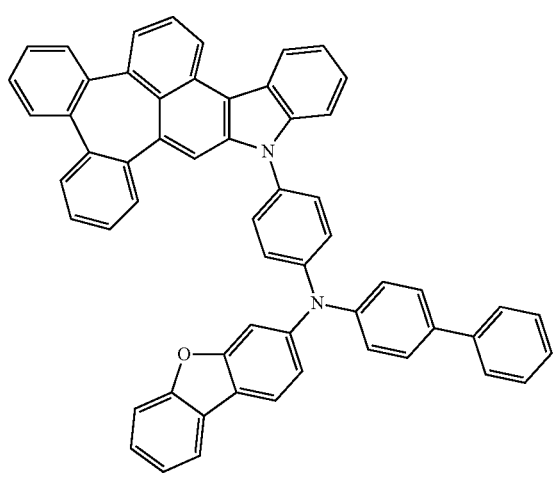
A-29
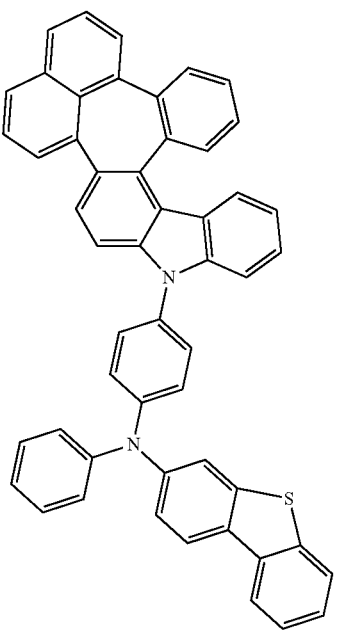
A-27
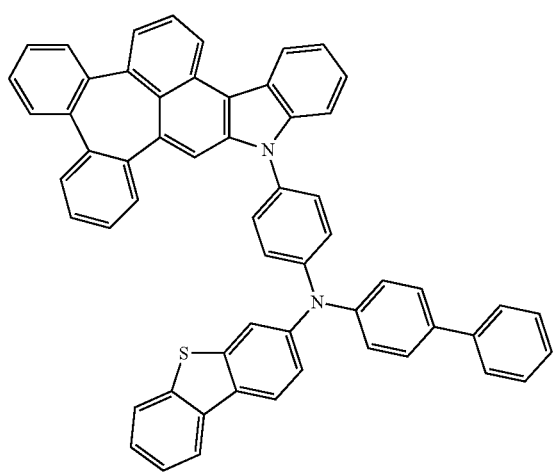
A-30
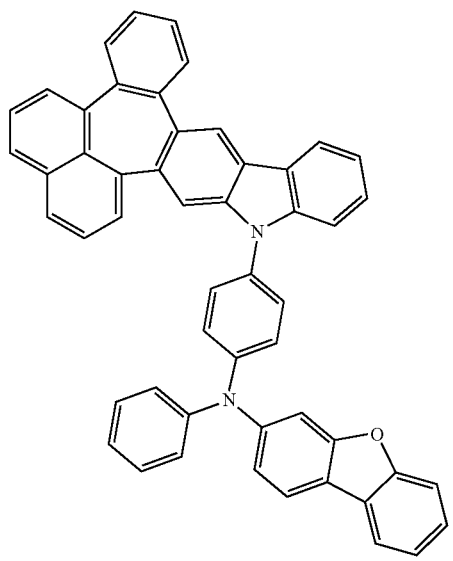

A-31
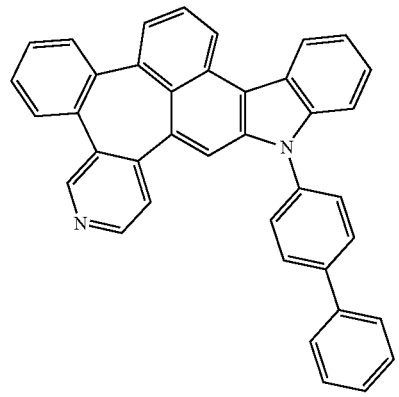
A-32
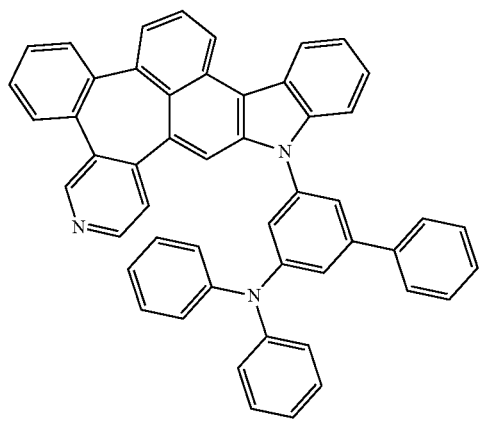
A-33
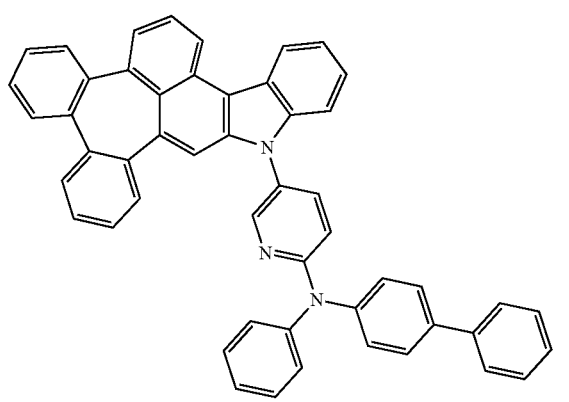
A-34
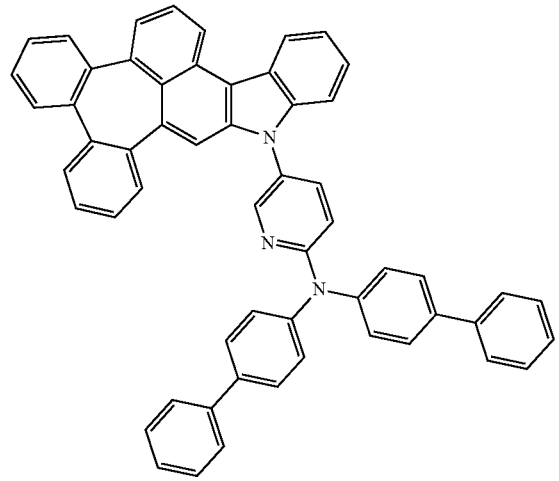
A-35
A-36
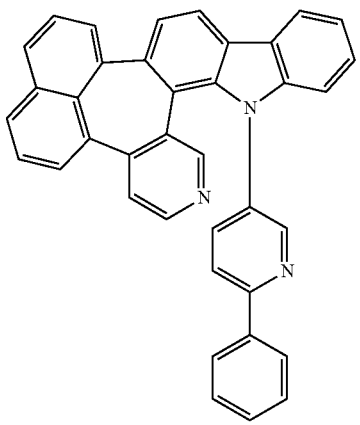

A-37
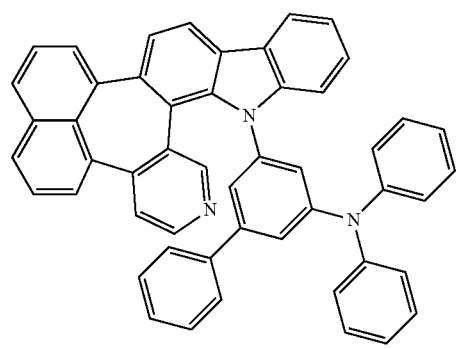
A-38
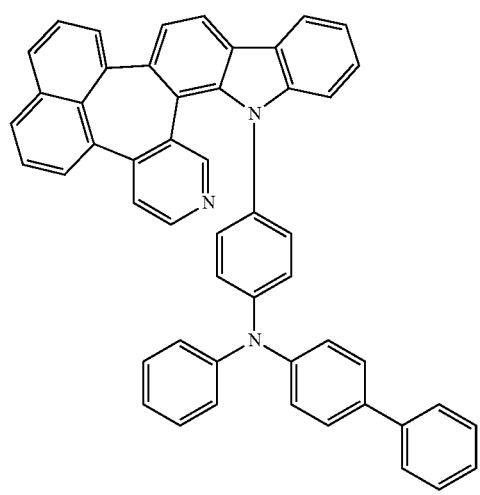
A-39
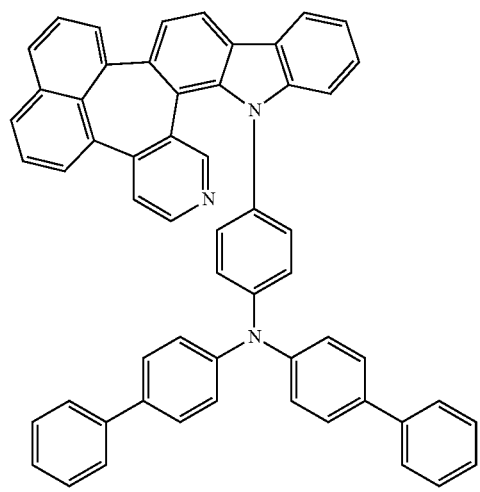
A-40
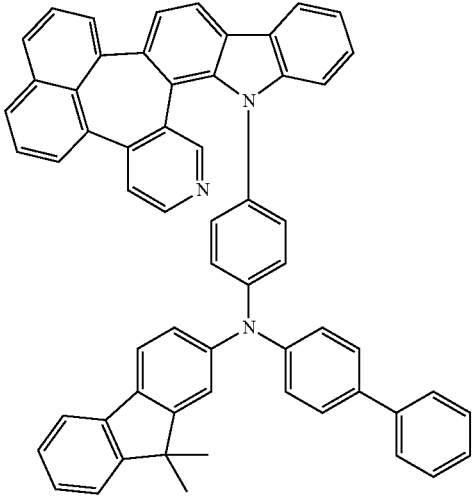
A-41
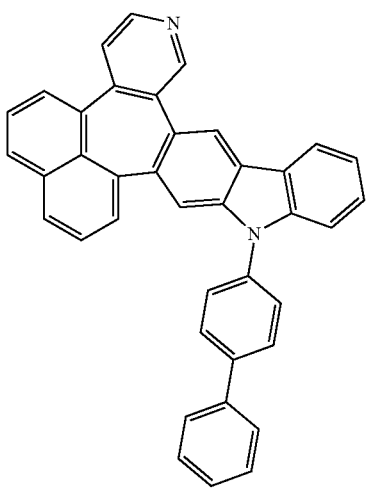
A-42
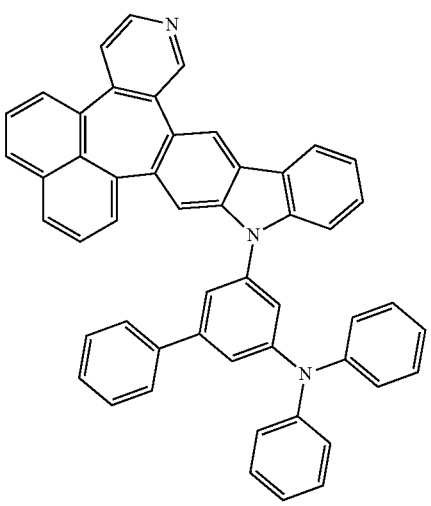

-continued
A-43
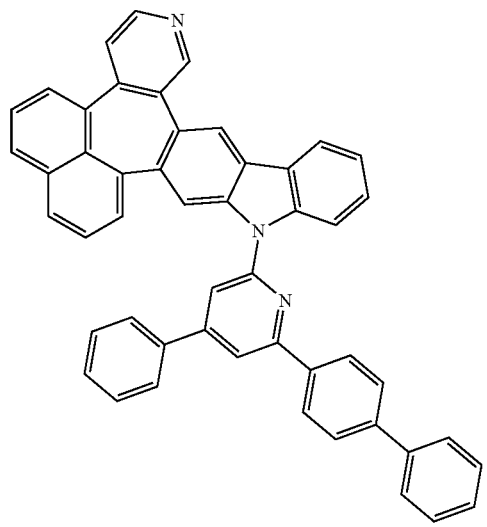
A-44
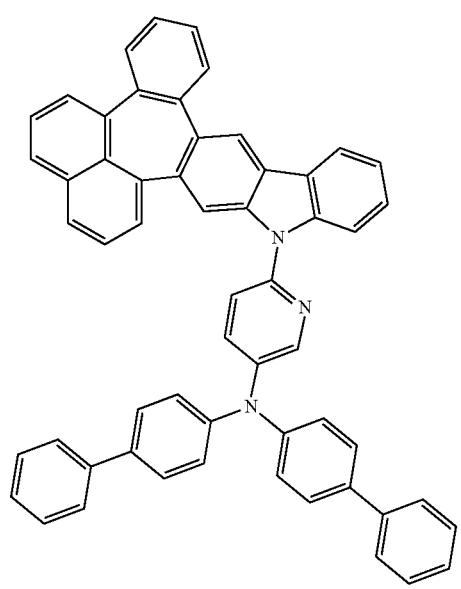
A-45
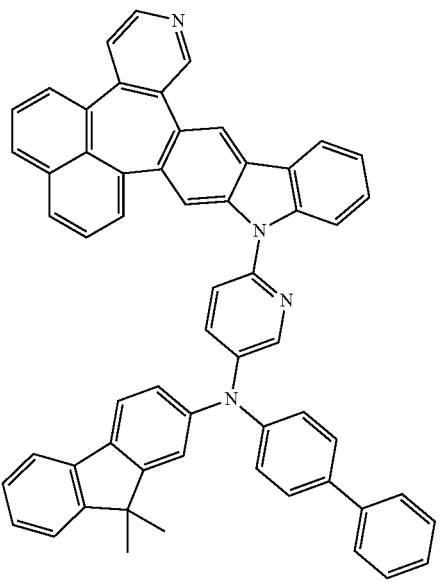
A-46
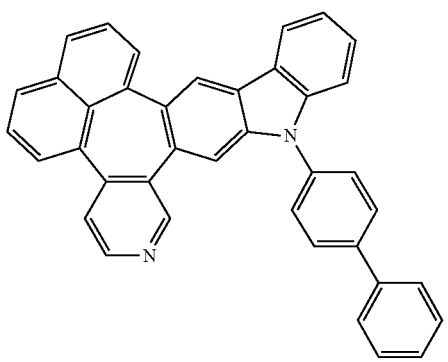
A-47
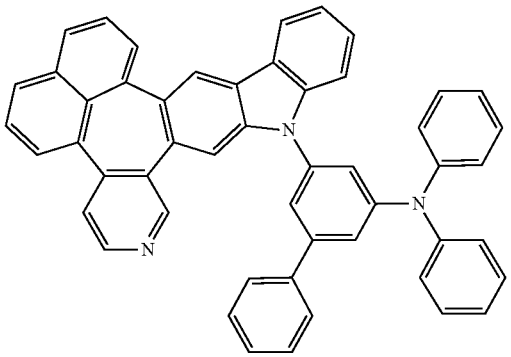

A-48
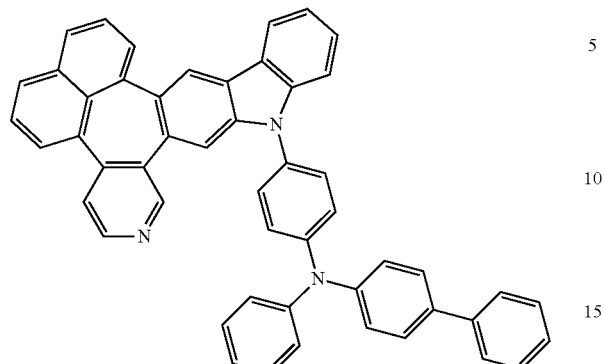
A-49
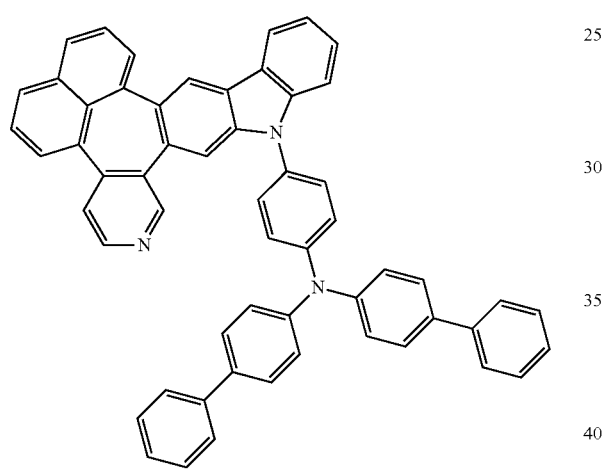
A-50
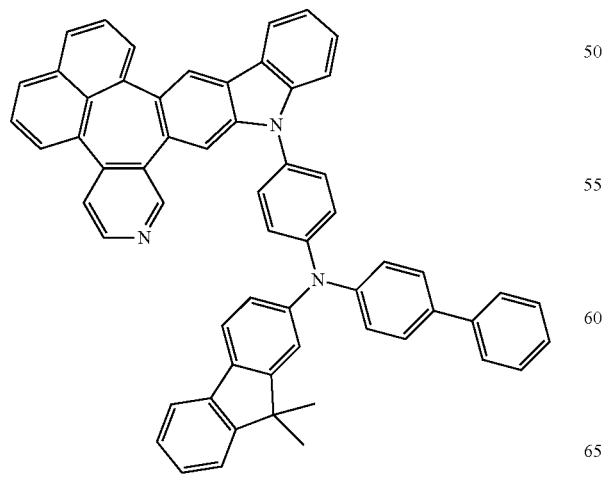
A-51
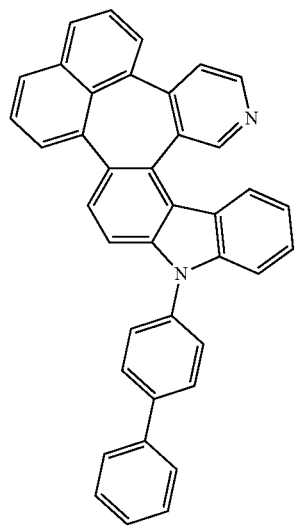
A-52
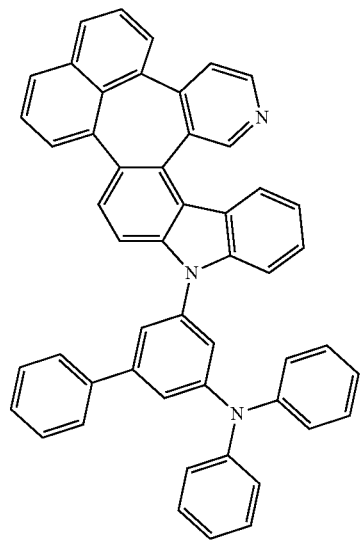

-continued
A-53
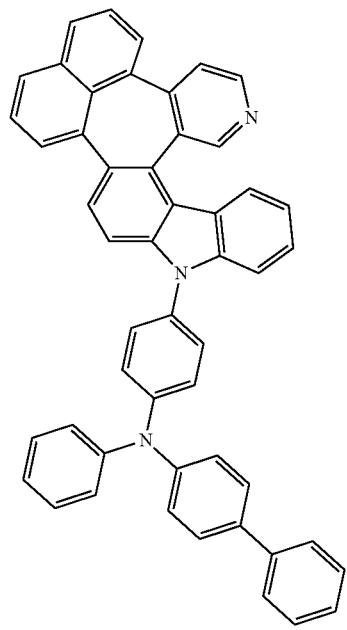
A-54
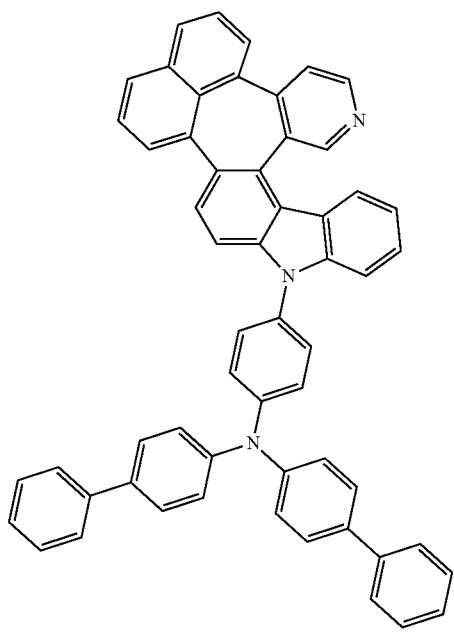
-continued
A-55
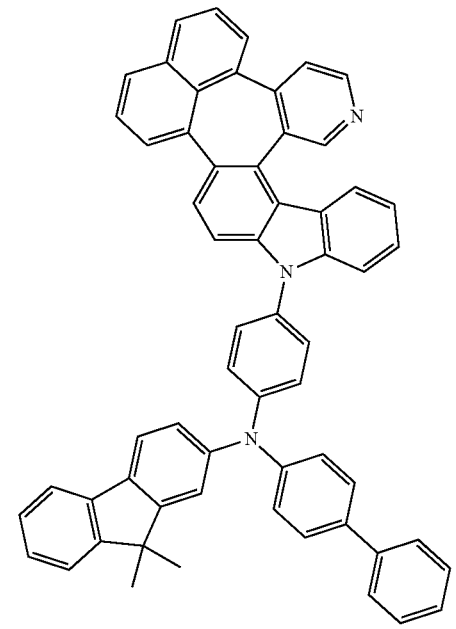
A-56
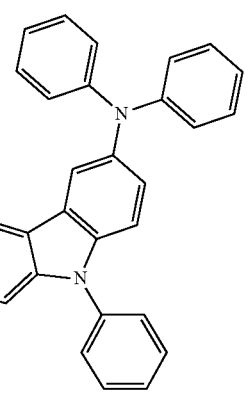
A-57

-continued
A-58
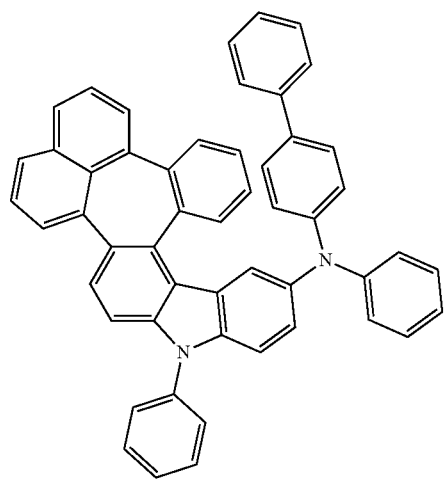
A-59
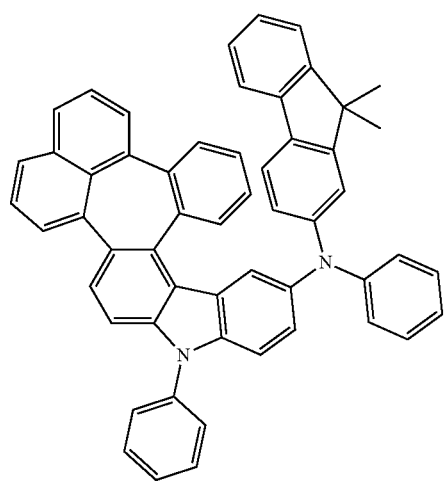
A-60
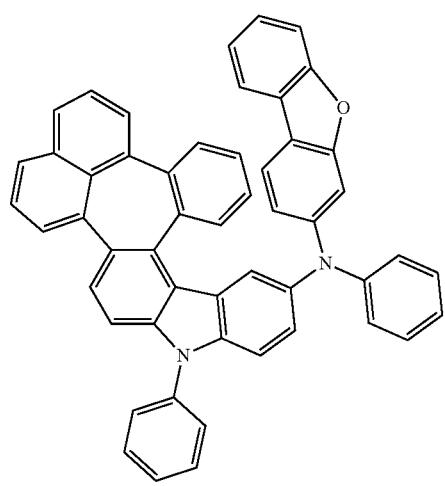
-continued
A-61
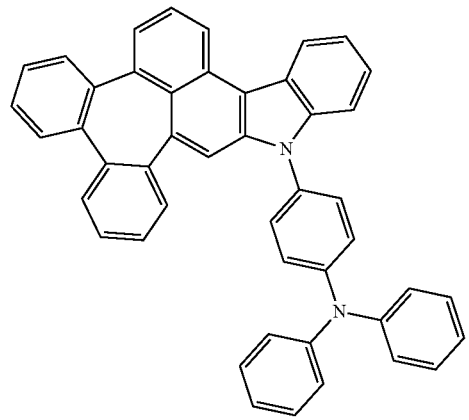
A-62
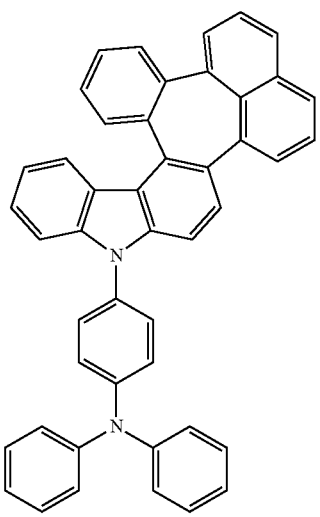
A-63
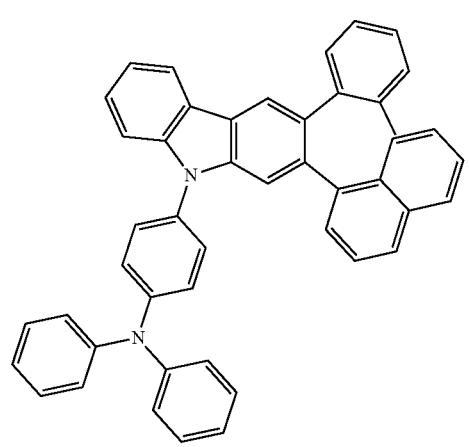

A-64
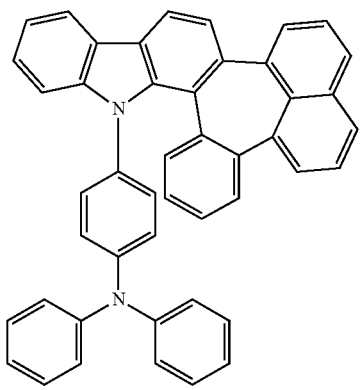
B-2
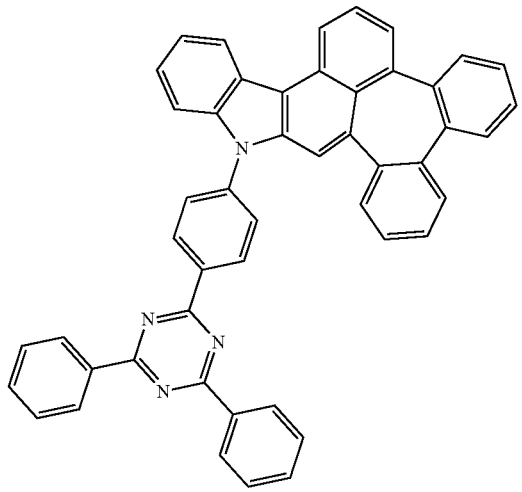
A-65
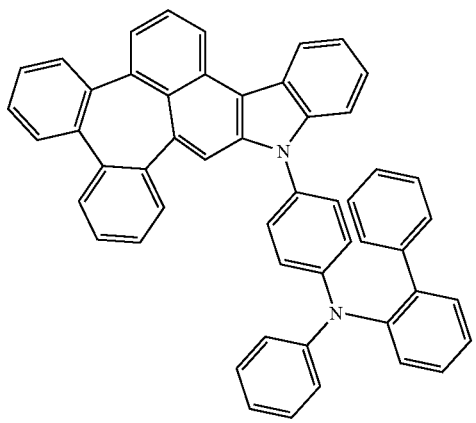
B-3
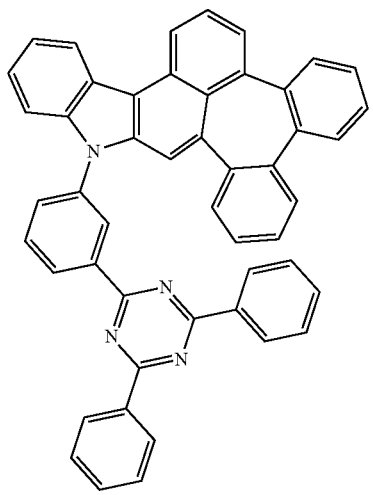
B-1
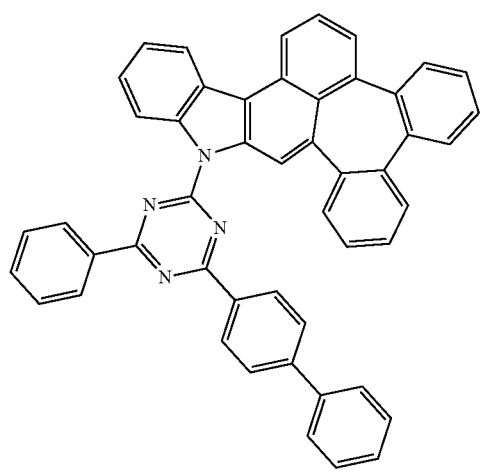
B-4
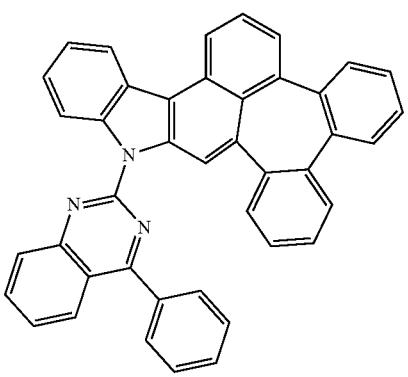

B-5
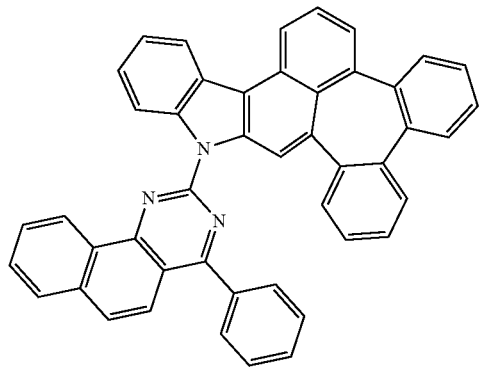
B-6
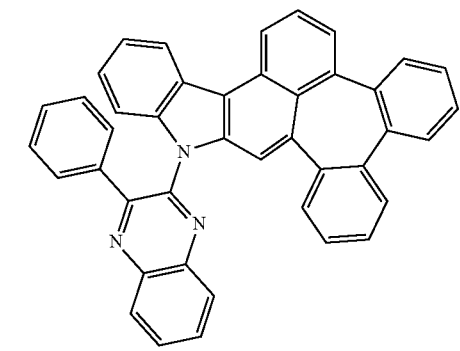
B-7
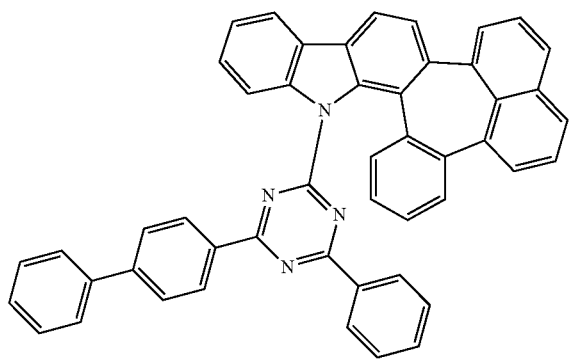
B-8
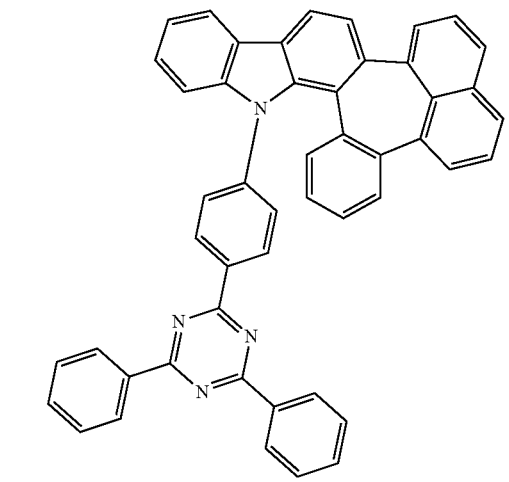
B-9
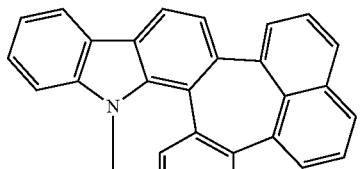
B-10
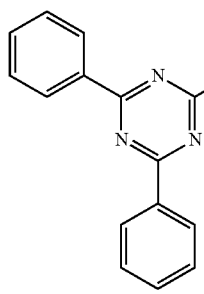
B-11
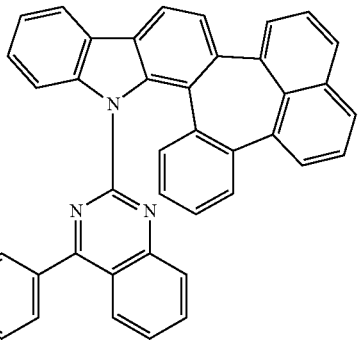
B-12
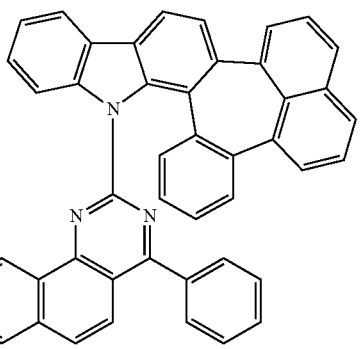
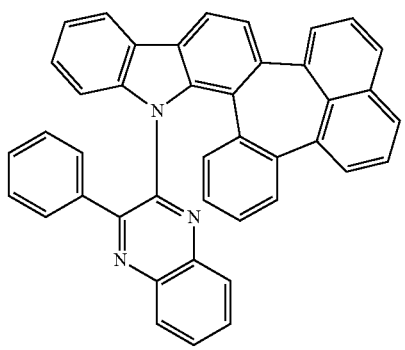

B-13
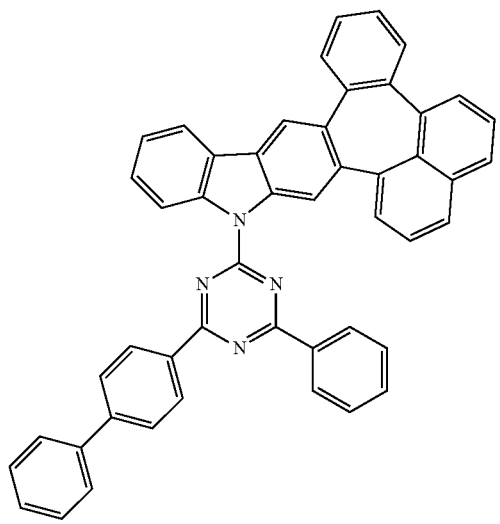
B-14
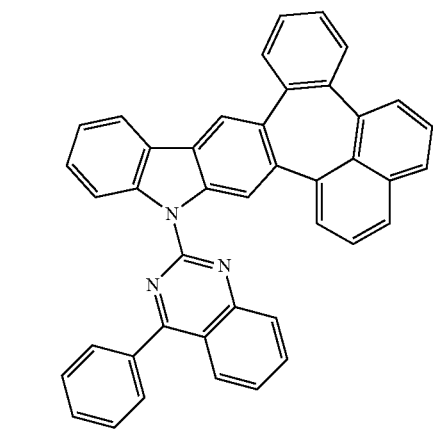
B-15
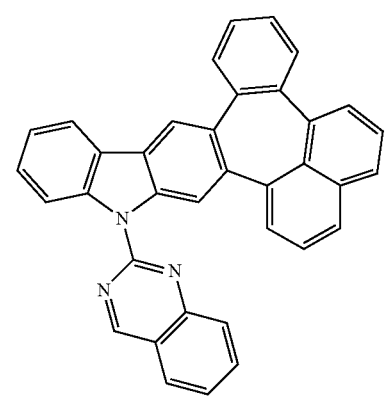
B-16
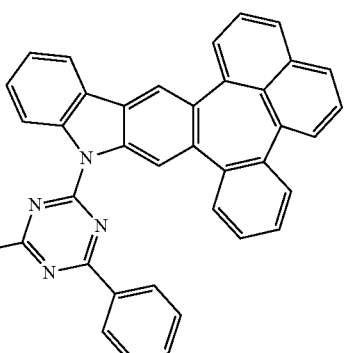
B-17, B-18, B-19
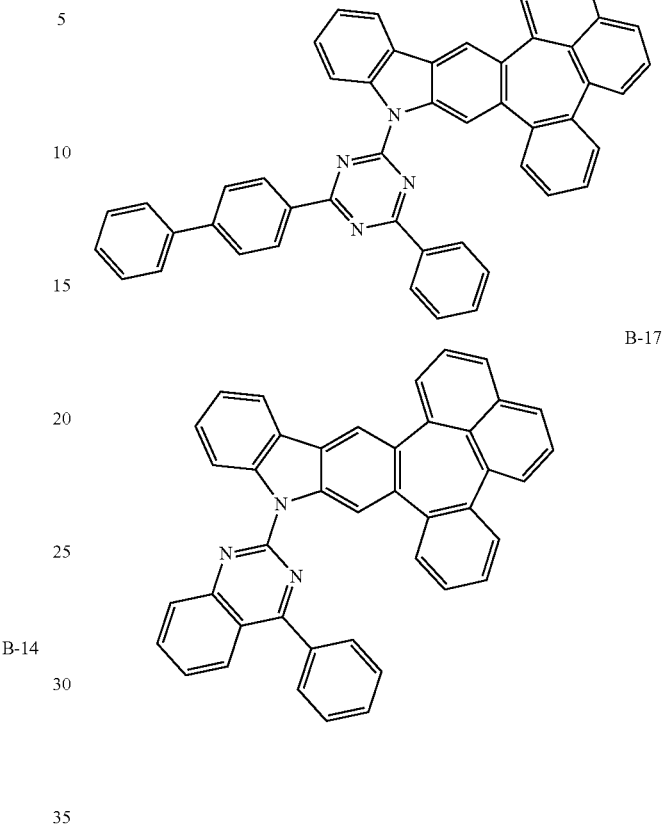
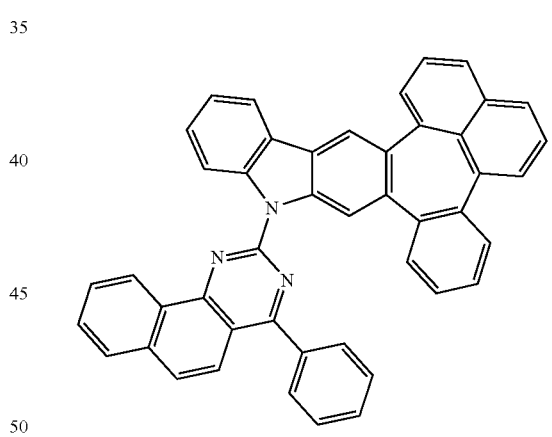
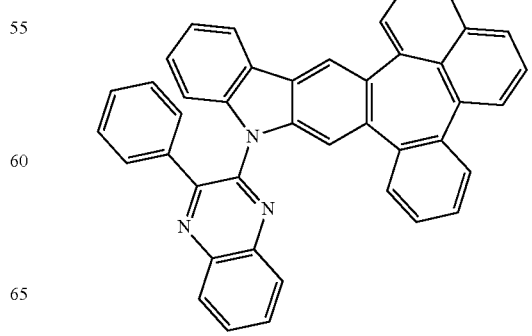

B-20
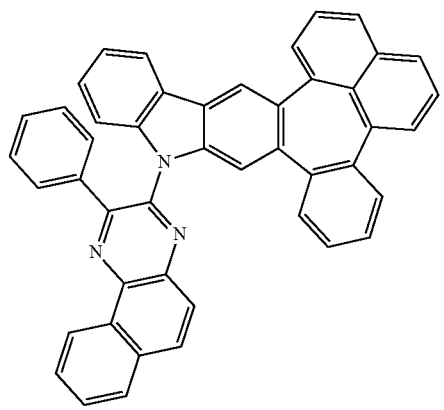
B-21
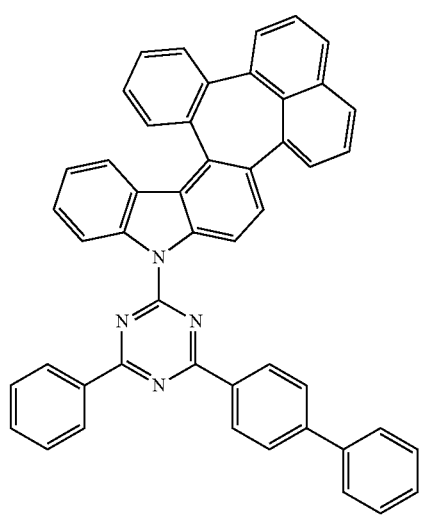
B-22
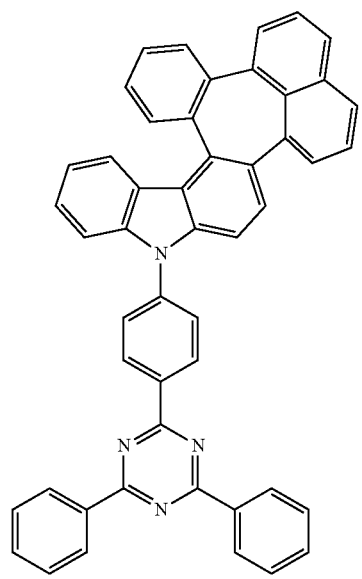
B-23
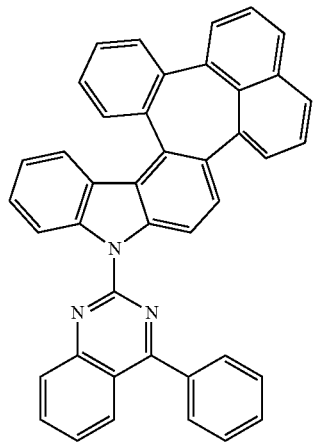
B-24
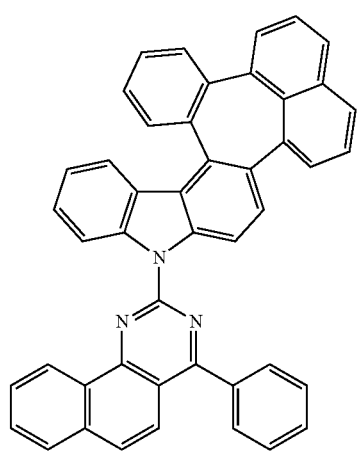
B-25
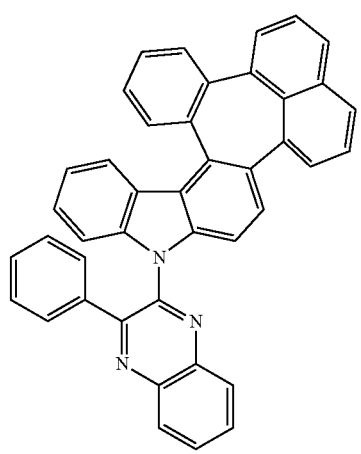

B-26
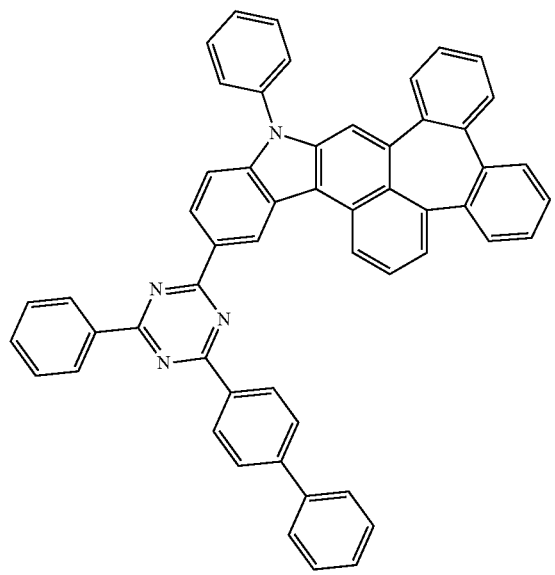
B-29
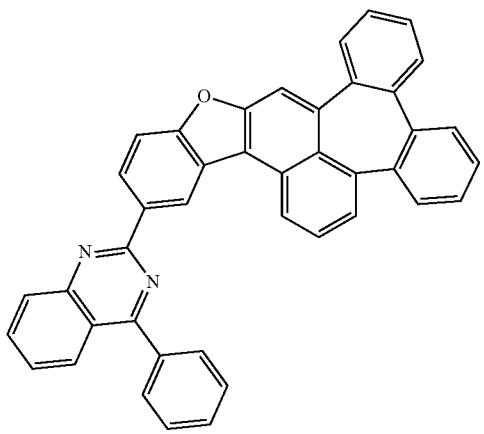
B-27
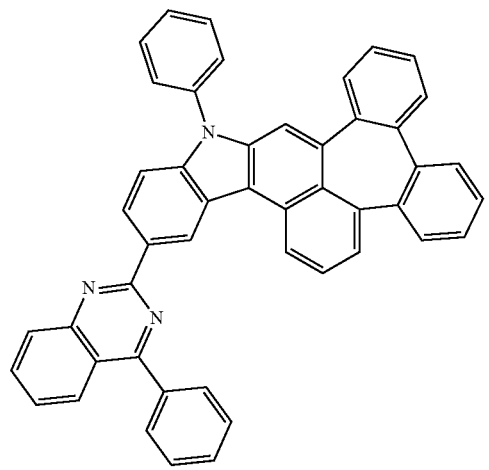
B-30
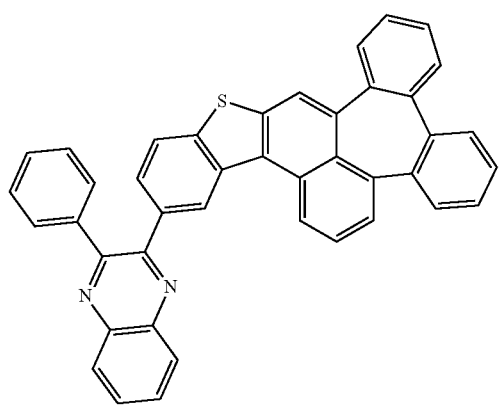
B-28
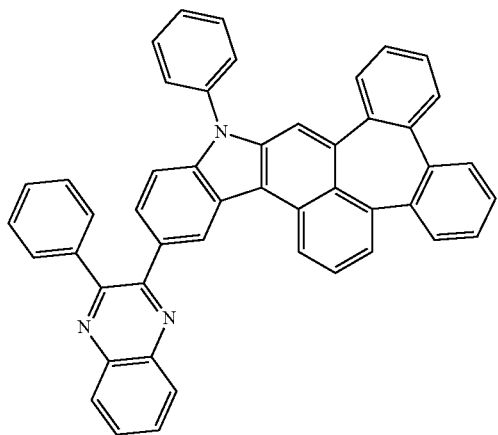
B-31
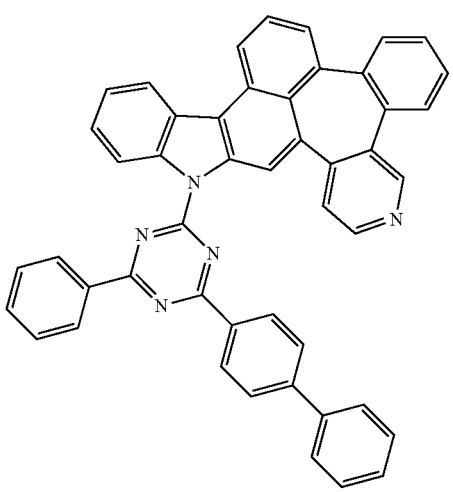

B-32
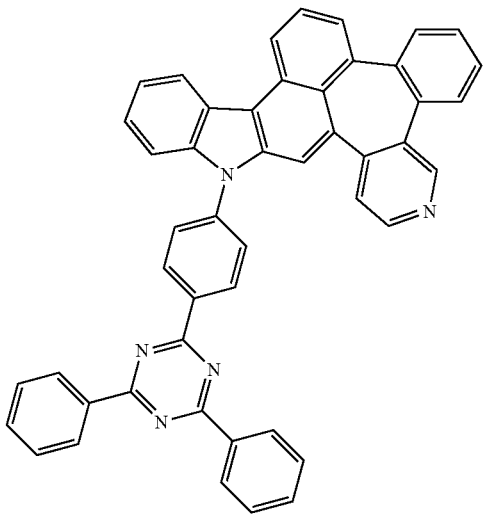
B-33
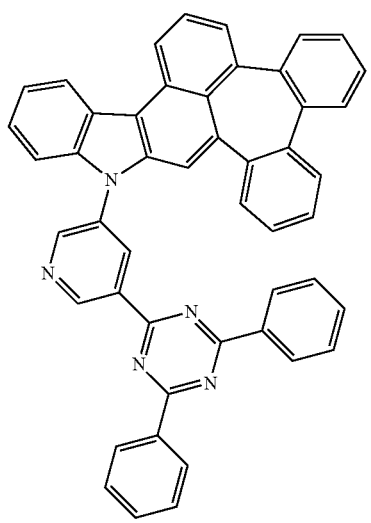
B-34
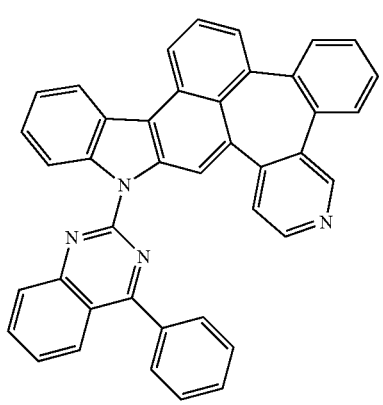
B-35
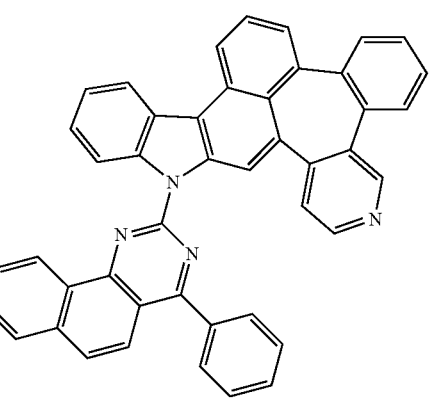
B-36
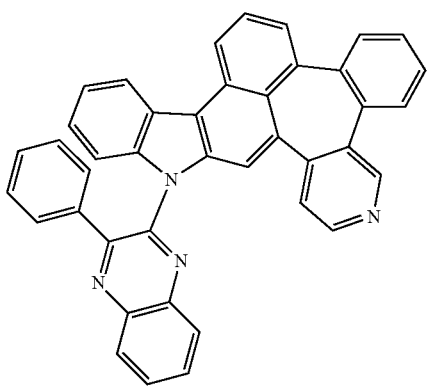
B-37
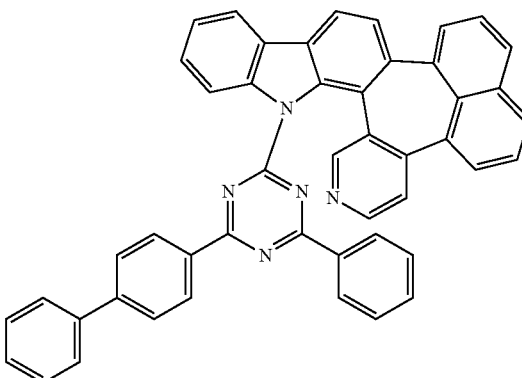
B-38
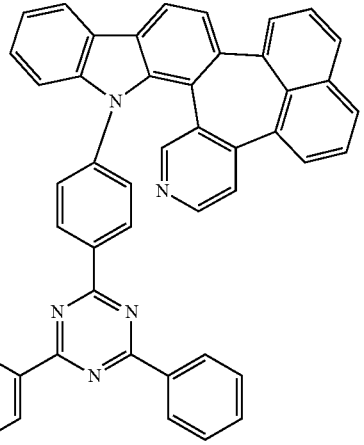

B-39
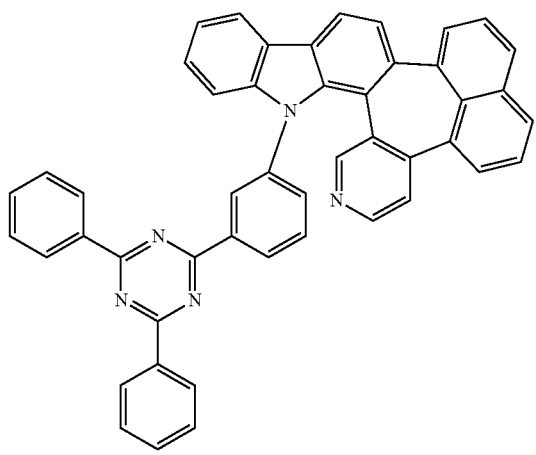
B-40
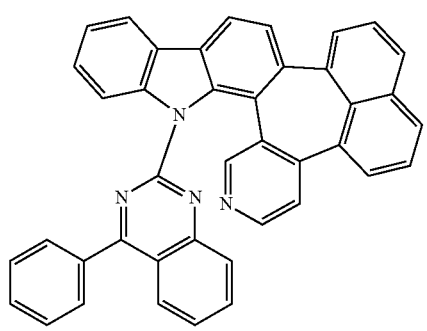
B-41
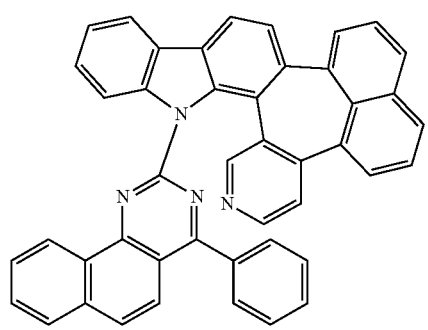
B-42
B-43
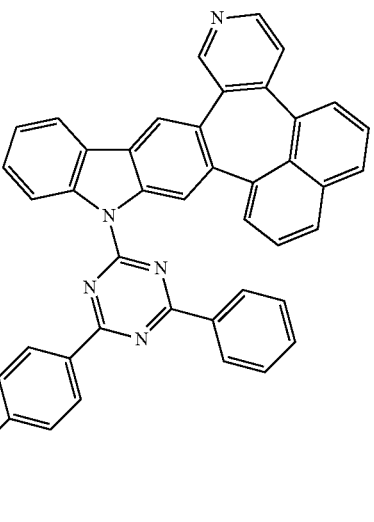
B-44
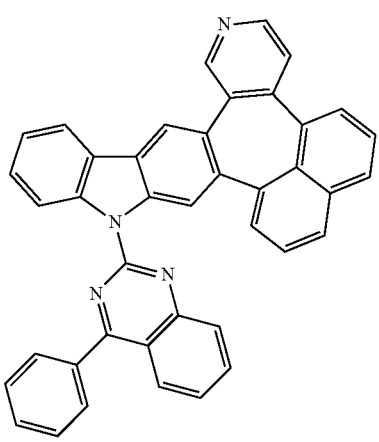
B-45
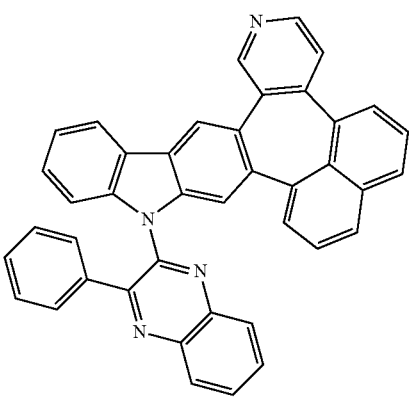

-continued
B-46
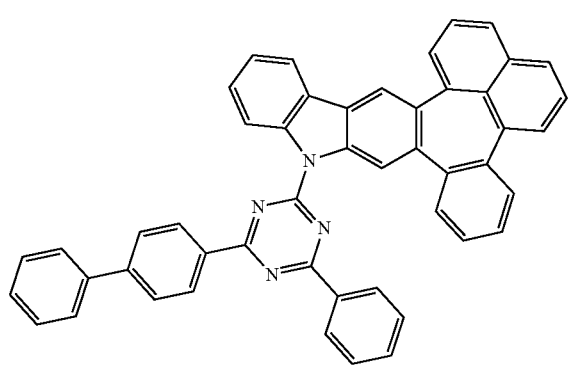
B-47
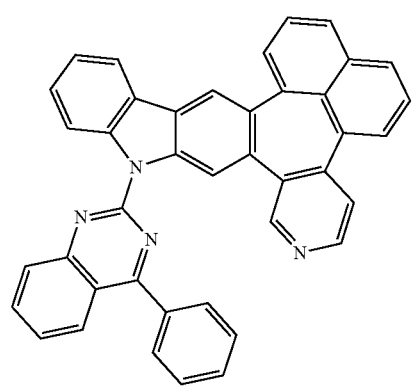
B-48
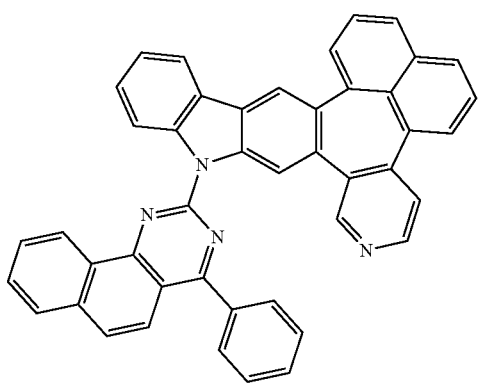
B-49
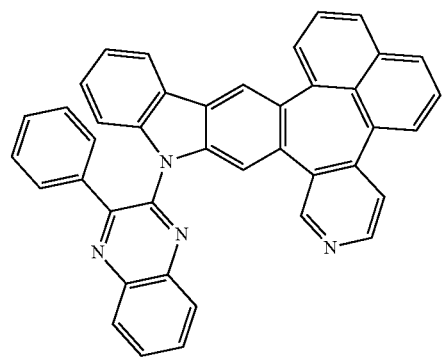
-continued
B-50
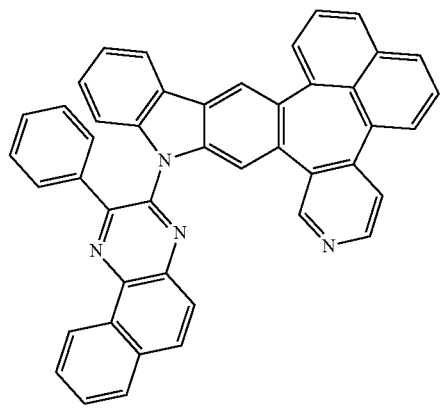
B-51
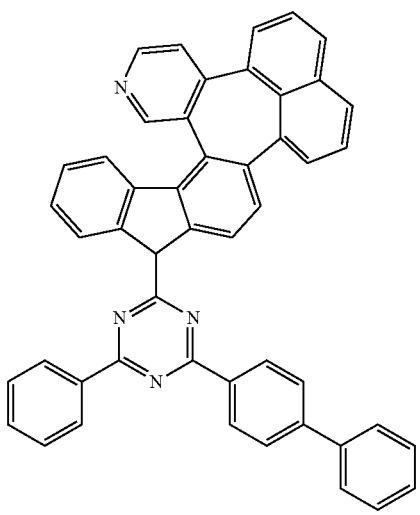
B-52
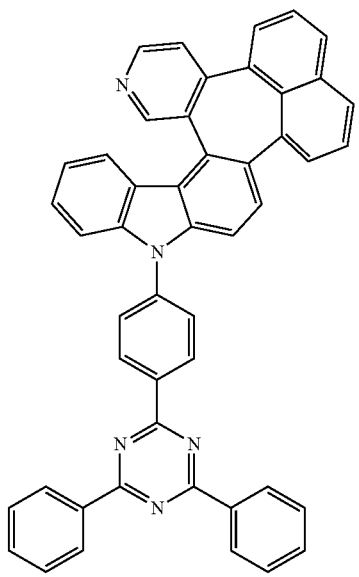

-continued
B-53
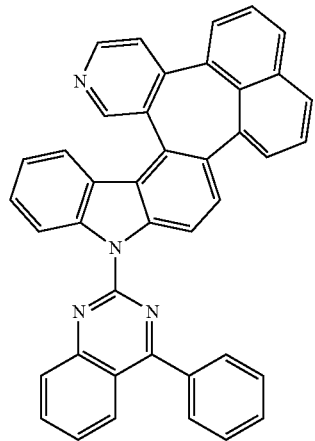
B-54
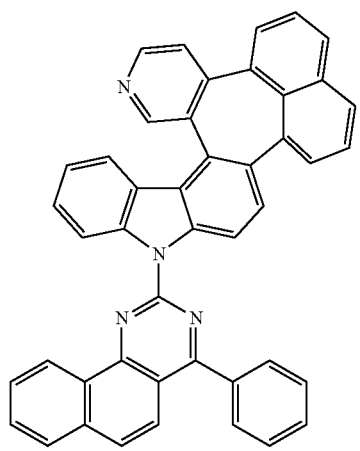
B-55
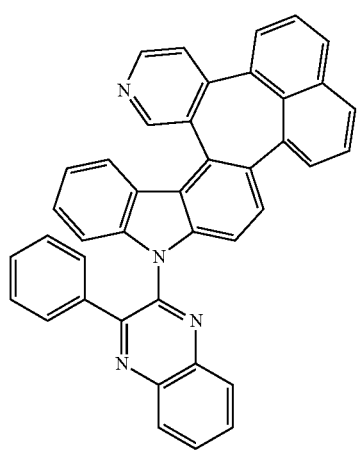
-continued
B-56
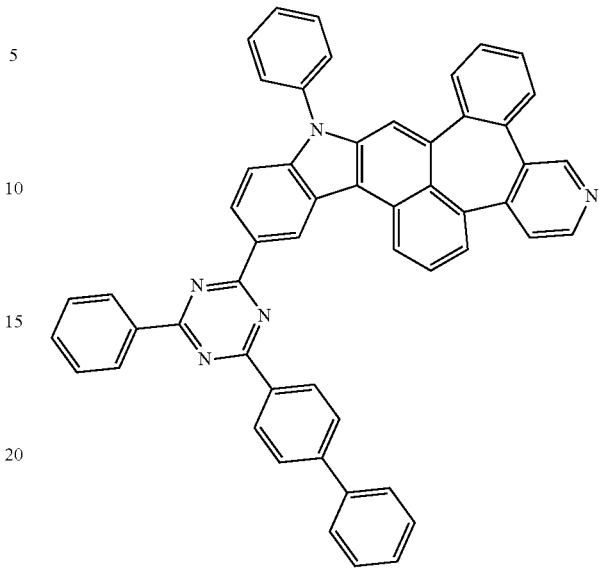
B-57
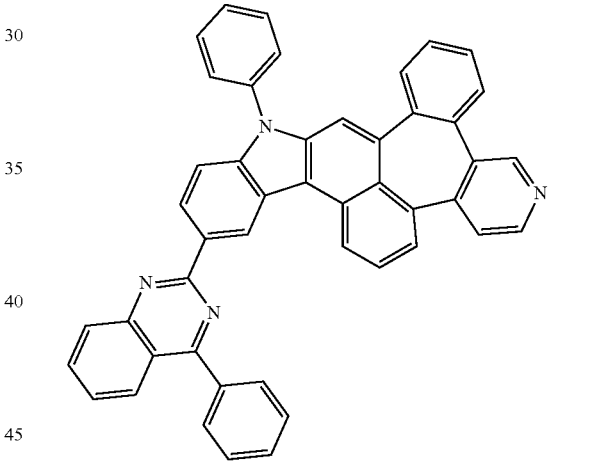
B-58
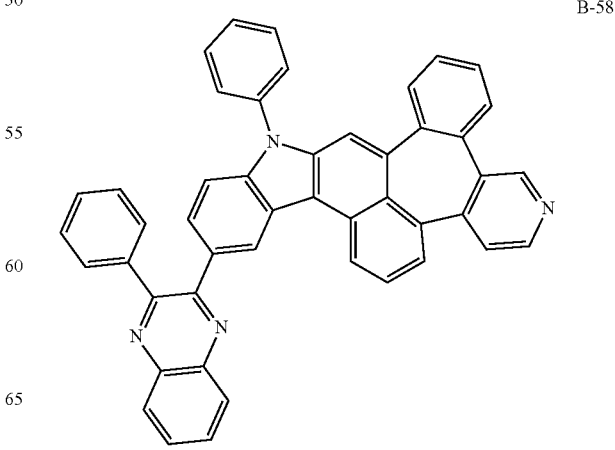

B-59
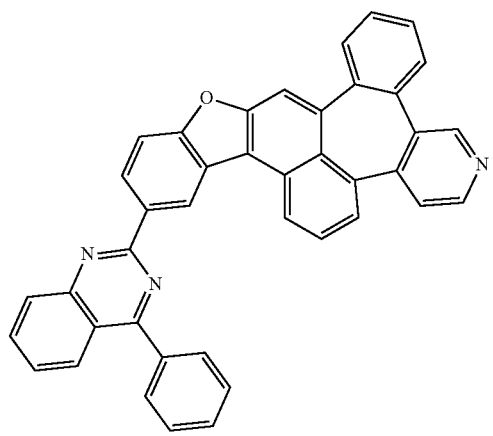

B-60
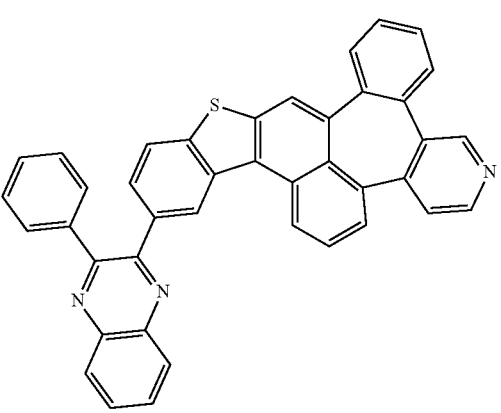

B-61
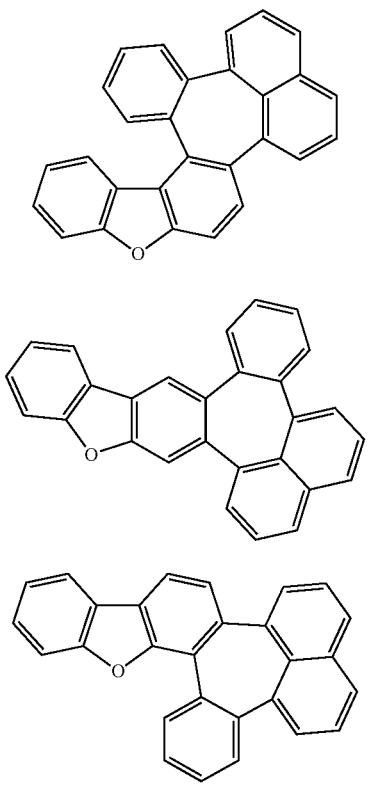

B-64
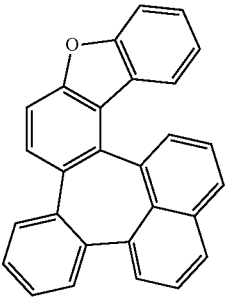

B-65
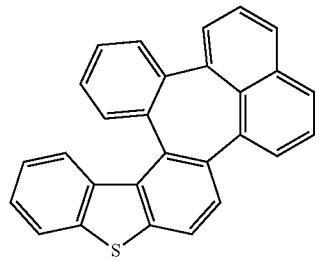

B-66
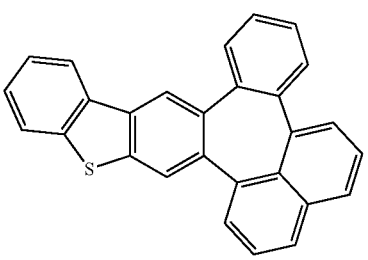

B-67
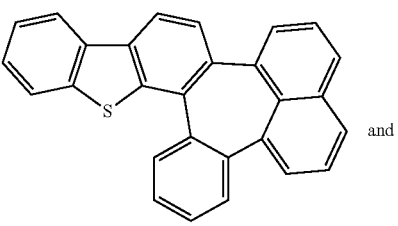

and

B-68
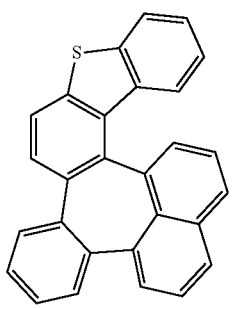

6. An organic electroluminescent material comprising the organic electroluminescent compound according to claim 1.

7. An organic electroluminescent device comprising the organic electroluminescent compound according to claim 1.

8. The organic electroluminescent device according to claim 7, wherein the organic electroluminescent compound is comprised in a light-emitting layer, a hole transport zone, or both of them.

* * * * *

UNITED STATES PATENT AND TRADEMARK OFFICE
CERTIFICATE OF CORRECTION

PATENT NO. : 11,926,591 B2
APPLICATION NO. : 16/968888
DATED : March 12, 2024
INVENTOR(S) : Hong-Se Oh et al.

Page 1 of 9

It is certified that error appears in the above-identified patent and that said Letters Patent is hereby corrected as shown below:

In the Specification

At Column 2, Line number 55-65: replace " 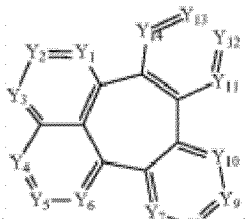 " with 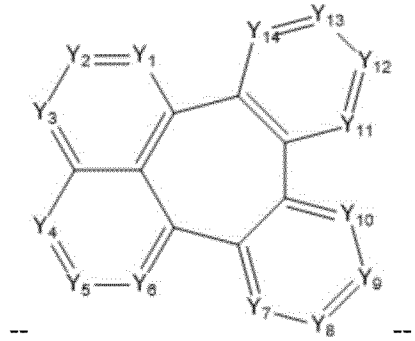 --

At Column 3, Line number 10-15: replace " 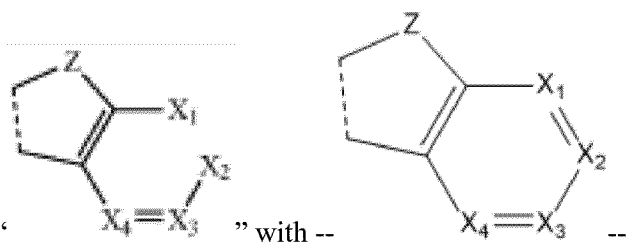 " with -- 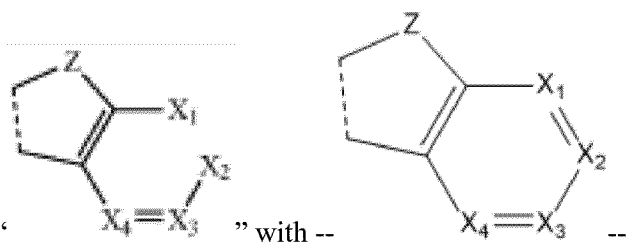 --

Signed and Sealed this
Seventh Day of May, 2024

Katherine Kelly Vidal
Director of the United States Patent and Trademark Office

CERTIFICATE OF CORRECTION (continued)
U.S. Pat. No. 11,926,591 B2

At Column 8, Line number 5-17: replace " 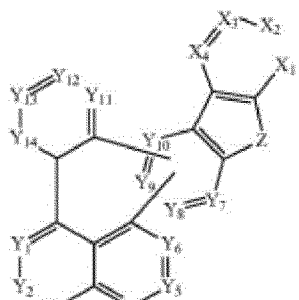 " with

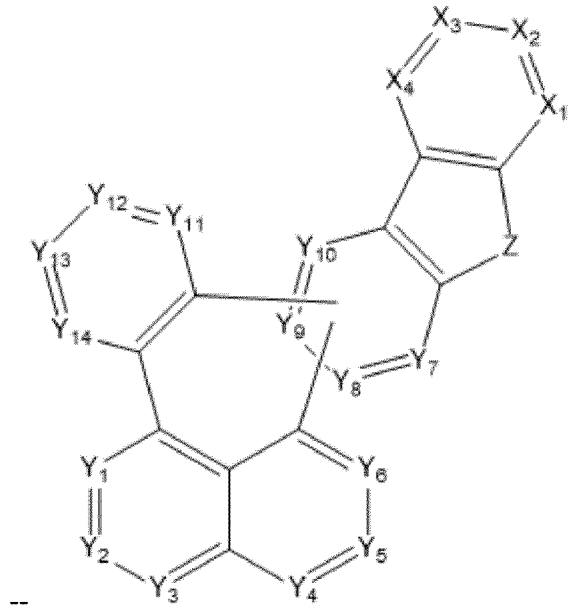

-- --

At Column 8, Line number 18-33: replace " 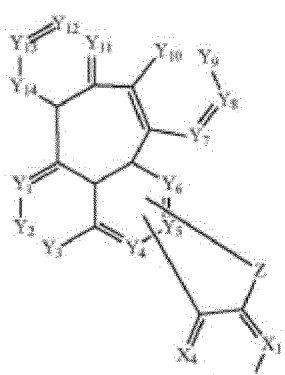 " with

CERTIFICATE OF CORRECTION (continued)
U.S. Pat. No. 11,926,591 B2

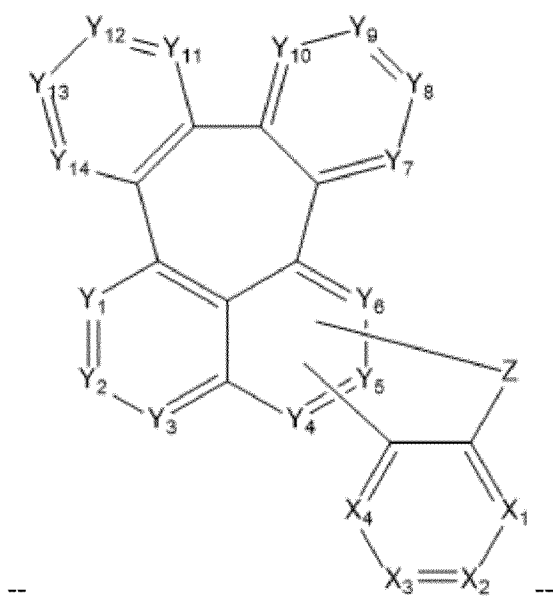
--

At Column 53, Line number 1-10: replace "  " with

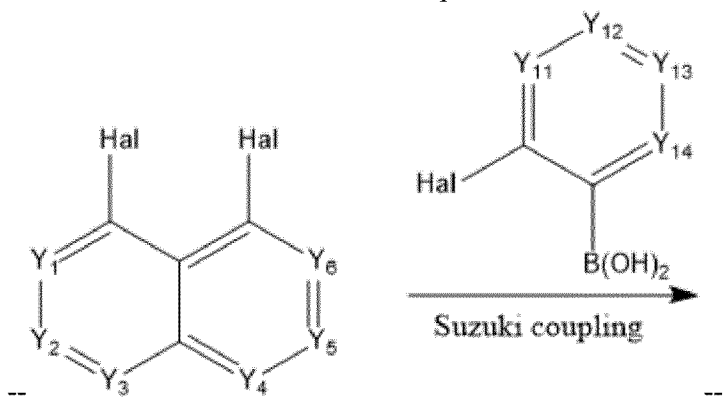
--

At Column 53, Line number 11-20: replace " 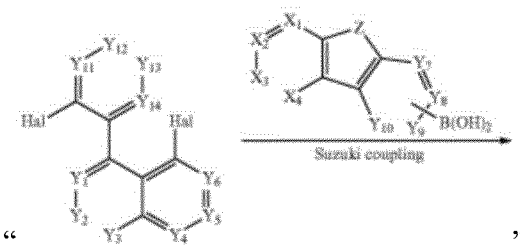 " with

CERTIFICATE OF CORRECTION (continued)
U.S. Pat. No. 11,926,591 B2

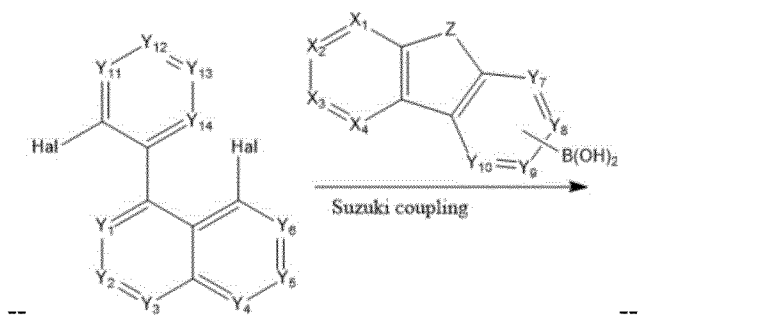

At Column 53, Line number 25-34: replace " 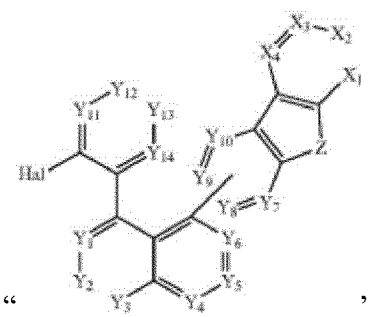 " with

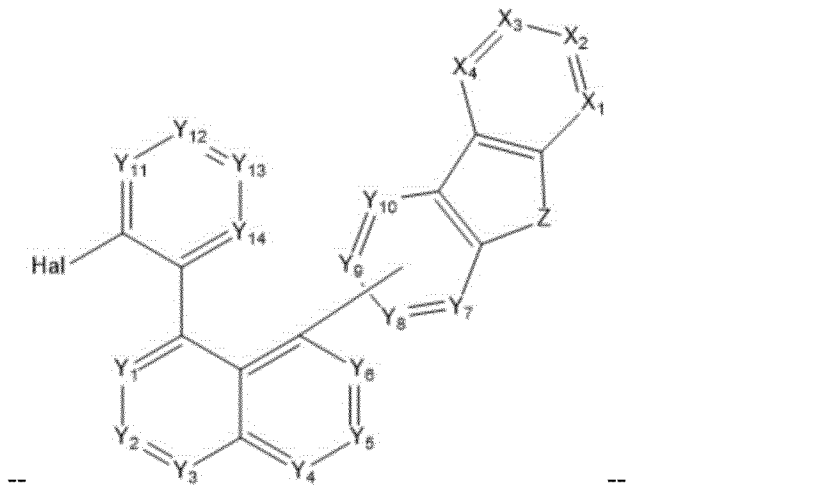

-- --

At Column 53, Line number 35-46: replace " 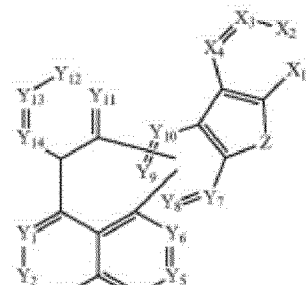 " with

CERTIFICATE OF CORRECTION (continued)
U.S. Pat. No. 11,926,591 B2

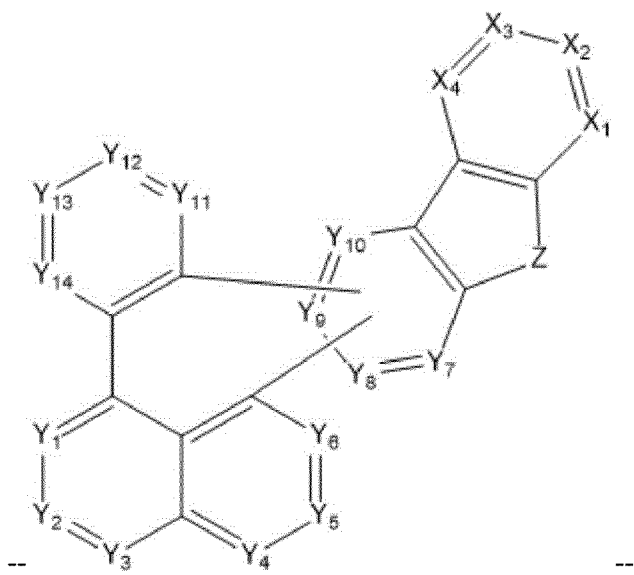
--

At Column 53, Line number 50-55: replace " 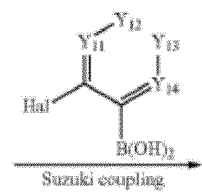 " with

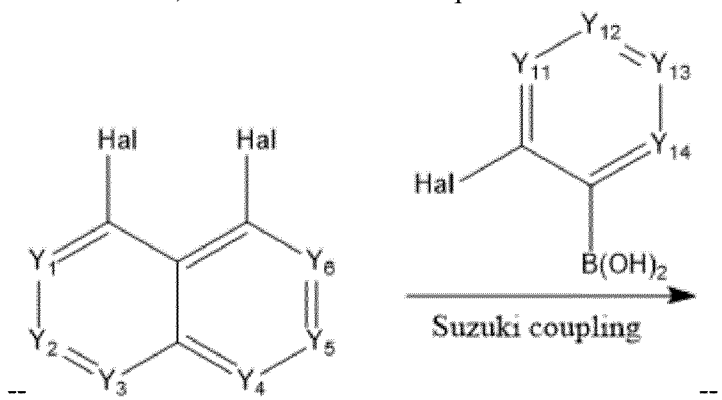
--

At Column 53, Line number 56-66: replace " 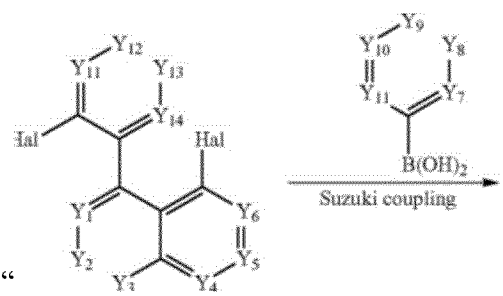 " with

CERTIFICATE OF CORRECTION (continued)
U.S. Pat. No. 11,926,591 B2

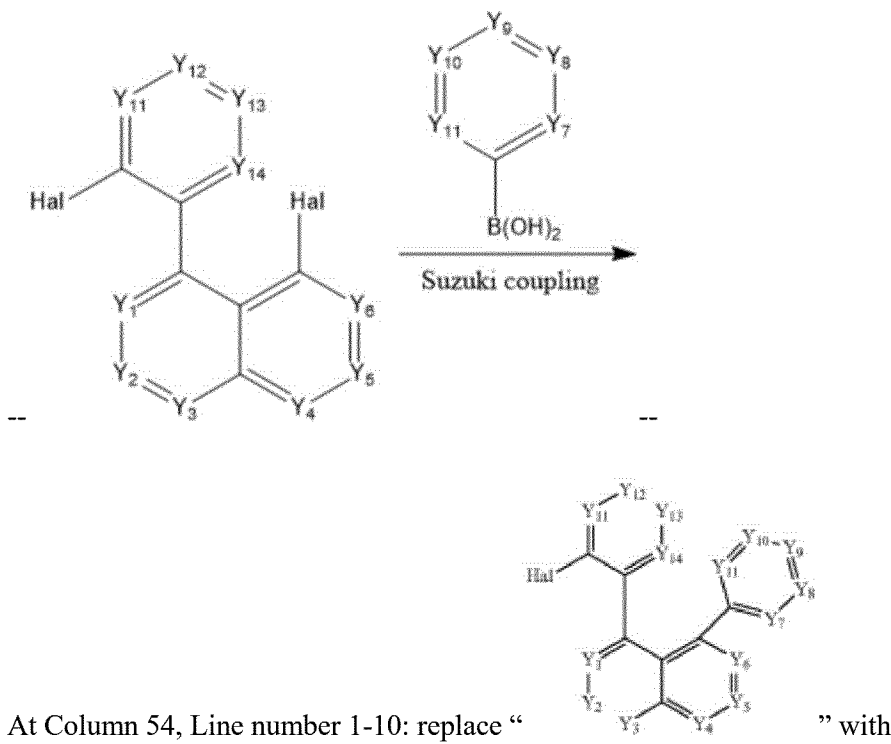

At Column 54, Line number 1-10: replace " " with

" "

At Column 54, Line number 20-28: replace " " with

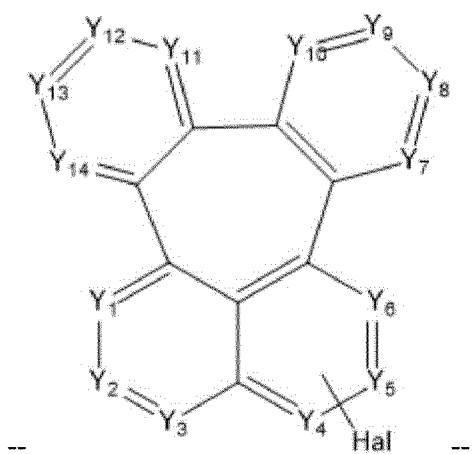
At Column 54, Line number 30-42: replace " 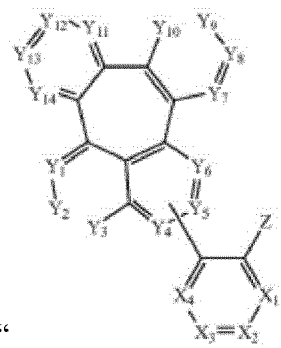 " with 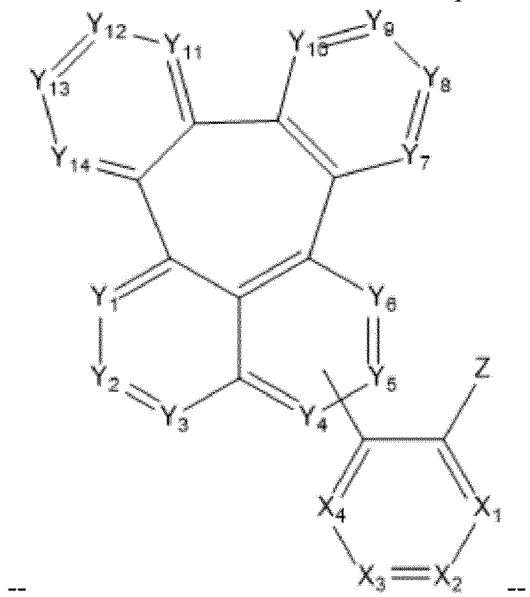

CERTIFICATE OF CORRECTION (continued)
U.S. Pat. No. 11,926,591 B2

At Column 54, Line number 43-55: replace " 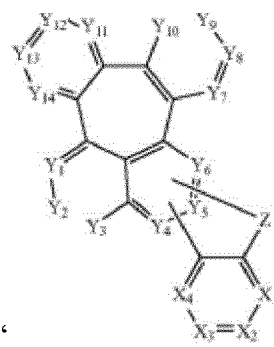 " with 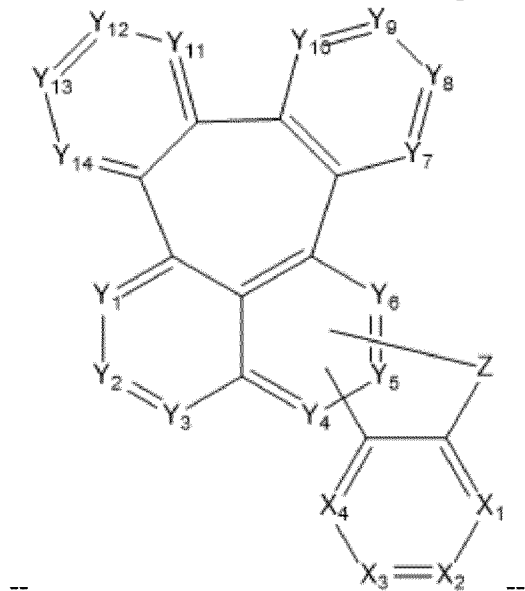 --

In the Claims

At Column 77, Claim number 1, Line number 55-65: replace " 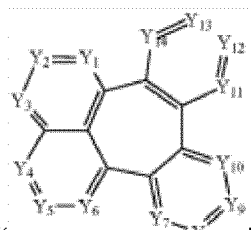 " with

CERTIFICATE OF CORRECTION (continued)
U.S. Pat. No. 11,926,591 B2

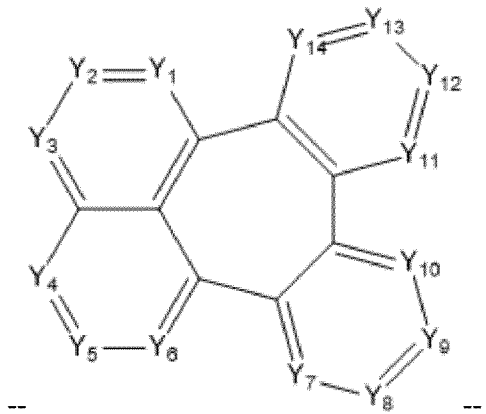
--

At Column 78, Claim number 1, Line number 60-65: replace "  " with

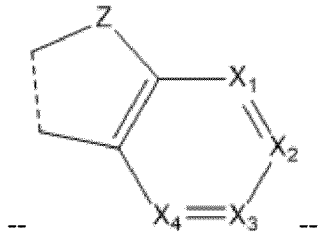
--